(12) United States Patent
Hanrahan et al.

(10) Patent No.: US 11,389,449 B2
(45) Date of Patent: Jul. 19, 2022

(54) TREATMENT OF METABOLIC SYNDROME WITH AN SGC STIMULATOR

(71) Applicant: Cyclerion Therapeutics, Inc., Cambridge, MA (US)

(72) Inventors: John P. Hanrahan, West Roxbury, MA (US); Albert Thomas Profy, Needham, MA (US); James D. Wakefield, Waltham, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/645,955

(22) PCT Filed: Sep. 14, 2018

(86) PCT No.: PCT/US2018/051195
§ 371 (c)(1),
(2) Date: Mar. 10, 2020

(87) PCT Pub. No.: WO2019/055859
PCT Pub. Date: Mar. 21, 2019

(65) Prior Publication Data
US 2020/0276195 A1 Sep. 3, 2020

Related U.S. Application Data

(60) Provisional application No. 62/688,086, filed on Jun. 21, 2018, provisional application No. 62/652,432, filed on Apr. 4, 2018, provisional application No. 62/575,577, filed on Oct. 23, 2017, provisional application No. 62/558,589, filed on Sep. 14, 2017.

(51) Int. Cl.
*A61K 31/506* (2006.01)
*A61P 3/06* (2006.01)
*A61P 3/10* (2006.01)
*A61K 9/00* (2006.01)
*A61K 45/06* (2006.01)

(52) U.S. Cl.
CPC .......... *A61K 31/506* (2013.01); *A61K 9/0053* (2013.01); *A61K 45/06* (2013.01); *A61P 3/06* (2018.01); *A61P 3/10* (2018.01)

(58) Field of Classification Search
CPC .................................................... A61K 31/506
See application file for complete search history.

(56) References Cited

U.S. PATENT DOCUMENTS

| 2010/0216764 A1 | 8/2010 | Kim et al. |
| 2021/0161893 A1* | 6/2021 | Im ............................ A61P 3/10 |

FOREIGN PATENT DOCUMENTS

| WO | 2005/011727 A1 | 2/2005 |
| WO | 2017/136309 A1 | 8/2017 |
| WO | 2018/089328 A1 | 5/2018 |

OTHER PUBLICATIONS

Buys et al., Discovery and development of next generation sGC stimulators with diverse multidimensional pharmacology and broad therapeutic potential. Nitric Oxide. 2018;78:72-80.
International Search Report and Written Opinion for Application No. PCT/US2018/051195, dated Dec. 13, 2018, 9 pages.

* cited by examiner

*Primary Examiner* — Rei Tsang Shiao
(74) *Attorney, Agent, or Firm* — McCarter & English, LLP; Steven G. Davis; Xin Zhang

(57) ABSTRACT

The present invention provides a method of treating a subject with metabolic syndrome by administering a stimulator of soluble guanylate cyclase (sGC) (Compound I) either alone or in combination therapy with a blood glucose lowering (antihyperglycemic or antidiabetes) medication, a blood pressure lowering (anti-hypertensive) medication, an anti-hyperlipidemic medication, or combinations thereof. It also relates to a method of reducing the level of a clinical marker selected from the group comprising of fasting blood glucose levels, fasting blood insulin levels, hemoglobin A1C (HbA1C) levels, blood cholesterol levels (total or LDL), blood ApoB levels, HOMA-IR levels, blood triglyceride levels, blood concentration of ADMA, blood levels of alanine transaminase, aspartate transaminase, and GGT, body weight and abdominal circumference, or any combination of these markers thereof, in a subject in need thereof by administering a stimulator of sGC (Compound I) either alone or in combination therapy with a blood glucose lowering (antihyperglycemic or antidiabetes) medication, a blood pressure lowering (anti-hypertensive) medication, an anti-hyperlipidemic medication, or combinations thereof.

21 Claims, 30 Drawing Sheets

TREATMENT OF METABOLIC SYNDROME WITH AN SGC STIMULATOR

RELATED APPLICATIONS

This application claims the benefit of the filing date, under 35 U.S.C. § 119(e), of U.S. Provisional Application No. 62/558,589, filed on Sep. 14, 2017, U.S. Provisional Application No. 62/575,577, filed on Oct. 23, 2017, U.S. Provisional Application No. 62/652,432, filed on Apr. 4, 2018, and U.S. Provisional Application No. 62/688,086, filed on Jun. 21, 2018. The entire contents of each of the above-referenced applications are incorporated herein by reference.

FIELD OF THE INVENTION

This disclosure relates to a method of treating a subject with metabolic syndrome by administering a stimulator of soluble guanylate cyclase (sGC) either alone or in combination therapy with a blood glucose lowering medication, a blood pressure lowering medication, or an anti-hyperlipidemic medication or a combination thereof. It also relates to a method of reducing the level of a clinical marker selected from the group comprising of fasting blood glucose levels, fasting blood insulin levels, hemoglobin A1C (HbA1C) levels, blood cholesterol levels, blood LDL cholesterol levels, blood triglyceride levels, blood apolipoprotein B (ApoB) levels, HOMA-IR levels, blood asymmetric dimethylarginine (ADMA) concentrations, blood levels of liver enzymes alanine transaminase (ALT), aspartate transaminase (AST), gamma-glutamyl transferase (GGT), and body weight, or any combination of these markers thereof, in a subject in need thereof by administering a stimulator of sGC either alone or in combination therapy with a blood glucose lowering medication, a blood pressure lowering medication, an anti-hyperlipidemic medication, or a combination thereof.

It also relates to a method of increasing insulin sensitivity, in a subject in need thereof by administering a stimulator of sGC either alone or in combination therapy with a blood glucose lowering medication, a blood pressure lowering medication, an anti-hyperlipidemic medication, or a combination thereof. It also relates to a method of improving liver function in a subject in need thereof by administering a stimulator of sGC either alone or in combination therapy with a blood glucose lowering medication, a blood pressure lowering medication, an anti-hyperlipidemic medication, or a combination thereof. It also relates to a method of improving endothelial function and reducing cardiovascular risk in a subject in need thereof by administering a stimulator of sGC either alone or in combination therapy with a blood glucose lowering medication, a blood pressure lowering medication, an anti-hyperlipidemic medication, or a combination thereof.

BACKGROUND OF THE INVENTION

In the body, nitric oxide (NO) is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long-term potentiation; and constitutive endothelial NOS (eNOS or NOS III) which regulates smooth muscle relaxation and blood pressure. Experimental and clinical evidence has indicated that reduced NO concentrations, reduced NO bioavailability and/or reduced responsiveness to endogenously produced NO contributes to the development of disease.

sGC is the primary receptor enzyme for NO in vivo. sGC can be activated via both NO-dependent and NO-independent mechanisms. In response to this activation, sGC converts guanosine-5'-triphosphate (GTP) into the secondary messenger cyclic guanosine monophosphate (cGMP). The increased level of cGMP, in turn, modulates the activity of downstream effectors including protein kinases, phosphodiesterases (PDEs) and ion channels.

Two classes of compounds have been identified in the last decades that are able to agonize the sGC receptor: sGC stimulators and sGC activators. NO-independent, heme-dependent sGC stimulators have displayed several important differentiating characteristics when compared with NO-independent, heme-independent sGC activators. These include crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed.

Increased concentration of cGMP as a result of sGC stimulation leads to vasodilation, anti-hypertensive effects, inhibition of platelet aggregation and adhesion, anti-remodeling effects, anti-apoptotic effects, anti-inflammatory, anti-fibrotic effects and neuronal signal transmission effects. Thus, sGC stimulators may be used to treat and/or prevent a range of diseases and disorders. sGC stimulators may also be useful in the prevention and/or treatment of diseases and disorders characterized by undesirable reduced bioavailability of and/or sensitivity to NO, such as those associated with conditions of oxidative stress or nitrosative stress.

Compounds that stimulate sGC in an NO-independent manner offer considerable advantages over other current alternative therapies that either target the aberrant NO pathway or otherwise benefit from the upregulation of the NO pathway, such as inter alia, Arginine, NO-donors, or PDE5 inhibitors. Compound I depicted below has demonstrated the ability to boost cGMP levels and has displayed many effects in animal models and in several humans clinical trials that are consistent with stimulation of sGC.

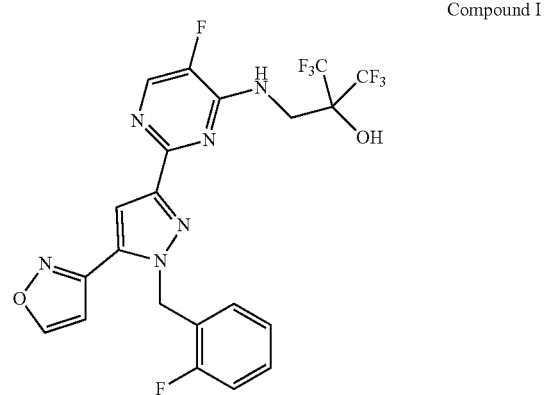 [SMILES: OC(CNc1nc(-c2cc(-c3ccon3)n(Cc3ccccc3F)n2)ncc1F)(C(F)(F)F)C(F)(F)F]

Compound I

SUMMARY OF THE INVENTION

The present invention is based on the surprising findings that Compound I administered with specific dosage regimens demonstrated the ability to positively affect markers of metabolic syndrome when used in combination with a blood glucose lowering medication and a blood pressure lowering medication. In some cases, the combination also included an anti-hyperlipidemic medication (see results from a Phase IIa clinical trial described in Example 3 and results from a second Phase IIa clinical trial described in Example 4).

The present invention is directed to a method of treating metabolic syndrome in a human patient in need thereof by administering a total oral daily dose of between 10 mg to 70 mg, between 10 mg to 60 mg, or between 10 mg to 50 mg of Compound I to said patient.

In another embodiment, the invention relates to a method of treating metabolic syndrome in a patient in need thereof by administering to the patient a total oral daily dose of between 10 mg to 70 mg, between 10 mg to 60 mg, or between 10 mg to 50 mg of Compound I in combination with an anti-hypertensive medication.

In another embodiment, the invention relates to a method of treating metabolic syndrome in a patient in need thereof by administering to the patient a total oral daily dose of between 10 mg to 70 mg, between 10 mg to 60 mg, or between 10 mg to 50 mg of Compound I in combination with a blood glucose lowering medication.

In another embodiment, the invention relates to a method of treating metabolic syndrome in a patient in need thereof by administering to the patient a total oral daily dose of between 10 mg to 70 mg, between 10 mg to 60 mg, or between 10 mg to 50 mg of Compound I in combination with an anti-hyperlipidemic medication.

In another embodiment, the invention relates to a method of treating metabolic syndrome in a patient in need thereof by administering to the patient a total oral daily dose of between 10 mg to 70 mg, between 10 mg to 60 mg, or between 10 mg to 50 mg of Compound I in combination with a blood glucose lowering medication, an anti-hypertensive medication, and, optionally, an anti-hyperlipidemic medication.

In another embodiment, the invention relates to a method of reducing the level of a metabolic marker selected from the group consisting of fasting blood glucose levels, fasting blood insulin levels, HbA1C levels, blood cholesterol levels (total or low-density lipoprotein (LDL) cholesterol levels), blood triglyceride levels, blood apolipoprotein B (ApoB) levels, HOMA-IR levels, ADMA blood concentrations, blood levels of alanine transaminase (ALT), aspartate transaminase (AST), and gamma-glutamyl transferase (GGT), abdominal circumference, and body weight, or of any combination of these markers thereof, in a patient in need thereof by administering to the patient a total oral daily dose of between 10 mg to 70 mg, between 10 mg to 60 mg, or between 10 mg to 50 mg of Compound I, either alone or in combination with a blood glucose lowering medication, an anti-hypertensive medication, an anti-hyperlipidemic medication or a combination thereof.

In another embodiment, the invention provides a method of increasing insulin sensitivity in a patient in need thereof by administering to the patient a total oral daily dose of between 10 mg to 70 mg, between 10 mg to 60 mg, or between 10 mg to 50 mg of Compound I, either alone or in combination with a blood glucose lowering medication, an anti-hypertensive medication, an anti-hyperlipidemic medication or a combination thereof. In one embodiment, the level of insulin sensitivity in a patient is measured by the HOMA-IR level. In one embodiment, the patient is not taking insulin.

In another embodiment, the invention provides a method of improving endothelial function and reducing cardiovascular risk in a patient in need thereof by administering to the patient a total oral daily dose of between 10 mg to 70 mg, between 10 mg to 60 mg, or between 10 mg to 50 mg of Compound I, either alone or in combination with a blood glucose lowering medication, an anti-hypertensive medication, an anti-hyperlipidemic medication or a combination thereof. In one embodiment, the improvement in endothelial function in a patient is measured by the reduction in the ADMA blood concentration in the patient.

In another embodiment, the invention provides a method of improving liver function in a subject in need thereof by administering to the patient a total daily dose of between 10 mg to 70 mg, between 10 mg to 60 mg, or between 10 mg to 50 mg of Compound I, either alone or in combination with a blood glucose lowering medication, an anti-hypertensive medication, an anti-hyperlipidemic medication, or a combination thereof. In one embodiment, the degree of improvement in liver function is determined by measuring the decrease in blood levels of alanine transaminase (ALT), aspartate transaminase (AST) and/or gamma-glutamyl transferase (GGT).

Also included in the present invention is Compound I for use in the treatment of metabolic syndrome in a human patient in need thereof, wherein a total oral daily dose of 10 mg to 70 mg, between 10 mg to 60 mg, or between 10 mg to 50 mg of Compound I is administered to the patient alone or in combination with a blood glucose lowering medication, an anti-hypertensive medication, an anti-hyperlipidemic medication or a combination thereof.

DETAILED DESCRIPTION OF THE INVENTION

Definitions and General Terminology

Figure 1:
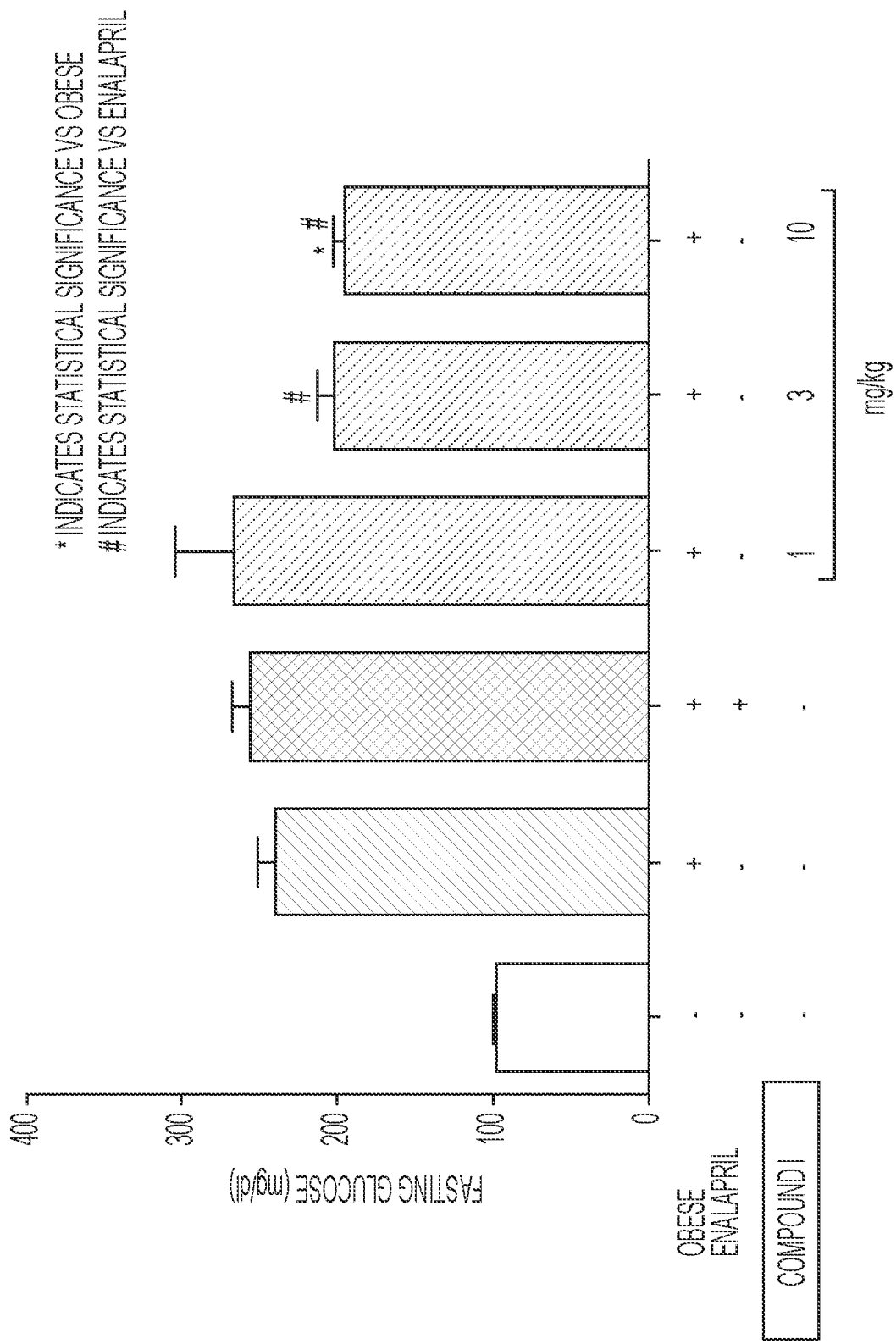
FIG. 1 shows fasting glucose levels upon treatment with Compound I or enalapril in the obese ZSF1 rat model (Example 1).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

As used herein, the terms "subject" and "patient" are used interchangeably. A subject or a patient is a human patient or human subject.

For the terms "for example" and "such as," and grammatical equivalences thereof, the phrase "without limitation" or "and without limitation" is understood to follow unless explicitly stated otherwise.

As used herein, the term "metabolic syndrome", refers to a group or cluster of metabolic conditions, clinical presentations or symptoms (such as abdominal obesity, elevated fasting blood glucose, elevated HbA1C, insulin resistance, "dyslipidemia" (i.e., elevated lipid levels), elevated blood pressure (HBP), endothelial dysfunction and liver dysfunction), which occur together more often than by chance alone and that together put the patient at risk of developing type 2 diabetes, heart disease and stroke. A patient may display only some or all of these metabolic conditions, clinical presentations or symptoms at the same time.

A patient with metabolic syndrome may be characterized by a specific blood sugar dysregulation profile characterized by one or more of high fasting blood glucose and insulin levels, insulin resistance (as measured by high HOMA-IR values) and elevated HbA1C levels.

A patient with metabolic syndrome may be characterized by a specific lipid profile of increased triglycerides, decreased high-density lipoprotein cholesterol (HDL-cholesterol) and in some cases moderately elevated low-density lipoprotein cholesterol (LDL-cholesterol) levels and ApoB levels, as well as accelerated progression of "atherosclerotic disease" due to the pressure of the component risk factors. There are several types of dyslipidemias: "hypercholesterolemia" refers to elevated levels of cholesterol. Familial hypercholesterolemia is a specific form of hypercholesterolemia due to a defect on chromosome 19 (19p13.1-13.3). "Hyperglyceridemia" refers to elevated levels of glycerides (e.g., "hypertriglyceridemia" involves elevated levels of triglycerides (TGs)). "Hyperlipoproteinemia" refers to elevated levels of lipoproteins (usually LDL or ApoB unless otherwise specified).

A patient with metabolic syndrome may also display endothelial dysfunction, characterized by elevated levels of ADMA. Currently, what constitute normal levels of ADMA is still not fully characterized for all patient populations and this is an evolving field of research. See for example: "The issue of plasma asymmetric dimethylarginine reference range, A systematic review and meta-analysis", Balázs Németh, Zénó Ajtay, László Hejjel, Tamás Ferenci, Zoltán Abrám, Edit Murányi, István Kiss, PLoS ONE 12(5): e0177493 (11 May 2017); "Health-associated reference values for arginine, asymmetric dimethylarginine (ADMA) and symmetric dimethylarginine (SDMA) measured with high-performance liquid chromatography", Garmo G. Hov, E. Sagen, A. Bigonah and A. Åsberg, *Scandinavian Journal of Clinical and Laboratory Invenstigation*, 2007, 67(8): 868-876; "Plasma asymmetric dimethylarginie levels in healthy people", Tanya Deneva-Kovcheva, Lyudmila Vladimirova-Kitova, Evgeniya Angelova and Todorka Tsvetkova, *Folia Med. (Plovdiv)*, 2011, January-March, 53(1):28-33; "Association of endothelial dysfunction with cardiovascular risk factors and new-onset diabetes mellitus in patients with hypertension", Cristina Bergmann Triches, Saurus Mayer, Beata Marie Redublo Quinto, Marcelo Costa Batista, Maria Teresa Zanella, *J Clin Hypertens.* 2018; 20:935-941.

However multiple studies have found association between higher levels of ADMA and increased cardiovascular risk. Therefore, it is becoming increasingly clear that ADMA, which is the main endogenous inhibitor of nitric oxide synthase, plays a critical role in the process of endothelial dysfunction and that reductions in elevated ADMA levels may be indicative of improving endothelial function.

A patient with metabolic syndrome may also display impaired liver function, characterized by elevated blood level of liver enzymes, such as alanine transaminase (ALT), also known as alanine aminotransferase, and aspartate transaminase (AST), also known as asparate aminotransferase. Levels of gamma-glutamyl transferase (GGT) may also be elevated when liver function is impaired.

Thus, clinical markers of metabolic syndrome include but are not limited to: elevated fasting blood glucose levels, elevated fasting blood insulin levels, elevated HbA1C levels, elevated blood cholesterol levels (total and LDL), reduced blood HDL levels, elevated blood ApoB levels, elevated blood triglyceride levels, elevated levels of HOMA-IR, elevated blood levels of liver enzymes (ALT, AST and GGT), elevated ADMA blood concentrations and obesity. A particular patient may display all or only some of these clinical markers simultaneously.

In certain embodiments, the patient with metabolic syndrome has systolic blood pressure ≥130 mm Hg and/or diastolic blood pressure ≥85 mm Hg.

In certain embodiments, the patient with metabolic syndrome has a fasting blood glucose level of 100 mg/dL or higher. In other embodiments, a patient with metabolic syndrome has a fasting blood glucose level of 95 mg/dL or higher.

In certain embodiments, the patient with metabolic syndrome has HDL cholesterol less than 40 mg/dL for men or less than 50 mg/dL for women.

In some embodiments, normal LDL cholesterol levels are considered to be less than 100 mg/dL. In other embodiments, levels of LDL cholesterol of 100 to 129 mg/dL are considered acceptable for people with no health issues but may be of more concern for those with heart disease or heart disease risk factors. In other embodiments, a reading of 130 to 159 mg/dl is considered borderline high and a reading of 160 to 1.89 mg/di, is considered high.

In certain embodiments, the patient with metabolic syndrome has blood triglyceride levels of 150 mg/dL or higher.

In certain embodiment, the patient with metabolic syndrome has a waist circumference of 102 cm (40 inches) or more for men and 88 cm (35 inches) or more for women.

In certain embodiments, the patient with metabolic syndrome has a HOMA-IR level of 1.9 or higher, indicative of early insulin resistance. In other embodiments, the patient with metabolic syndrome has a HOMA-IR level of 2.9 or higher, indicative of significant insulin resistance.

In certain embodiments, the patient with metabolic syndrome has a level of ALT above 25 IU/L (international units per liter) in females and 33 IU/L in males. In certain embodiments, the patient with metabolic syndrome has a level of AST above 40 IU/L (international units per liter) in adults. According to the Mayo Clinic, the normal range for GGT levels is 9-48 units per liter (U/L). Normal values can vary due to age and sex.

The term "therapeutically effective amount" or "pharmaceutically effective amount" as used herein means that amount of active compound or pharmaceutical agent that elicits the medicinal response in a human that is being sought by a medical doctor or other clinician. The therapeutically or pharmaceutically effective amount of the compound is at least the minimum amount necessary to ameliorate, palliate, lessen, delay, reduce, alleviate or cure a disease, disorder or syndrome or one or more of its symptoms, signs or causes. In another embodiment it is the amount needed to bring abnormal levels of certain clinical markers of the disease, disorder or syndrome closer to the normal values or levels. An effective amount can be administered in one or more administrations throughout the day.

The terms "administer", "administering" or "administration" in reference to Compound I, mean introducing the compound into the body of the patient in need of treatment. When Compound I is used in combination with one or more other therapeutic agents, "administration" and its variants are each understood to encompass concurrent and/or sequential introduction of Compound I and the other therapeutic agents into the patient.

"Treat", "treating" or "treatment" with regard to a disorder, disease, condition, symptom or syndrome, refers to alleviating or abrogating the cause and/or the effects of the disorder, disease, condition, symptom or syndrome. As used herein, the terms "treat", "treatment" and "treating" also refer to the reduction or amelioration of the progression, severity and/or duration of metabolic syndrome, or the improvement of one or more symptoms (preferably, one or more discernible symptoms) of metabolic syndrome or amelioration of the progression of one or more symptoms (i.e. "managing" without "curing" the condition), resulting from the administration of one or more therapies. In specific embodiments, the terms "treat"; "treatment" and "treating" refer to the amelioration of at least one measurable physical parameter of metabolic syndrome. In other embodiments the terms "treat", "treatment" and "treating" refer to the inhibition of the progression of metabolic syndrome, either physically by, e.g., stabilization of at least one discernible symptom (e.g., weight) or physiologically by, e.g., stabilization of at least one physiological parameter (e.g. fasting glucose), or both.

The treatment of metabolic syndrome with Compound I can be carried out using the compound alone or in combination therapy with other therapeutic agents. In some particular embodiments, Compound I can be used for the treatment of metabolic syndrome in combination with a blood glucose lowering medicine, with a blood pressure lowering medicine, with an anti-hyperlipidemic medicine or combinations thereof.

Combination Therapies

As used herein, the terms "in combination" (as in the sentence "in combination therapy") or "co-administration" can be used interchangeably to refer to the use of more than one therapy. The use of the terms does not restrict the order in which therapies are administered to a subject.

The sGC stimulator Compound I can be used in combination therapy with one or more additional therapeutic agents (e.g, additional therapeutic agents described herein). For combination treatment with more than one therapeutic agents, where the therapeutic agents are in separate dosage formulations, or dosage forms, the therapeutic agents may be administered separately or in conjunction (i.e., at the same time). In addition, when administered separately, the administration of one therapeutic agent may be prior to or subsequent to the administration of the other agent.

When Compound I is used in combination therapy with other therapeutic agents, an "effective amount" of the other therapeutic agent or agents will depend on the type of drug used. Suitable dosages are known for approved therapeutic agents and can be adjusted by the skilled artisan according to the condition of the subject, the type of condition(s) being treated and the amount of a Compound I being used. In one embodiment of this invention, Compound I, and the additional therapeutic agent are each administered in an effective amount (i.e., each in an amount which would be therapeutically effective if administered alone). In other embodiments, Compound I and the additional therapeutic agent are each administered in an amount which alone does not provide a therapeutic effect (a sub-therapeutic dose). In yet another embodiment, Compound I can be administered in an effective amount, while the additional therapeutic agent is administered in a sub-therapeutic dose. In still another embodiment, Compound I can be administered in a sub-therapeutic dose, while the additional therapeutic agent, for example, a blood glucose lowering agent, a blood pressure lowering medicine or an anti-hyperlipidemic is administered in an effective amount.

When co-administration involves the separate administration of a first amount of Compound I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and pharmacokinetic profile. For example, Compound I and the second therapeutic agent can be administered in any order within 24 hours of each other, within 16 hours of each other, within 8 hours of each other, within 4 hours of each other, within 1 hour of each other or within 30 minutes of each other.

More, specifically, a first therapy can be administered prior to (e.g., 5 minutes, 15 minutes, 30 minutes, 45 minutes, 1 hour, 2 hours, 4 hours, 6 hours or 12 hours before)), concomitantly with, or subsequent to (e.g., 5 minutes, 15 minutes, 30 minutes, 45 minutes, 1 hour, 2 hours, 4 hours, 6 hours, 12 hours after), the administration of a second therapy to a subject.

Examples of other therapeutic agents that may be combined with Compound I include, but are not limited to those discussed below.

1. Blood glucose lowering medications (also referred as glycemic control medications) that may be used in combination with Compound I include, but are not limited to:
Metformin (Glucophage®, Glumetza® and others). Generally, metformin is the first medication prescribed for type 2 diabetes. It works by improving the sensitivity of body tissues to insulin so that the body uses insulin more effectively. Metformin also lowers glucose production in the liver. Metformin may not lower blood sugar enough on its own.

If metformin and lifestyles changes are not enough to control blood sugar levels, other oral or injected medications can be added.

Sulfonylureas. These medications help the body secrete more insulin. Examples of medications in this class include glyburide (DiaBeta®, Glynase®), glipizide (Glucotrol®) and glimepiride (Amaryl®).

Meglitinides. These medications work like sulfonylureas by stimulating the pancreas to secrete more insulin, but they are faster acting, and the duration of their effect in the body is shorter. Examples include repaglinide (Prandin®) and nateglinide (Starlix®).

Thiazolidinediones. Like metformin, these medications make the body's tissues more sensitive to insulin. Rosiglitazone (Avandia®) and pioglitazone (Actos®) are examples of thiazolidinediones.

DPP-4 inhibitors (or DPP-IV inhibitors). These medications help reduce blood sugar levels, but tend to have a modest effect. Examples of these medications are sitagliptin (Januvia®), saxagliptin (Onglyza®) and linagliptin (Tradjenta®).

GLP-1 receptor agonists. These medications slow digestion and help lower blood sugar levels, though not as much as sulfonylureas. Their use is often associated with some weight loss. Exenatide (Byetta®), dulaglutide (Trulicity®) and liraglutide (Victoza®) are examples of GLP-1 receptor agonists. Possile side effects include nausea and an increased risk of pancreatitis.

SGLT2 inhibitors. These are the newest diabetes drugs on the market. They work by preventing the kidneys from reabsorbing sugar into the blood. Instead, the sugar is excreted in the urine. Examples include empagliflozin (Jardiance®), ipragliflozin (ASP-1941 or Suglat®), tofogliflozin (Apleway®, Beberza®), sergliflozin etabonate, remogliflozin etabonate (BHV091009), ertugliflozin (Steglatro®), sotagliflozin, canagliflozin (Invokana®) and dapagliflozin (Farxiga®). In one embodiment, the SGLT2 inhibitor is empagliflozin (Jardiance®).

Insulin therapy. Some people who have type 2 diabetes need insulin therapy as well. In the past, insulin therapy was used as a last resort, but today it's often prescribed sooner because of its benefits. Because normal digestion interferes with insulin taken by mouth, insulin must be injected. Depending on the patients needs, the doctor may prescribe a mixture of insulin types to use throughout the day and night. Often, people with type 2 diabetes start insulin use with one long-acting shot at night.

There are many types of insulin, and they each work in a different way. Options include:

Insulin glulisine (Apidra®)
Insulin lispro (Humalog®)
Insulin aspart (Novolog®)
Insulin glargine (Lantus®)
Insulin detemir (Levemir®)
Insulin isophane (Humulin N, Novolin N®)
Mixtard (human insulin containing both fast-acting (soluble) and long-acting (isophane) insulin.

2. Blood pressure lowering medications (also known as anti-hypertensive medications) that may be used in combination with Compound I include, but are not limited to:

Thiazide diuretics. Diuretics, sometimes called water pills, are medications that act on the kidneys to help the body eliminate sodium and water, reducing blood volume. Thiazide diuretics are often the first, but not the only, choice in high blood pressure medications. Thiazide diuretics include hydrochlorothiazide (Microzide®), chlorthalidone and others. Diuretics or calcium channel blockers may work better for black and older people than do angiotensin-converting enzyme (ACE) inhibitors alone.

Beta blockers. These medications reduce the workload on the heart and open blood vessels, causing the heart to beat slower and with less force. Beta blockers include acebutolol (Sectral®), atenolol (Tenormin®), metoprolol (Lopressor® and Toprol XL®), nebivolol (Nebilet®, Bystolic®) and others. When prescribed alone, beta blockers don't work as well, especially in black and older people, but may be effective when combined with other blood pressure lowering medications.

Angiotensin-converting enzyme (ACE) inhibitors. These medications—such as lisinopril (Prinivil®, Zestril®, Qbrelis®), combinations of lisinopril with hydrochlorothiazide (Zestoretic®), benazepril (Lotensin), captopril (Capoten), enalapril (Vasotec®, Renitec®, Epaned®, Enacard®) and others—help relax blood vessels by blocking the formation of a natural chemical that narrows blood vessels. People with chronic kidney disease may benefit from having an ACE inhibitor as one of their medications. Other ACE inhibitors that may be combined with Compound I in the treatment of metabolic syndrome include: perindopril (Aceon®), quinapril (Accupril)®, ramipril (Altace®) and trandolapril (Mavik®)

Angiotensin II receptor blockers (ARBs). These medications help relax blood vessels by blocking the action, not the formation, of a natural chemical that narrows blood vessels. ARBs include candesartan (Atacand®), losartan (Cozaar®), losartan potassium-hydrochlorothiazide (Hyzaar®) and others. People with chronic kidney disease may benefit from having an ARB as one of their medications. Other examples of angiotensin II receptor blockers include azilsartan (Edarbi®), eprosartan, irbesartan (Avapro®), olmesartan (Benicar®, telmisartan (Micardis®) and valsartan (Diovan®)

Calcium channel blockers. These medications—including amlodipine (Norvasc®), diltiazem. (Cardizem®, Tiazac®, others) and others—help relax the muscles of your blood vessels. Some slow your heart rate. Calcium channel blockers may work better for black and older people than do ACE inhibitors alone.

Renin inhibitors. Aliskiren (Tekturna®) slows down the production of renin, an enzyme produced by your kidneys that starts a chain of chemical steps that increases blood pressure. Tekturna works by reducing the ability of renin to begin this process. Due to a risk of serious complications, including stroke, aliskiren cannot be taken without an ACE inhibitor or an ARB.

If the patient is having trouble reaching his/her blood pressure goal with combinations of the above medications, the doctor may prescribe:

Alpha blockers. These medications reduce nerve impulses to blood vessels, reducing the effects of natural chemicals that narrow blood vessels. Alpha blockers include doxazosin (Cardura®), prazosin (Minipress®) and others.

Alpha-beta blockers. In addition to reducing nerve impulses to blood vessels, alpha-beta blockers slow the heartbeat to reduce the amount of blood that must be pumped through the vessels. Alpha-beta blockers include carvedilol (Coreg®) and labetalol (Trandate®).

Central-acting agents. These medications prevent the brain from signaling the nervous system to increase the heart rate and narrow blood vessels. Examples include clonidine (Catapres®, Kapvay®), guanfacine (Intuniv®, Tenex®) and methyldopa.

Vasodilators. These medications, including hydralazine and minoxidil, work directly on the muscles in the walls of the arteries, preventing the muscles from tightening and the arteries from narrowing. Examples of vasodilators include NO-donors such nitroglycerine.

Aldosterone antagonists. Examples are spironolactone (Aldactone®) and eplerenone (Inspra®). These drugs block the effect of a natural chemical that can lead to salt and fluid retention, which can contribute to high blood pressure.

3. Anti-hyperlipidemic medications that may be used in combination with Compound I include, but are not limited to:

Statins. Examples of statins include, but are not limited to, atorvastatin (Lipitor®, Atorva®), fluvastatin (Lescol®, Canef®, Vastin®), lovastatin (Mevacor®), pitavastatin (Livalo®, Livazo®), pravastatin (Pravachol® or Selektine®), rosuvastatin (Crestor®) and simvastatin (Zocor®). Combinations of statins with another agent can be also be used. Examples include, but are not limited to, amlodipine/atorvastatin (Caduet®), aspirin/pravastatin (Praigard Pac®), ezetimibe/simvastatin (Vytorin®), niacin/simvastatin (Simcor®), lovastatin/niacin (Advicor®), simvastatin/sitagliptin (Juvisync®), and atorvastatin/ezetimibe (Liptruzet®).

Fibrates or fibric acid derivatives. Examples include, but are not limited to, fenofibrate (Antara®, Fenoglide®, Lipofen®, Lofibra®, TriCor®, Triglide®, Lipidil Micro®, Dom-Fenofibrate®, Lipidil Supra®, Lipidil EZ®), gemfibrozil (Lopid®), bezafibrate (Bezalip®), ciprofibrate, clinofibrate (Lipoclin®), and clofibrate (Atromid-S®)

Niacin (or nicotinic acid).

Bile acid sequestrants. Examples include, but are not limited to, cholestyramine (Prevalite®, Questran®, Questran Light®), is colesevelam (Welchol®), and colestipol (Colestid®).

Ezetimibe (Zetia®) is a selective inhibitor of dietary cholesterol absorption.

Lomitapide (Juxtapid®) is a microsomal triglyceride transfer protein (MTP) inhibitor.

Phytosterols may be found naturally in plants. Similar to ezetimibe, phytosterols reduce the absorption of cholesterol in the gut. Hence, they are most effective when consumed with meals.

Orlistat (Xenical®, Ali®). A drug designed to treat obesity. Its primary function is to prevent the absorption of fats from the human diet, thereby reducing caloric intake. It works by inhibiting pancreatic lipase, an enzyme that breaks down triglycerides in the intestine.

PCSK9 inhibitors. Examples include, but are not limited to, alirocumab (Praluent®), and evolocumab (Repatha®, Repatha Pushtronex®).

Therapeutic Methods

In one embodiment, the present invention provides a method of treating a human patient with metabolic syndrome comprising administering to said patient an oral daily dose of between 10 mg and 70 mg, between 10 mg and 60 mg, or between 10 mg and 50 mg of Compound I. In one embodiment, the method reduces the level of a metabolic marker selected from the group consisting of fasting blood glucose levels, fasting blood insulin levels, HbA1C levels, blood total cholesterol levels, blood LDL cholesterol levels, blood apolipoprotein B (ApoB) levels, blood triglyceride levels, HOMA-IR levels, ADMA concentrations in blood, blood ALT levels, blood AST levels, abdominal circumference and body weight, or of any combination of these markers thereof, in the patient. In another embodiment, the method reduces the fasting blood glucose level, the fasting blood insulin level, the HbA1C level, the blood total cholesterol level, the blood LDL cholesterol level, the blood ApoB level, the blood triglyceride level, the HOMA-IR value, the ADMA concentration in blood, the blood AST levels, the blood ALT levels, the abdominal circumference and the body weight of the patient. In another embodiment, the method increases insulin sensitivity in the patient. In certain embodiments, the patient is not given insulin during the treatment with Compound I, i.e., the patient is not administered with insulin in combination with Compound I. In other embodiments, the method improves endothelial function and reduces cardiovascular risk in the patient. In other embodiments, the method improves liver function in the patient. In some embodiments, the level of a metabolic marker in blood can be the level of the marker in plasma. In some embodiments, the level of a metabolic marker in blood can be the level of the marker in serum.

As used herein, when the level of a specific marker, such as fasting blood glucose levels, fasting blood insulin levels, HbA1C levels, blood cholesterol levels (total, HDL or LDL), blood ApoB level, blood triglyceride levels, abdominal circumference, body weight, ADMA blood concentrations, blood AST, ALT and GGT levels or HOMA-IR values, is reduced or increased by specified percentages or values, it means that the level of the marker after the treatment with Compound I is reduced or increased by the specified percentages or values as compared to the level of the marker before the treatment with Compound I (i.e., baseline level) for that patient.

In some embodiments, the level of a specific marker described above is the concentration of the specific marker in serum or plasma of the patient.

As used herein, when the level of a specified marker described above is reduced/decreased or increased "in the range of" two specified percentages or values, it means that the level is reduced or increased by a percentage or a value that is either between the two specified percentages or values or is equal to one of two specified percentages or values. For example, the term "in the range of N1 to N2" means a value that is greater or equal to N1 and less than or equal to N2, wherein N1 and N2 are the specified percentages or values.

As use herein, the term "between N1 and N2" means is greater or equal to N1 and less than or equal to N2, wherein N1 and N2 are the specified percentages or values, wherein N1 and N2 are two specified numbers.

In one embodiment, the present invention provides a method of reducing the level of fasting blood glucose in a human patient in need thereof comprising administering to the patient an oral daily dose of between 10 mg and 70 mg, between 10 mg and 60 mg, or between 10 mg and 50 mg of Compound I.

In certain embodiments, the level of the fasting blood glucose in the human patient treated with the methods of the present invention is reduced in the range of 1% to 40%, 2% to 40%, 5% to 40%, 5% to 30%, 5% to 25%, 5% to 15%, or 8% to 20%. In certain embodiments, the level of the fasting blood glucose is reduced more than 1%, more than 2%, more than 3%, more than 4%, more than 5%, more than 7%, more than 8%, more than 10%, more than 15%, more than 20%, or more than 25%.

In another embodiment, the present invention provides a method of reducing the level of fasting blood insulin in a human patient in need thereof comprising administering to said patient an oral daily dose of between 10 mg and 70 mg, between 10 mg and 60 mg, or between 10 mg and 50 mg of Compound I.

In certain embodiments, the level of fasting blood insulin in the human patient treated with the methods of the present invention is reduced in the range of 0.4 µIU/dL to 2.70 µIU/dL, wherein IU is international unit. In certain embodiments, the level of fasting blood insulin is reduced more than 0.1 µIU/dL, more than 0.2 µIU/dL, more than 0.3 µIU/dL, more than 0.4 µIU/dL, more than 0.5 µIU/dL, more than 1.0 µIU/dL, more than 1.5 µIU/dL, more than 2.0 µIU/dL, more than 2.5 µIU/dL, or more than 2.7 µIU/dL. In one embodiment, the human patient is not treated with insulin in combination with Compound I. In one embodiment, the human patient is treated with an oral antihyperglycemic in combination with Compound I.

In certain embodiments, the present invention provides a method of reducing the level of fasting blood insulin in a human patient in need thereof comprising administering to said patient an oral daily dose of between 10 mg and 70 mg, between 10 mg and 60 mg, or between 10 mg and 50 mg of Compound I, wherein the human patient is not administered with insulin in combination with Compound I. In one embodiment, the level of fasting blood insulin is reduced in the range of 5 pmol/L to 50 pmol/L, 5 pmol/L to 40 pmol/L, 5 pmol/L to 30 pmol/L, 10 pmol/L to 30 pmol/L, 10 pmol/L to 20 pmol/L, or 10 pmol/L to 15 pmol/L. In another embodiment, the level of fasting blood insulin is reduced more than 1 pmol/L, more than 5 pmol/L, or more than 10 pmol/L. In some of these embodiments, the patient is being treated with an oral antihyperglycemic in combination with Compound I.

In another embodiment, the present invention provides a method of reducing the level of HbA1C in a human patient in need thereof comprising administering to said patient an oral daily dose of between 10 mg and 70 mg, between 10 mg and 60 mg, or between 10 mg and 50 mg of Compound I.

In certain embodiments, the level of HbA1C in the human patient treated with the methods of the present invention is reduced in the range of 0.01% to 10%, 0.01% to 9%, 0.01% to 8%, 0.01% to 7%, 0.01% to 6%, 0.01% to 5%, 0.01% to 4%, 0.01% to 3%, 0.01% to 2%, 0.01% to 1.0%, 0.05% to 0.5%, 0.1% to 10%, 0.1% to 9%, 0.1% to 8%, 0.1% to 7%, 0.1% to 6%, 0.1% to 5%, 0.1% to 4%, 0.1% to 3%, 0.1% to 2%, 0.1% to 1%, 0.5% to 10%, 0.5% to 9%, 0.5% to 8%, 0.5% to 7%, 0.5% to 6%, 0.5% to 5%, 0.5% to 4%, 0.5% to 3%, 0.5% to 2%, 0.5% to 1%, 0.1% to 0.5%, 0.3% to 0.5%, 1% to 10%, 1% to 9%, 1% to 8%, 1% to 7%, 1 to 6%, or 1% to 5%. In certain embodiments, the level of HbA1C is reduced more than 0.01%, more than 0.02%, more than 0.03%, more than 0.04%, more than 0.05%, more than 0.1%, more than 0.2%, more than 0.3%, more than 0.4%, more than 0.5%, more than 1%, more than 2%, more than 3%, more than 4%, more than 5%, more than 6%, or more than 7%. The reduction in the level of HbA1C described above is the reduction in the actual reading of HbA1C, not the percentage reduction as compared to the HbA1C level in the patient before the treatment.

In another embodiment, the present invention provides a method of reducing the level of blood cholesterol in a human patient in need thereof comprising administering to said patient an oral daily dose of between 10 mg and 70 mg, between 10 mg and 60 mg, or between 10 mg and 50 mg of Compound I.

In certain embodiments, the level of blood cholesterol in the human patient treated with the methods of the present invention is reduced in the range of 10% to 40%, 10% to 30%, or 15% to 25%. In certain embodiments, the level of blood cholesterol is reduced more than 5%, more than 10%, more than 15%, more than 20%, or more than 25%.

In certain embodiments, the level of blood cholesterol in the method described above is the level of total cholesterol. In other embodiments, it is the level of blood LDL cholesterol.

In certain embodiments, the present invention provides a method of reducing the level of blood LDL cholesterol in a human patient in need thereof comprising administering to said patient a total oral daily dose of between 10 mg and 70 mg, between 10 mg and 60 mg, or between 10 mg and 50 mg of Compound I. In certain embodiment, the level of blood LDL cholesterol in the human patient treated with the methods of the present invention is reduced in the range of 10% to 40%, 10% to 30%, 10 to 20%, or 15% to 25%.

In certain embodiments, for the methods of reducing blood cholesterol or LDL cholesterol described above, there is no substantial decrease in the level of HDL cholesterol in the patients. In other embodiments there is an increase in the level of HDL cholesterol.

As used herein, "substantial decrease" for HDL refers to a decrease that is less than 10%, less than 5%, less than 4%, less than 3%, less than 2% or less than 1%.

In another embodiment, the present invention provides a method of reducing the level of blood apolipoprotein B (ApoB) in a human patient in need thereof comprising administering to said patient an oral daily dose of between 10 mg and 70 mg, between 10 mg and 60 mg, or between 10 mg and 50 mg of Compound I.

In certain embodiments, the level of ApoB in the human patient treated with the methods of the present invention is reduced in the range of 10% to 40%, 10% to 30%, 15% to 25% or 15% to 20%. In certain embodiments, the level of ApoB in the human patient treated with the methods of the present invention is reduced more than 5%, more than 10%, or more than 15%.

In another embodiment, the present invention provides a method of reducing the level of blood triglycerides in a human patient in need thereof comprising administering to said patient an oral daily dose of between 10 mg and 70 mg, between 10 mg and 60 mg, or between 10 mg and 50 mg of Compound I.

In certain embodiments, the level of blood triglyceride in the human patient treated with the methods of the present invention is reduced in the range of 5% to 30%, 5% to 20%, 5% to 15%, or 10% to 15%. In certain embodiments, the level of blood triglyceride is reduced more than 5%, more than 8%, more than 10% or more than 15%.

In another embodiment, the present invention provides a method of reducing the weight of a human patient in need thereof comprising administering to said patient an oral daily dose of between 10 mg and 70 mg, between 10 mg and 60 mg, or between 10 mg and 50 mg of Compound I.

In certain embodiments, the weight of the patient is reduced in the range of 1 kg to 50 kg, 1 kg to 30 kg, 1 kg to 20 kg, 5 kg to 20 kg, 5 kg to 10 kg, 1 kg to 10 kg, 1 kg to 8 kg, or 1.5 kg to 6 kg. In certain embodiments, the weight of the patient is reduced more than 0.5 kg, more than 1 kg, more than 1.5 kg, more than 2 kg, more than 2.5 kg, more than 3 kg, more than 4 kg, more than 5 kg, more than 6 kg, more than 10 kg, more than 15 kg, or more than 20 kg.

In certain embodiments, the abdominal circumference of the patient is reduced in the range of 1% to 15%, 1% to 10%, 1 to 8%, 1% to 5% or 5% to 10%. In certain embodiments, the abdominal circumference of the patient is reduced by more than 1%, more than 2%, more than 3%, more than 4%, more than 5%, more than 6%, more than 7%, more than 8%, more than 9%, or more than 10%, In another embodiment, the present invention provides a method of increasing insulin sensitivity in a human patient in need thereof comprising administering to said patient an oral daily dose of between 10 mg and 70 mg, between 10 mg and 60 mg, or between 10 mg and 50 mg of Compound I. In certain embodiments, the human patient has insulin resistance. "Insulin resistance" is a condition in which cells fail to respond normally to the hormone insulin.

As used herein, "insulin sensitivity" refers to how sensitive the body is to the effects of insulin. In certain embodiments, insulin sensitivity can be determined using homeostatic model assessment of insulin resistance (HOMA-IR), which is a method for assessing β-cell function and insulin resistance from basal (fasting) glucose and insulin or C-peptide concentrations. The normal HOMA-IR value for a healthy human ranges from 0.5 to 1.4. Less than 1.0 means the person is insulin-sensitive which is optimal. A value above 1.9 is indicative of early insulin resistance. A level above 2.9 is indicative of elevated insulin resistance.

In certain embodiments, the human patient is not administered with insulin in combination with Compound I. In some of these embodiments, the patient is being treated with an oral antihyperglycemic in combination with Compound I.

In certain embodiments, the HOMA-IR value in the patient treated with the methods of the present invention is reduced in the range of 10% to 60%, 10% to 50%, 15% to 45% or 20% to 30%. In certain embodiments, the HOMA-IR value in the patient treated with the methods of the present invention is reduced more than 5%, more than 10%, or more than 15%, more than 20%, more than 25%, more than 30%, or more than 35%.

In another embodiment, the present invention provides a method of improving endothelial function and reducing cardiovascular risk in a human patient in need thereof comprising administering to said patient an oral daily dose of between 10 mg and 70 mg, between 10 mg and 60 mg, or between 10 mg and 50 mg of Compound I.

In certain embodiments, the endothelial function can be measured by the decrerase in the concentration of asymmetric dimethylarginine (ADMA) in the patient's blood. In certain embodiments, the ADMA blood concentration in patients treated with the methods of the present invention is decreased in the range of 0.5 ng/mL to 50 ng/mL, 0.5 ng/mL to 20 ng/mL, 1 ng/mL to 20 ng/mL, 1 ng/mL to 15 ng/mL, 5 ng/mL to 20 ng/mL, 5 ng/mL to 15 ng/mL, or 5 ng/mL to 10 ng/mL. In certain embodiments, ADMA blood concentrations in patients treated with the methods of the present invention are decreased in the range of 1% to 50%, 1% to 30%, 1% to 20%, 1% to 15%, 1% to 10%, 1% to 5%, 5% to 30%, 5% to 20%, 5% to 15%, or 5% to 10%.

In another embodiment, the present invention provides a method of improving liver function in a human patient in need thereof comprising administering to said patient an oral daily dose of between 10 mg and 70 mg, between 10 mg and 60 mg, or between 10 mg and 50 mg of Compound I.

In certain embodiments, the improvement in liver function is determined by a decrease in blood levels of one or more liver enzymes. In certain embodimetns, the liver enzyme is alanine transaminase (ALT), aspartate transaminase (AST) or gamma-glutamyltransferase (GGT). In certain embodiment, blood levels of at least one of ALT. AST and GGT decrease in patients treated with the methods of the present invention. In certain embodiments, blood levels of ALT, AST and GGT decrease in patients treated with the methods of the present invention. In certain embodiment, the blood level of ALT in a patient treated with the methods of the present invention decreases in the range of 5% to 40%, 10% to 30%, or 15% to 25%. In certain embodiments, the blood level of AST in a patient treated with the methods of the present invention is decreased in the range of 5% to 40%, 10% to 30%, or 15% to 25%. In certain embodiments, the blood level of GGT in a patient treated with the methods of the present invention is decreased in the range of 1 U/L to 20 U/L, 1 U/L to 15 U/L, 1 U/L to 10 U/L, 1 U/L to 5 U/L, or 2 U/L to 3 U/L. In certain embodiments, the blood level of GGT in a patient treated with the methods of the present invention is decreased more than 1 U/L, more than 2 U/L, more than 3 U/L, more than 4 U/L, more than 5 U/L or more than 10 U/L. In certain embodiments, the blood level of GGT in a patient treated with the methods of the present invention is decreased in the range of 1% to 50%, 1% to 40%, 1% to 30%, 1% to 20%, 1% to 15%, 1% to 10%, 1% to 5%, 5% to 30%, 5% to 20%, 5% to 15% or 5% to 10%.

In certain embodiments, for the methods of the present invention described herein, the human patient has metabolic syndrome.

In certain embodiments, the methods of the present invention described herein comprise administering to the patient a single oral daily dose of between 10 mg and 70 mg, between 10 mg and 60 mg, or between 10 mg and 50 mg of Compound I.

In certain embodiments, the methods of the present invention described herein comprise administering to the patient a single oral daily dose of 10 mg of Compound I.

In certain embodiments, the methods of the present invention described herein comprise administering to the patient a single oral daily dose of 20 mg of Compound I.

In certain embodiments, the methods of the present invention described herein comprise administering to the patient a single oral daily dose of 30 mg of Compound I.

In certain embodiments, the methods of the present invention described herein comprise administering to the patient a single oral daily dose of 40 mg of Compound I.

In certain embodiments, the methods of the present invention described herein comprise administering to the patient a single oral daily dose of 50 mg of Compound I.

In certain embodiments, the methods of the present invention described herein comprise administering to the patient a single oral daily dose of 60 mg of Compound I.

In certain embodiments, the methods of the present invention described herein comprise administering to the patient a single oral daily dose of 70 mg of Compound I.

In certain embodiments, the methods of the present invention described herein comprise administering to the patient an oral dose of 20 mg of Compound I twice a day. In one embodiment, the method comprises administering to the patient a first oral dose of 20 mg and a second oral dose of 20 mg, wherein the first dose and the second dose are separated by a period between 5 hours and 15 hours, between 8 hours and 15 hours, or between 10 hour and 15 hours. In another embodiment, the first dose and the second dose are separated by 5 hours, 6 hours, 7 hours, 8 hours, 9 hours, 10 hours, 11 hours, 12 hours, 13 hours, 14 hours, or 15 hours.

In certain embodiments, the methods of the present invention described herein further comprise administering to the patient one or more (two, three, four, five, etc.) anti-hypertensive medications. In one embodiment, the one or more anti-hypertensive medications are each independently selected from an angiotensin-converting enzyme (ACE) inhibitor and an angiotensin H receptor blocker (ARB). In another embodiment, the one or more anti-hypertensive medication is independently selected from the group consisting of lisinopril, combinations of lisinopril with hydrochlorothiazide, benazepril, captopril, enalapril, candesartan, losartan, azilsartan, eprosartan, irbesartan, olmesartan, telmisartan and valsartan. In another embodiment, the one or more anti-hypertensive medications are each independently selected from the group consisting of lisinopril, combination of lisinopril and hydrochlorothiazide, enalapril, losartan, metoprolol, and spironolactone. In another embodiment, the one or more anti-hypertensive medications are each independently selected from the group consisting lisinopril, combination of lisinopril and hydrochlorothiazide, enalapril, losartan, metoprolol, and spironolactone. In another embodiment, the one or more anti-hypertensive medications are each independently selected from the group consisting of lisinopril, combination of lisinopril and hydrochlorothiazide, enalapril, and losartan. In one embodiment, at least one of the anti-hypertensive medication is an angiotensin-converting enzyme (ACE) inhibitor or an angiotensin II receptor blocker (ARB). In another embodiment, at least one of the anti-hypertensive medication is selected from the group consisting of lisinopril, combination of lisinopril and hydrochlorothiazide, enalapril, and losartan.

In certain embodiments, the methods of the present invention described herein further comprise administering to the patient one or more (two, three, four, five, etc.) blood glucose lowering medications (anti hyperglycemic or antidiabetes drugs). In one embodiment, the one or more blood glucose lowering medications are independently selected from the group consisting of insulin, metformin, glyburide, glipizide, glimepiride, repaglinide, nateglinide, sitagliptin, saxagliptin, linagliptin, exenatide, liraglutide, canagliflozin, and dapagliflozin. In certain embodiment, insulin is not given or administered to the patient treated with the methods described herein during the treatment with Compound I. In some embodiments, the patient is being treated with an oral antihyperglycemic agent in addition to Compound I.

In certain embodiments, the methods of the present invention described herein further comprise administering to the patient an anti-hypertensive medication described herein and a blood glucose lowering medication described herein. In one embodiment, the method further comprises administering to the patient one or more anti-hypertensive medications independently selected from the group consisting of isinopril, combination of lisinopril and hydrochlorothiazide, enalapril, losartan, metoprolol, and spironolactone and one or more blood glucose lowering medications independently selected from the group consisting of insulin, metformin, and glipizide. In one embodiment, at least one of the anti-hypertensive medication is an angiotensin-converting enzyme (ACE) inhibitor or an angiotensin II receptor blocker (ARB). In another embodiment, at least one of the anti-hypertensive medication is selected from the group consisting of lisinopril, combination of lisinopril and hydrochlorothiazide, enalapril, and losartan.

In certain embodiments, the methods of the present invention described herein further comprise administering to the patient one or more (two, three, four, five, etc.) anti-hyperlipidemic medications. In one embodiment, the one or more anti-hyperlipidemic medications is selected from a cholesterol lowering medication. In one embodiment, the one or more anti-hyperlipidemic medications are independently selected from the group consisting of atorvastin, pravastatin, simvastatin, rosuvastatin, lovastatin and nicotinic acid. In another embodiment, the one or more cholesterol lowering medication is selected from the group consisting of atorvastin, pravastatin, rosuvastatin, lovastatin and simvastatin.

In certain embodiments, the patient can be treated with Compound I alone or in combination with the additional therapeutic agent for 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 6 months, 1 year, 2 years, etc.

EXAMPLES

For this invention to be better understood, the following examples are set forth. These examples are for purposes of illustration only and are not be construed as limiting the scope of the invention in any manner. All references provided in the Examples are herein incorporated by reference.

Example 1: Evaluation of Compound I in ZSF1 Rats (Animal Model of Diabetic Nephropathy)

This study evaluated blood pressure, renal function, end-organ protection and metabolic markers in ZSF1 rats treated with Compound I alone or enalapril alone or Compound I in combination with enalapril. Enalapril is sold under the brand name Vasotec among others, and is a medication used to treat high blood pressure, diabetic kidney disease, and heart failure.

The ZSF1 rat model exhibits many features of human diabetic kidney disease including, among others, hyperglycemia (elevated blood glucose), dyslipidemia, obesity, mild hypertension and oxidative stress, which are also characteristic of metabolic syndrome.

Test Materials

| Compounds: | Compound I and enalapril (enalapril Maleate, E6888, Sigma Aldrich) |
|---|---|
| Dosing Route: | Diet admix |
| Formulation and Dosage: | Diet admix formulated by Research Diet, Inc. Compound I at 1 mg/kg/day: Purina 5008 rodent chow with 8.3 mg of Compund I/kg of chow. Compound I at 3 mg/kg/day: Purina 5008 rodent chow with 25 mg of Compound I/kg of chow. Compound I at 10 mg/kg/day: Purina 5008 rodent chow with 83 mg of Compound I/kg of chow enalapril 3 mg/kg/day: in drinking water |
| | Vehicle: Purina 5008 rodent chow. |

Animals:
Species/Strain: ZSF1 lean and obese rats
Initial Body Weight: 400-430 grams (lean control) and 500-605 grams (obese) at baseline
Sex: Male
Vendor: Charles River Laboratories
Experimental Design:
Dosing Groups:
  1. ZSF1 Lean—Vehicle (n=6)
  2. ZSF1 Obese—Vehicle (n=9)
  3. ZSF1 Obese—enalapril 3 mg/kg/day (n=9)
  4. ZSF1 Obese—Compound I 1 mg/kg/day (n=9)
  5. ZSF1 Obese—Compound I 3 mg/kg/day (n=9)
  6. ZSF1 Obese—Compound I 10 mg/kg/day (n=9)
  7. ZSF1 Obese—enalapril 3 mg/kg+Compound I 1 mg/kg/day (n=9)
  8. ZSF1 Obese—enalapril 3 mg/kg+Compound I 3 mg/kg/day (n=9)
  9. ZSF1 Obese—enalapril 3 mg/kg+Compound I 10 mg/kg/day (n=9)
Procedure:

Male ZSF1 rats (body weight 400-430 grams (lean control) and 500-605 grams (obese) at baseline) were used for this study. All animals were housed in a room under controlled conditions of temperature (72±8° F.), relative humidity of 30-70% and a 12-hour light-dark cycle (lights on at 6:00 AM and off at 6:00 PM) at a fully AAALAC accredited, USDA registered and OLAW assured laboratory animal research facility. All animals were allowed free access to rodent chow (Purina 5008+/−test articles) and water (+/− enalapril).

Telemetry System and Transmitter Implantation

This study employed the Dataquest A.R.T.™ acquisition and analysis system (Data Sciences International, St. Paul, Minn.) to monitor and analyze hemodynamic data from conscious, freely moving rats with a surgically implanted radio-telemetry pressure transmitter (HD-S10).

Telemetry transmitter implantations were performed on ZSF1 lean and obese rats at 9-10 weeks of age under sterile conditions. Briefly, animals were anesthetized with isoflurane and body temperature was maintained with a heating pad during surgery. A laparotomy was performed to expose the abdominal aorta and the catheter tip of the telemetry transmitter was inserted into the abdominal aorta, secured with a 5-0 silk suture and the body of the telemetry transmitter was placed in the abdominal cavity and secured to the abdominal wall. The abdominal incision was then closed with uninterrupted suture (4-0 silk, Ethicon, Inc.). Approximately 100 μL of 0.25% marcaine was applied directly to the closed abdominal wall, and the skin was closed with a 4-0 Vicryl synthetic absorbable suture (Ethicon, Inc.). Long acting Buprenorphine (1 mg/kg/day, SC) was administered immediately after the surgery for postoperative pain relief. After recovered from anesthesia, rats were returned to their home cages placed on DSI radio signal receivers.

Treatment and Sample Collections

Blood and 24-hour urine samples were obtained from all animals at day 0 (15 weeks of age; prior to the initiation of enalapril treatment). Animals in Groups 3, 7, 8 and 9 were placed on drinking water containing enalapril and kept on Purina 5008 rodent chow (C13000). Animals in Group 1, 2, 4, 5 and 6 were kept on Purina 5008 rodent chow and drinking water. Ten days after the initiation of enalapril treatment, blood and 24-hour urine samples were collected from all animals. After day 10 blood and urine collections, animals in Groups 4, 5 and 6 received Compound I at 1, 3 and 10 mg/kg/day, respectively for 11 weeks. In addition to enalapril treatment, animals in Groups 7, 8 and 9 received Compound I at 1, 3 and 10 mg/kg/day, respectively for an additional 11 weeks.

At weeks 5 and 9, blood and 24-hour urine samples were collected from all animals. Plasma samples were obtained from animals in Groups 3-9 for the measurement of compound exposure levels at week 5 (8:00 AM and 4:00 PM) and week 11 (8:00 AM).

Body weight and 24-hour water intake were obtained at least once every other week. 24-hour food intake was measured at baseline and week 8.

Oral Glucose Tolerance Test (OGTT), Fasting Glucose and Fasting Insulin 10 weeks after the initiation of Compound I treatment, animals (27 weeks of age) were fasted for 18 hours. Serum samples were collected for the measurement of fasting insulin levels. Serum insulin levels were determined using the Rat Insulin ELISA kit (Cat #ELR-Insulin, RayBiotech, Inc.)

For OGTT, animals were given glucose solution (50% Dextrose) at 2 g/kg via oral gavage. Blood samples were collected prior to oral glucose administration (0 minute) and 30, 60, 90, 120 and 180 minutes after administration. Blood glucose levels were measured using a standard blood glucose monitoring system (AlphaTRAK). The blood glucose reading at time 0 (prior to glucose administration) corresponds to the fasting glucose measurement.

Blood Sample Process

Plasma (for biomarker) and serum (for clinical chemistry analysis) samples were collected from all treatment groups at baseline, day 10, weeks 5 and 9 prior to placing the animals into the metabolic cages. Plasma samples were obtained from Groups 3-9 for measurement of compound exposure levels at weeks 5 and 11. Terminal plasma and serum samples were obtained at necropsy.

For serum samples, blood was collected in serum separator tubes, maintained at room temperature for at least 30 minutes and then centrifuged at 6000 rpm for 10 minutes. Serum samples were stored at −80° C. until analysis. Urine and serum samples were analyzed using the Randox Daytona Clinical Chemistry Analyzer. All measurements were performed in accordance with manufacturer's instructions.

For plasma samples, blood was collected in plasma separator tubes containing EDTA, followed by centrifugation at 3500 rpm for 10 minutes at 4° C. The supernatants were then transferred into Eppendorf tubes. Terminal plasma samples were transferred into the Eppendorf tubes and the Eppendorf tubes pre-loaded with 5 μL of 100 mM IBMX (500 μL plasma). Plasma samples were stored at −80° C.

Figure 16:
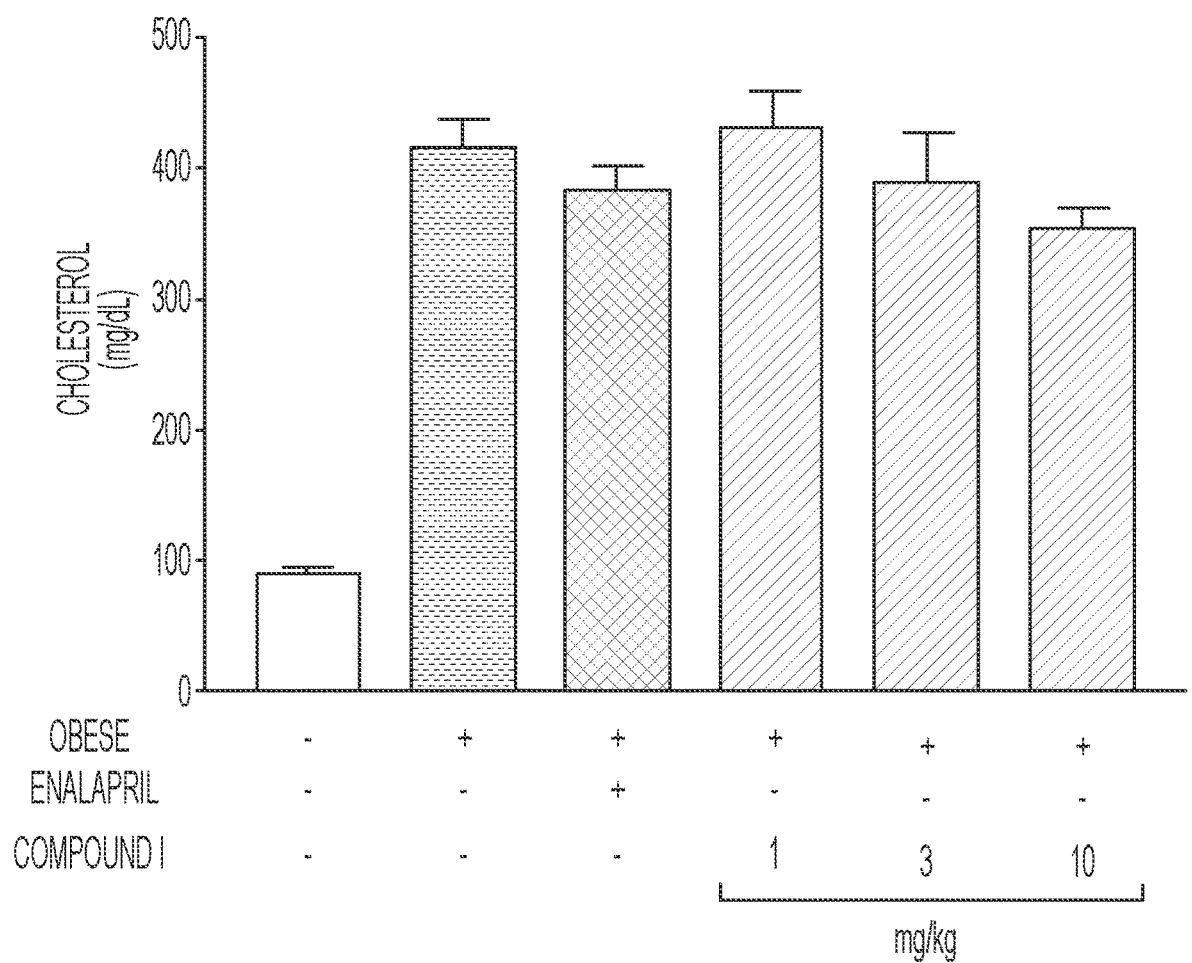
FIG. 16 shows reduction of cholesterol levels upon treatment with Compound I or enalapril in the obese ZSF1 Rat Model (Example 1).

FIG. 16 shows the effect of treatment with Compound I on cholesterol levels. Although some reduction in cholesterol was observed upon treatment compared to placebo and enalapril treatment for the higher dosages of 3 and 10 mg/kg, the results were not statistically significant.

Figure 17:
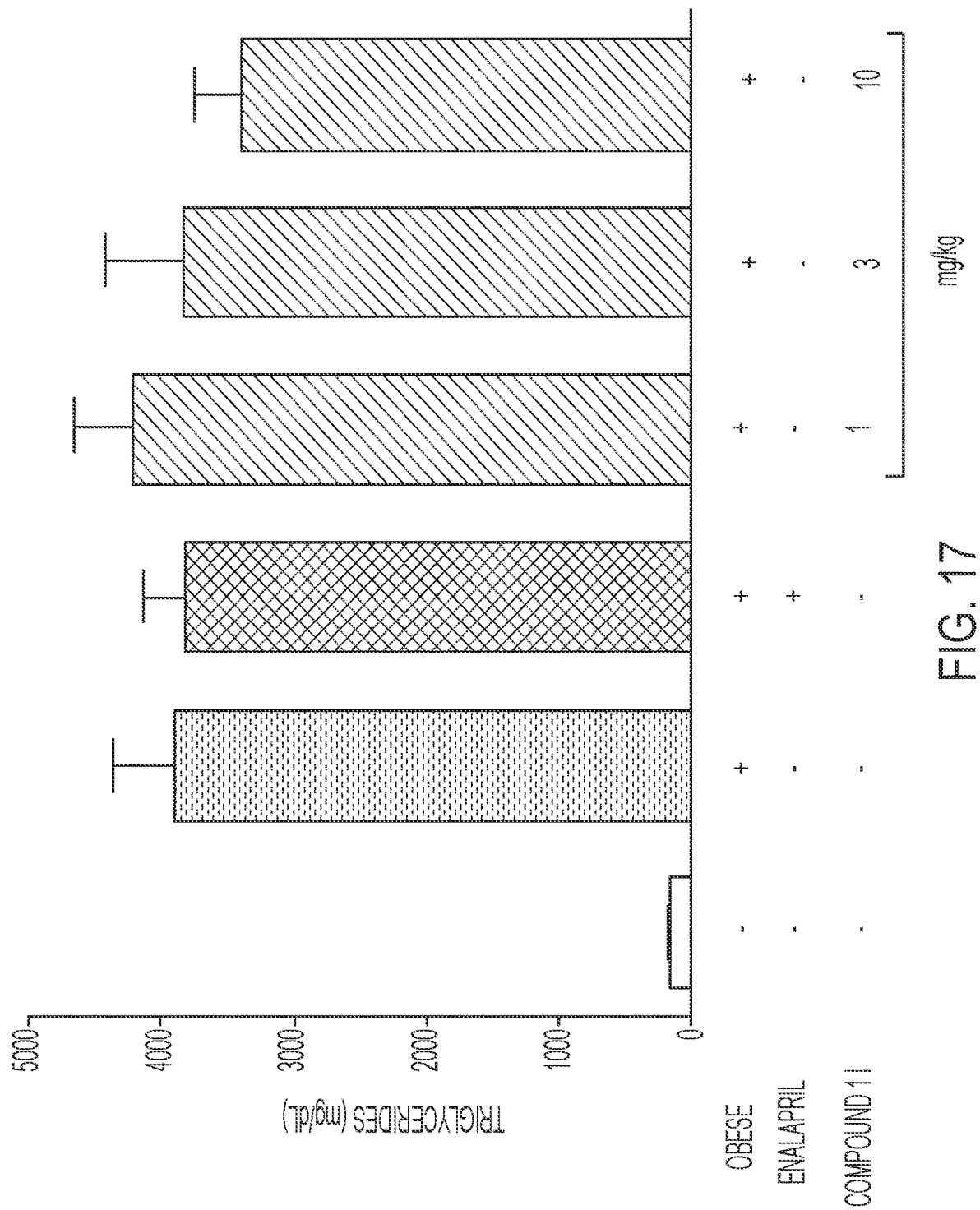
FIG. 17 shows reduction of triglyceride levels upon treatment with Compound I or enalapril in the obese ZSF1 Rat Model (Example 1).

FIG. 17 shows the effect of treatment with Compound I on triglyceride levels. Although some reduction in TGs was observed upon treatment compared to placebo and enalapril treatment for the higher dosages of 3 and 10 mg/kg, the results were not statistically significant.

No effects were observed on the reduction of weight.

Data Analysis

The data are expressed as mean±SEM. Clinical chemistry data, blood glucose levels (0, 120 and 180 minutes) during the oral glucose tolerance test (OGTT), OGTT AUC, fasting insulin levels, and 24 hours water intake and food intake were analyzed by one-way analysis of variance (ANOVA), followed by Fisher's Least Significant Difference (LSD) for the comparison of means using GraphPad Prism (version 7) software. One-tailed tests were used for comparison of variables. Statistical significance is indicated by P values less than 0.05.

Figure 2:
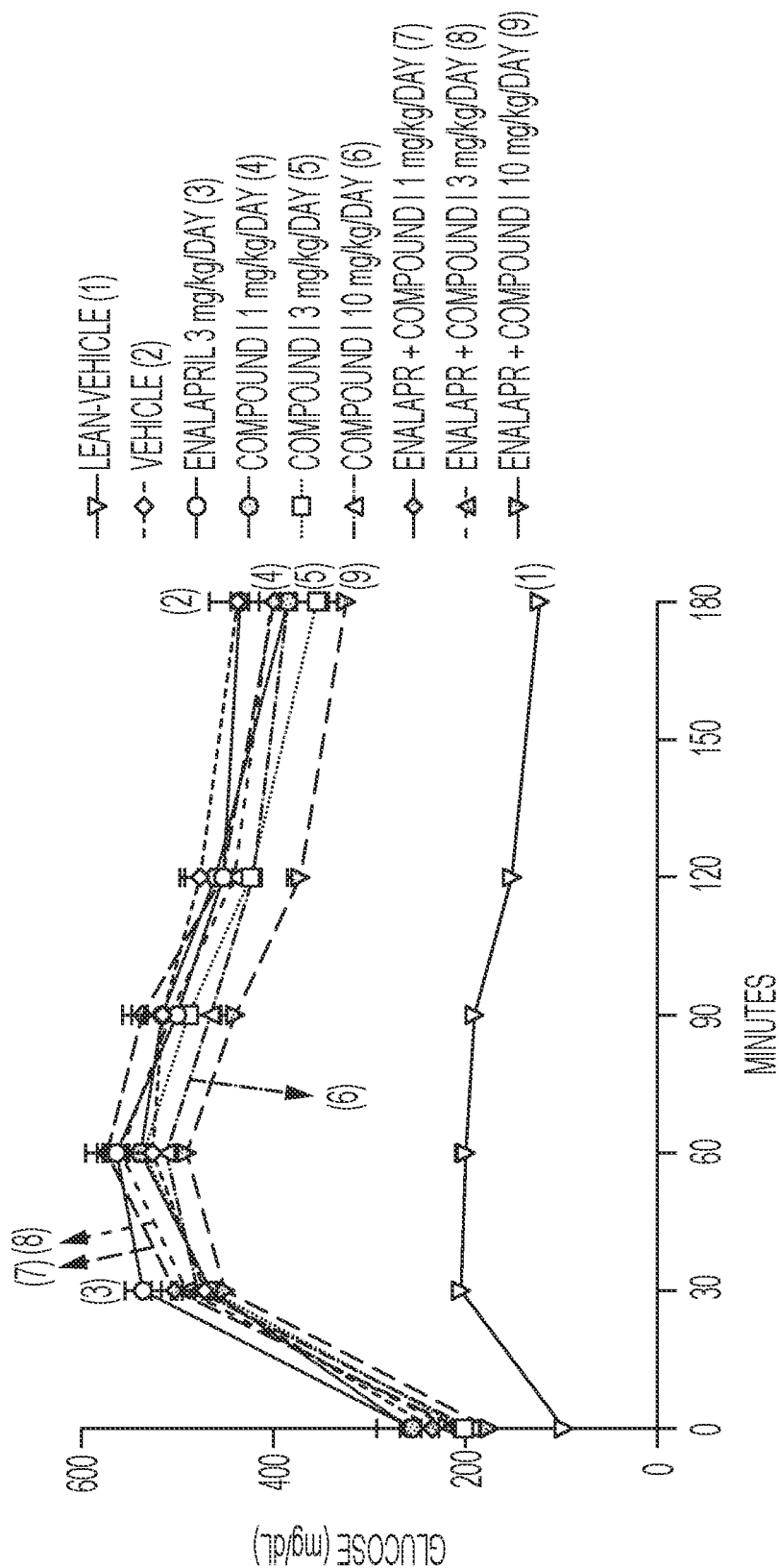
FIG. 2 shows the results of the oral glucose tolerance test (OGTT) at week 10 upon treatment with Compound I alone, enalapril alone or Compound I combined with enalapril in the obese ZSF1 rat model (Example 1).

Results:

Fasting blood glucose, blood glucose levels at 120 and 180 minutes after oral glucose administration, OGTT AUC, and fasting insulin levels are summarized in Table 1 below. Fasting blood glucose levels upon treatment with enalapril or Compund I are shown in FIG. 1. Blood glucose levels during OGTT are shown in FIG. 2.

TABLE 1

Oral Glucose Tolerance Test and Fasting Insulin at Week 10

| | Oral Glucose Tolerance Test (OGTT) | | | | |
|---|---|---|---|---|---|
| | Blood Glucose (mg/dL) | | | | |
| Group | Fasting Blood Glucose (0 minute) | 120 minutes | 180 minutes | Area Under Curve (AUC) | Fasting Insulin (μIU/mL) |
| Lean – Vehicle (n = 6) | 98 ± 2 | 152 ± 5* | 123 ± 4* | 29828 ± 991 | BLLQ |
| ZSF1 – Vehicle (n = 8) | 239 ± 12* | 485 ± 22* | 453 ± 29* | 85262 ± 4043* | 13.9 ± 2.3 |

TABLE 1-continued

Oral Glucose Tolerance Test and Fasting Insulin at Week 10

| | Oral Glucose Tolerance Test (OGTT) | | | | Fasting Insulin (μIU/mL) |
|---|---|---|---|---|---|
| | Blood Glucose (mg/dL) | | | | |
| Group | Fasting Blood Glucose (0 minute) | 120 minutes | 180 minutes | Area Under Curve (AUC) | |
| ZSF1 – Enaplapril 3 mpk (n = 8) | 255 ± 13* | 452 ± 10* | 435 ± 9* | 84459 ± 1409* | 11.4 ± 1.7 |
| ZSF1 – Compound I 1 mpk (n = 8) | 267 ± 38* | 475 ± 33* | 398 ± 30* | 84945 ± 5344* | 15.7 ± 3.5 |
| ZSF1 – Compound I 3 mpk (n = 9) | 202 ± 10* | 424 ± 19*# | 355 ± 24*# | 77402 ± 3526* | 15.6 ± 2.7 |
| ZSF1 – Compound I 10 mpk (n = 9) | 194 ± 9*# | 421 ± 11*# | 385 ± 14*# | 77090 ± 1817* | 11.7 ± 1.6 |
| ZSF1 – Enalapril + Compound I 1 mpk (n = 9) | 206 ± 6* | 453 ± 25 | 399 ± 27* | 83825 ± 3632* | 17.3 ± 2.4 |
| ZSF1 – Enalapril + Compound I 3 mpk (n = 9) | 215 ± 13* | 441 ± 25 | 402 ± 31* | 81783 ± 3825* | 14.9 ± 1.1 |
| ZSF1 – Enalapril + Compound I 10 mpk (n = 9) | 175 ± 9*# | 372 ± 13*# | 324 ± 18*# | 70523 ± 2579*# | 13.5 ± 1.9 |

Data represented as mean ± SEM;
*p < 0.05 vs. Lean – Vehicle,
p < 0.05 vs. ZSF1 – Vehicle;
BLLQ, below the Lower Limit of Quantification.

Clinical Observations:

Animal #8 (in Group 3, ZSF1—enalapril 3 mg/kg/day) was found dead 3 days after the initiation of enalapril treatment. Animals #29 (in Group 2, ZSF1—Vehicle) and 73 (in Group 4, ZSF1-IW-1973 1 mg/kg/day) had enlarged left kidney's filled with brown fluid consistent with hydronephrosis and were not included in the summary dataset.

Example 2: Evaluation of Compound I in the Diet Induced Obesity Mouse Model (DIO) (Model of Obesity and Insulin Resistance)

The objective of this animal study was to evaluate the effects of Compound I in the mouse diet induced obesity (DIO) model. Assessments included body weight, food intake, oral glucose tolerance test (OGTT) and fasting plasma biomarkers of metabolic control. This model exhibits many features of human metabolic syndrome, among others, hyperglycemia (elevated blood glucose), dyslipidemia, insulin resistance, obesity, and oxidative stress. The mouse DIO model is a widely used model of insulin and leptin resistance that has previously been used to demonstrate the metabolic effects of an sGC stimulator (Hoffmann L S, Etzrodt J, Willkomm L, et al. Stimulation of soluble guanylyl cyclase protects against obesity by recruiting brown adipose tissue. *Nature Communications.* 2015; 6:7235).

Methods:

Male C57Bl/6J mice with baseline body weights of 25.0-29.0 grams (lean controls) and 31.5-45.0 grams (obese/high fat diet treated) respectively, were used for this study. The lean mice (n=8) were maintained on a standard chow diet. The obese mice were given 60% high fat diet (HFD) starting at 6 weeks of age. All animals were allowed free access to drinking water and chow. The study was begun when the mice were 12 weeks of age and concluded after 4 weeks (16 weeks of age). The obese control group (n=8 mice) was maintained on HFD. The Compound I group (n=8 obese mice) was treated with HFD containing 90 mg Compound I/kg (an approximate dose of 6 mg/kg). Body weights were determined twice weekly and food intake was measured daily for 28 days. An OGTT was performed on each animal at day 28 or 29 and the animals were sacrificed on the following day. On the terminal day, 3 hour fasted blood was collected for compound concentrations and plasma biomarkers analysis including glucose, insulin and triglycerides. Organs were collected, weighed and snap frozen in liquid nitrogen for further analysis.

Figure 6:
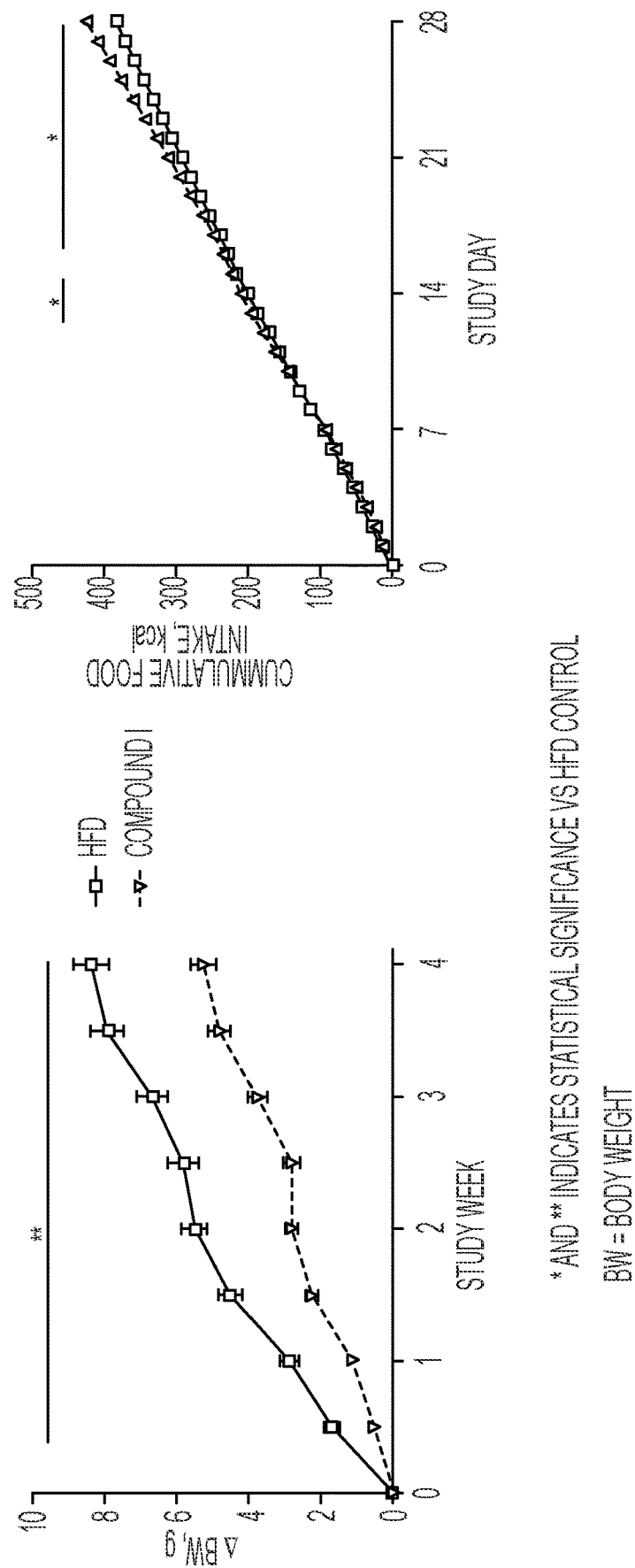
FIG. 6 shows treatment with Compound I attenuates weight gain while caloric intake modestly increases in the DIO HFD Mouse model (Example 2).

Results:

Effects on Body Weight and Food Intake:

Compound I produced significant reductions in body weight gain starting at 0.5 weeks and continuing for the duration of the study when compared to the obese controls. At Day 28, Compound I reduced body weight gain by −37% (P<0.0001). Significant increases in cumulative food intake were observed with Compound I treatment compared to obese controls at days 12-14 and 16-28. At Day 28, Compound I promoted a modest 11% increase in food intake (P<0.05). These results are summarized in FIG. 6.

Figure 3:
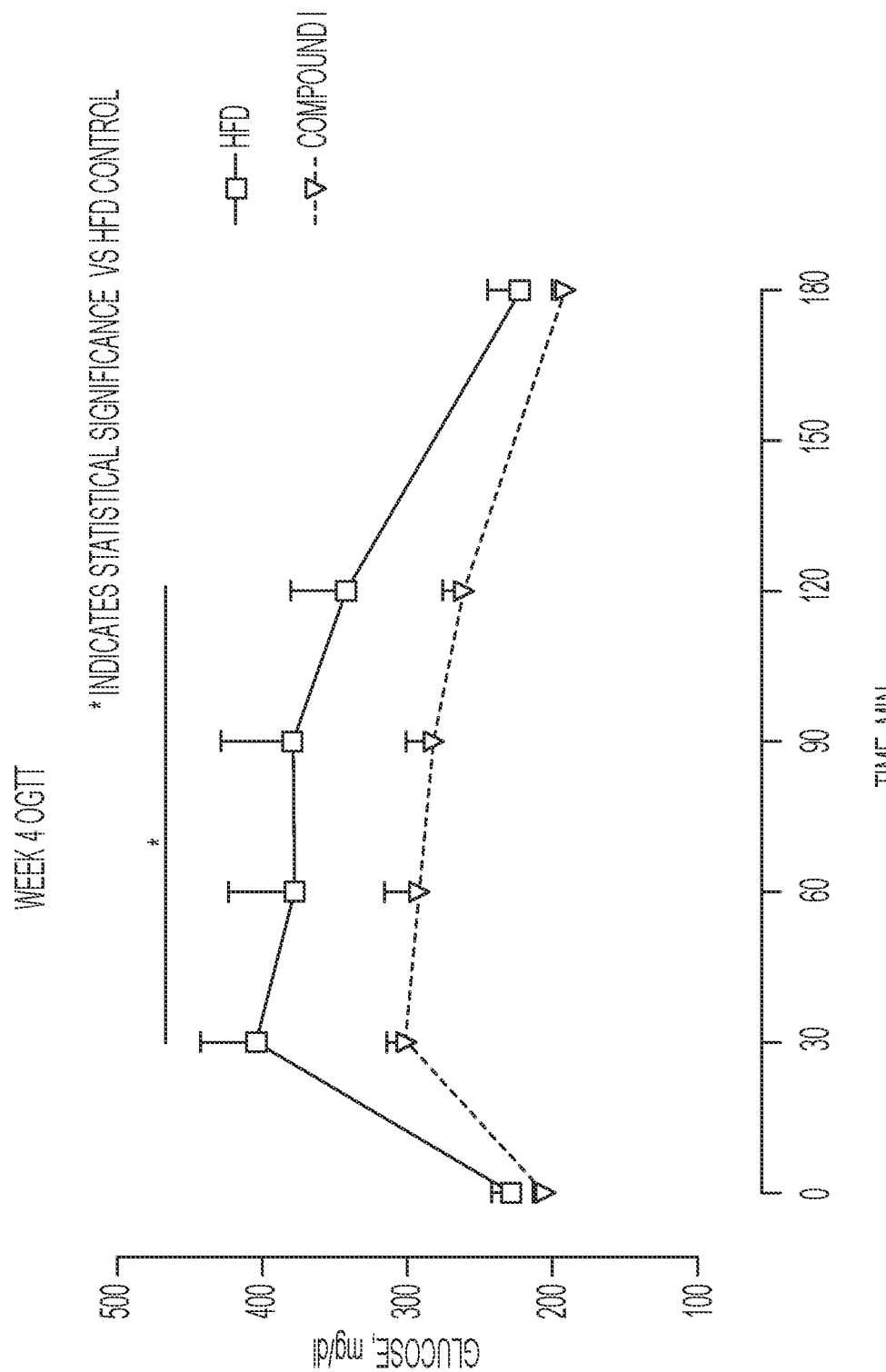
FIG. 3 shows the results of the Oral Glucose Tolerance Test (OGTT) at week 4 upon treatment with Compound I in the DIO high fat diet (HFD) Mouse model (Example 2).

Effects on Glucose Tolerance:

Compound I treatment produced significant reductions in blood glucose excursion from 30 to 120 minutes as assessed by an oral glucose tolerance test (OGTT) compared to obese controls. Compound I treatment also significantly decreased OGTT area under the curve (−22%, P<0.05) and area above baseline (−47%, P<0.05). Fasting blood glucose was not reduced by Compound I in this animal model. These results are summarized in FIG. 3.

Figure 4:
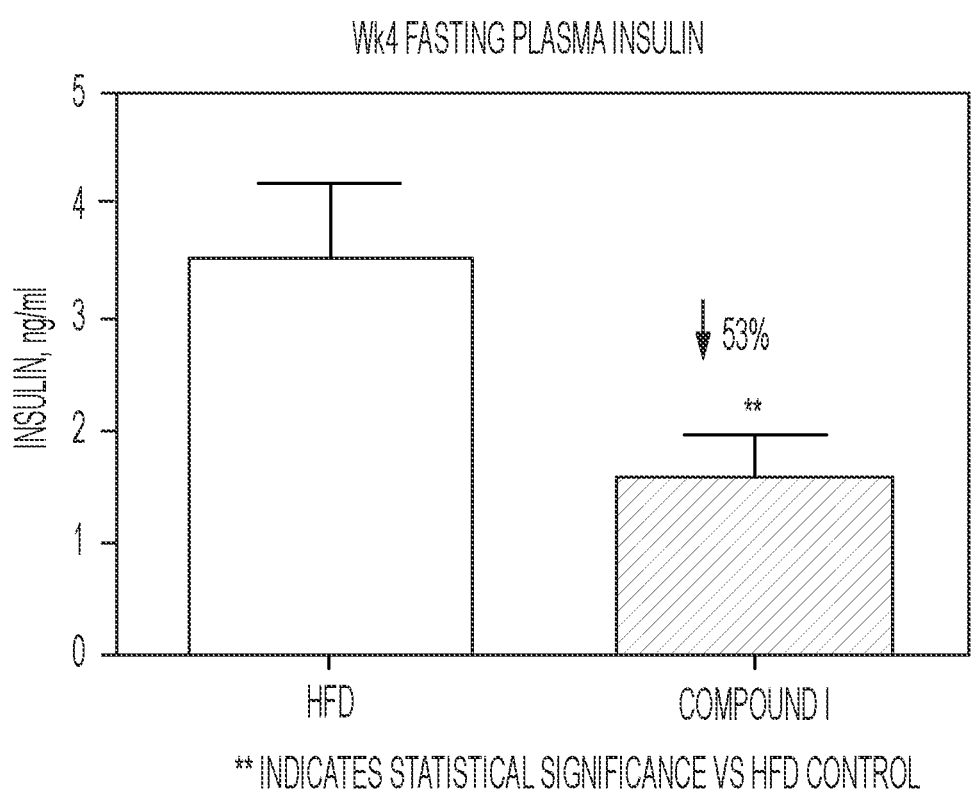
FIG. 4 shows the effect of 4 weeks treatment with Compound I on fasting plasma insulin in the DIO HFD Mouse model (Example 2).
Figure 5:
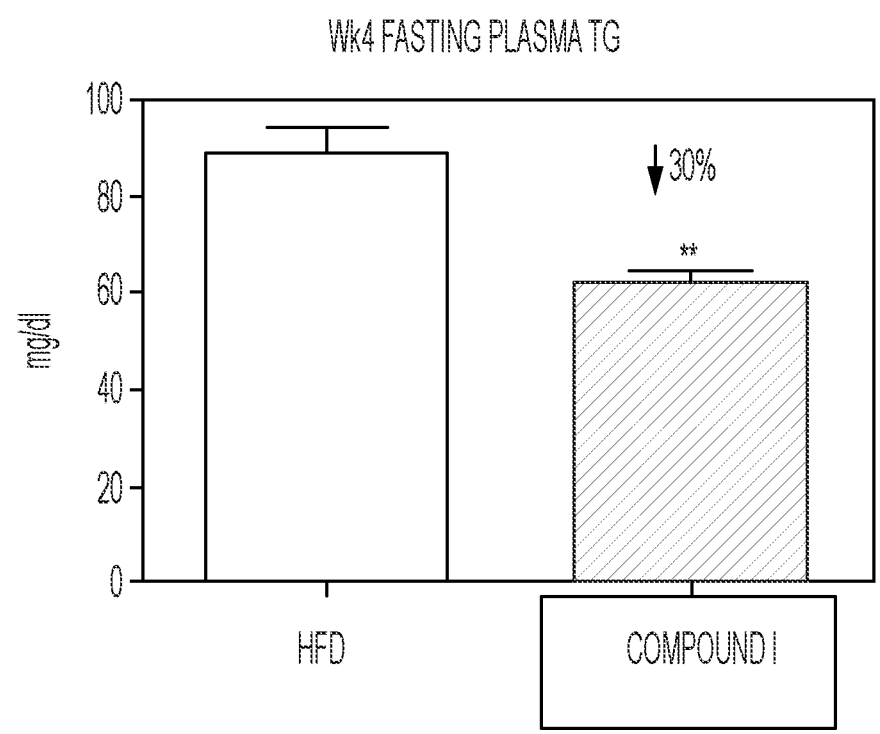
FIG. 5 shows the effects of 4 weeks of treatment with Compound I on fasting plasma triglyceride (TG) levels in the DIO HFD Mouse model (Example 2).

Effects on Plasma Biomarkers:

After 4 weeks Compound I treatment reduced plasma insulin (−53%, P<0.01) and plasma triglycerides (−30%, P<0.01) when compared to obese controls. Fasting plasma glucose was unchanged by Compound I treatment. These results are summarized in FIGS. 4 and 5.

Conclusions

In the mouse DIO model of obesity and insulin resistance, compared to obese controls statistically significant changes were observed in the following parameters. Compound I reduced body weight gain while promoting a modest increase in food intake. Compound I improved glucose tolerance as evidenced by reductions in blood glucose levels during the OGTT time course, area under the curve and area above baseline, although fasting glucose levels were unchanged. Compound I reduced plasma insulin. Compound I lowered circulating and liver triglycerides. These improvements suggested that Compound I may promote a more favorable metabolic profile in other animals, including humans.

Example 3: An Open-Label, Phase 2a Trial to Evaluate the Effect of Escalating Doses of Compound I on Tolerability, Endothelial Function, and Hemodynamics in Patients with Stable Type 2 Diabetes and Hypertension The primary objectives of this clinical study (ClinicalTrials.gov Identifier: NCT02906579) were to assess the acute effects of escalating doses of Compound I on endothelial function (using EndoPAT™—Itamar Medical; Caesarea, Israel- to measure fingertip small vessel pulse volume), blood pressure, heart rate/pulse, safety and tolerability in patients with Type 2 diabetes and a history of hypertension. Patients in this trial were on stable medications for glucose control (blood glucose lowering medication) and hypertension (including an ARB or an ACEi). Secondary measurements included assessment of fasting glucose levels, fasting insulin levels, hemoglobin A1C (HbA1C) levels, serum cholesterol levels, serum triglyceride levels, BMI and body weight.

Study Design:

Allocation: non-randomized; Intervention Model: single group assignment; Masking: non (open-label), Primary purpose: treatment. Single cohort of 11 patients confined to unit. Single clinical site.

The 11 patients were enrolled separately. Each patient progressed through 3 study periods:

Screening Period: The Screening Period began with the signature of the informed consent form (ICF) at the Screening Visit and lasted 1 to 26 days. Patients underwent preliminary screening procedures to determine their eligibility for the study at the Screening Visit. The end of the Screening Period coincided with the beginning of the Clinic Period at Check-in.

Figure 29:
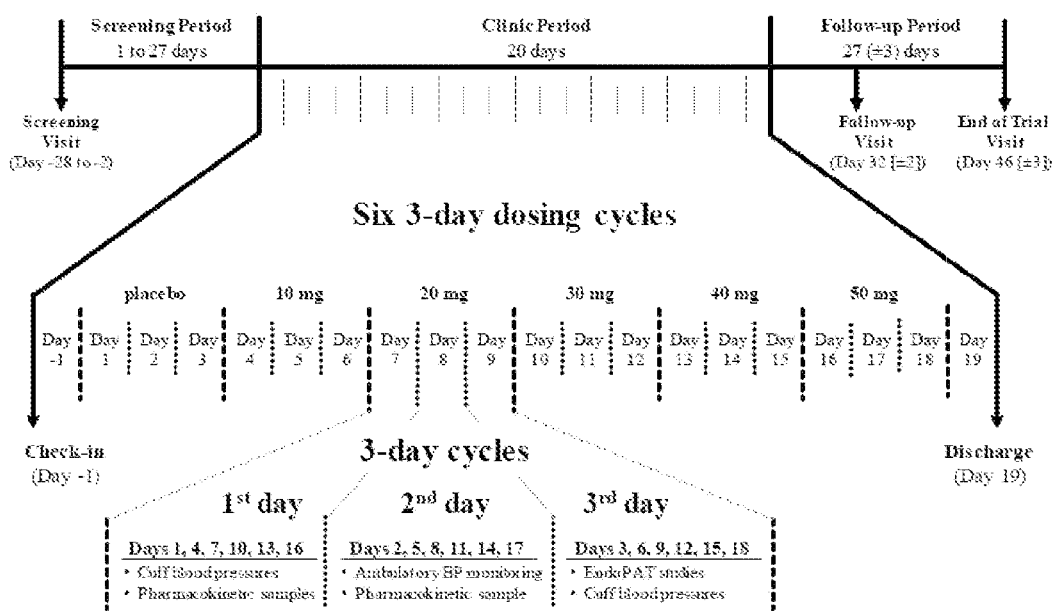
FIG. 29 shows a study schematic diagram of an open-label, Phase 2a trial to evaluate the effect of escalating doses of Compound I on tolerability, endothelial function, and hemodynamics in patients with stable type 2 diabetes and hypertension.

Clinic Period: The Clinic Period began at Check-in on Day-1 and ended at Discharge on Day 19. Patients who met eligibility criteria based on Screening Visit assessments were admitted to the Study Center on Day-1 for procedures to confirm eligibility and were confined to the Study Center until Discharge on Day 19. Patients received a standard diet for diabetics. On Days 1 to 18, following an overnight fast of ≥8 hours, eligible patients received once-daily study drug. Safety (adverse event [AE] collection, vital signs, fasting glucose, serum insulin, electro cardiograms [ECGs]) and pharmacokinetic (PK) assessments, including blood collections, were performed at pre-specified times daily (see Schedule of Events). Pharmacodynamic assessments was performed on a 3-day cycle that repeated for each of the 6 dosing cycles (see FIG. 29 and Schedule of Events): the first day included supine and standing cuff BP and pulse measurements; the second day include ambulatory BP monitoring (ABPM), and the third day will include EndoPAT assessments of endothelial function. In addition, blood samples were collected for optional determination of exploratory biomarkers, including metabolic markers associated with metabolic syndrome (see Schedule of Events). On Day 19, after assessments were completed, patients were discharged from the Study Center at the Investigator's discretion. Patients were rescreened should they discontinue in the Screening Period due to visit window deviations or other administrative reasons. In addition, laboratory values, ECG values, or BPs that were outside the range specified in the protocol were repeated to confirm eligibility during the screening period at the Investigator's discretion after consultation with the Medical Monitor.

Follow-up Period: The Follow-up Period began immediately after Discharge of the patient from the Study Center and lasted for 27 (±3) days. Patients returned to the Study Center 14 (±2) days after the final dose of study drug (Day 32) for the Follow-up Visit. At this visit, in addition to safety and PK assessments, patients had EndoPAT assessments before and after a 0.4 mg dose of sublingual nitroglycerin. Patients remained in the Study Center for ≥2 hours until BP and pulse returned to predose or acceptable, safe levels. Patients returned to the Study Center 28 (±3) days after the final dose of study drug (Day 46) for the End of Trial Visit for final safety and PK assessments (see Schedule of Events).

Patients who prematurely discontinued dosing remained in the clinic for at least 24 hours after their final dose of study drug and completed all Discharge day assessments. In addition, these patients returned to the Study Center for their Follow-up and End of Trial Visits 14 (±2) and 28 (±3) days, respectively, after their final dose of study drug.

Stopping Criteria

All dosing was to be stopped if the Sponsor and Investigator determined that any of the following had occurred:

Drug-related severe adverse events (SAEs) in 2 or more patients (per causality and SAE definitions in the protocol)

An overall pattern of clinically significant AEs or an overall pattern of patient tolerability issues, which may appear minor in terms of an individual event but, in the opinion of the Sponsor or Investigator, collectively represents a safety concern Note: Safety and tolerability was to be assessed daily and dosing was discontinued or dose escalation was cancelled on an individual patient basis. Patients who discontinued dosing or did not escalate remained in the clinic for at least 24 hours after their final dose of study drug and completed all Discharge day assessments. In addition, these patients returned to the Study Center for their Follow up and End of Trial Visits 14 (±2) and 28 (±3) days, respectively, after their final dose of study drug.

Primary Outcome Measures:

Treatment Emergent Adverse Events [Time Frame: 49 Days]; Change from baseline in systolic and diastolic BP and heart rate measurements [Time Frame: 19 Days]; Change in Endothelial Function as assessed by EndoPAT evaluation [Time Frame: 19 Days].

Dosage Regimens:

Escalating single doses (in 3-day cycles) of 10, 20, 30, 40 or 50 mg of Compound I. Compound I has previously been described in WO2014144100. Metabolic parameters, including fasting serum glucose levels, fasting serum insulin levels, hemoglobin A1C (HhA1C) levels, serum lipid levels and body weight, were determined on the second day of each 3-day cycle.

Fasting glucose (mg/dL) was measured in serum both enzymatically. Insulin (pmol/L) was measured by ECLIA. Cholesterol (mg/dL) was measured enzymatically. Triglycerides (mg/dL) were measured enzymatically. HbA1c (%) was measured using Roche Tina Quant.

Study Drug:

Compound I was administered as multiples of a 5-mg oral tablet dosage form. Placebo was administered as multiples of a 5 mg tablet. Compound I was formulated as a spray dried dispersion formulation as described in WO2017095697.

Study Drug Administration

Patients received orally administered study drug at approximately the same time (±15 minutes) every day in the morning (8 to 10 AM), after an overnight fast of at least 8 hours. Patients took multiple tablets together as needed to complete the total dose. Permitted concomitant medications that the patient may have been taking in the morning for diabetes and hypertension, or any other allowed concomitant conditions, had to be taken at the same time as study drug. Breakfast was to begin within 30 minutes after dosing.

| Arms | Assigned Interventions |
|---|---|
| Placebo Comparator: Control Placebo taken once daily Day 1-Day 3 | Drug: Matching Placebo |
| Experimental: 10 mg Compound I 10 mg Compound I taken once daily Day 4-Day 6 | Drug: Compound I |
| Experimental: 20 mg Compound I 20 mg Compound I taken once daily Day 7-Day 9 | Drug: Compound I |
| Experimental: 30 mg Compound I 30 mg Compound I taken once daily Day 10-Day 12 | Drug: Compound I |
| Experimental: 40 mg Compound I 40 mg Compound I taken once daily Day 13-Day 15 | Drug: Compound I |
| Experimental: 50 mg Compound I 50 mg Compound I taken once daily Day 16-Day 18 | Drug: Compound I |

Eligibility

30 Years to 65 Years (Adult)

Sexes Eligible for Study: All

Accepts Healthy Volunteers: No

Criteria

Inclusion Criteria:

Patient is ambulatory male or female

Patient's body mass index score is >20 and <40 kg/m2 at the Screening Visit

Women of childbearing potential must have a negative pregnancy test at the time of check-in and must agree to use double-barrier contraception throughout the duration of the study Patient's health is stable with no clinically significant findings on a physical examination Patient has type 2 (i.e. adult onset) diabetes mellitus diagnosed by a physician or nurse practitioner >6 months before the Screening Visit, and an entry HbA1c that does not mandate prompt intervention for improved control Patient has hypertension diagnosed by a physician or nurse practitioner >6 months before the Screening Visit and BP within the protocol's acceptable range Patients must be on a stable regimen for glycemic control, and a stable regimen for hypertension control that includes an angiotensin converting enzyme inhibitor (ACEi) or angiotensin receptor blocker (ARB)

Other Inclusion Criteria Per Protocol

Exclusion Criteria:

Patient has a clinically significant active or unstable medical condition that, in the opinion of the Investigator, would preclude trial participation Patient is on medication(s) that when co-administered with a soluble guanylate cyclase (sGC) stimulator, could increase the risk of hypotension Patient has evidence of severe or active end-organ damage attributable to diabetes Patient has severe renal insufficiency, has undergone renal transplantation, or has planned renal transplantation Other Exclusion Criteria Per Protocol Study Population The study enrolled 11 patients with type 2 diabetes with a hemoglobin A1c (HbA1c) level of ≤10.5% and a fasting (≥8 hours) blood glucose level of ≤240 mg/dl on a regimen of ≥1 medication for glycemic control with no change in medication for at least 12 weeks before Check-in and on a stable regimen (ie, same drug and same dose) for ≥28 days before Check-in and Hypertension with systolic BP of 120 to 160 mm Hg and diastolic BP of 70 to 100 mm Hg while on a stable regimen of ≥1 medication for at least 30 days before the Screening Visit that includes an angiotensin-converting enzyme inhibitor (ACEi) or angiotensin receptor blocking agent (ARB).

Participant Demographics

11 Patients were enrolled. Age mean was 56.6 years old (range 45-64 years). Mean weight was 91 Kg (range 75-115 Kg). Mean BMI was 31.7 (Range 28.1 to 39.5). Systemic BP mean: 136 mmHg (range 124-160 mm Hg).

Top-Line Metabolic Assessments Results

"Change results", unless otherwise indicated, are relative to assessments in the pre-study baseline or day-1. When the change is relative to the placebo cycle (day 2) it will be indicated so.

Metabolic parameters fasting blood glucose, serum fasting insulin, HbA1C, serum cholesterol, serum triglycerides, and liver enzyme levels were obtained using standard methods and kits as those regularly used at a standard diagnostic laboratory. Weight was determined using standard doctor's office scales.

The serum ApoB level was determined using microsphere-based HSP-ApoB assay, consisting of using antigen-specific antibodies optimized in a capture-sandwich format. 5 µL of a diluted mixture of capture-antibody microspheres were mixed with 5 µL bloker and 10 µL standard, pre-diluted sample, or control in a hard-bottom microtiter plate. Plama and serum samples were diluted of the appropriate dilution. The plate was incubated for 1 hour at room temperature. 10 µL biotinylated detection antibody was added to each well, thoroughly-mixed and incubated for 1 hour. 10 µL diluted Streptavidin-phycoerythrin was added to each well, thoroughly mixed, and incubated for 60 minutes. A filter-membrane microtiter plate was pre-wetted by adding 100 µL wash buffer followed by aspiration via a vaccum manifoled device. The reaction contents of the hard-bottom plate were then transferred to the respective wells of the filter plate. All wells were vacuum aspirated and the contents were washed twice with 100 µL wash buffer. After the last wash, 100 µL wash buffer was added to each well, and the washed microspheres were resuspended with thorough mixing. The plate was then analyzed on the Luminex platform.

Plasma ADMA concentrations were determined by liquid chromatography and tandem mass spectrometry (LC-MS/

MS). Plasma samples of the patients were collected in a purple-top container with K2 EDTA anticoagulant. The tube was filled completely and the sample was mixed well and separated by centrifugation. A minium volume of 0.20 mL was needed for testing and the plasma sample was extracted by a simple protein precipitation. The supernatant was then transferred to a diluent before analysis. The extract was analyzed using liquid chromatography (LC) with tandem mass spectrometry (MS/MS). The standard curve was 10.0 ng/mL to 1000.0 ng/mL.

Figure 7:
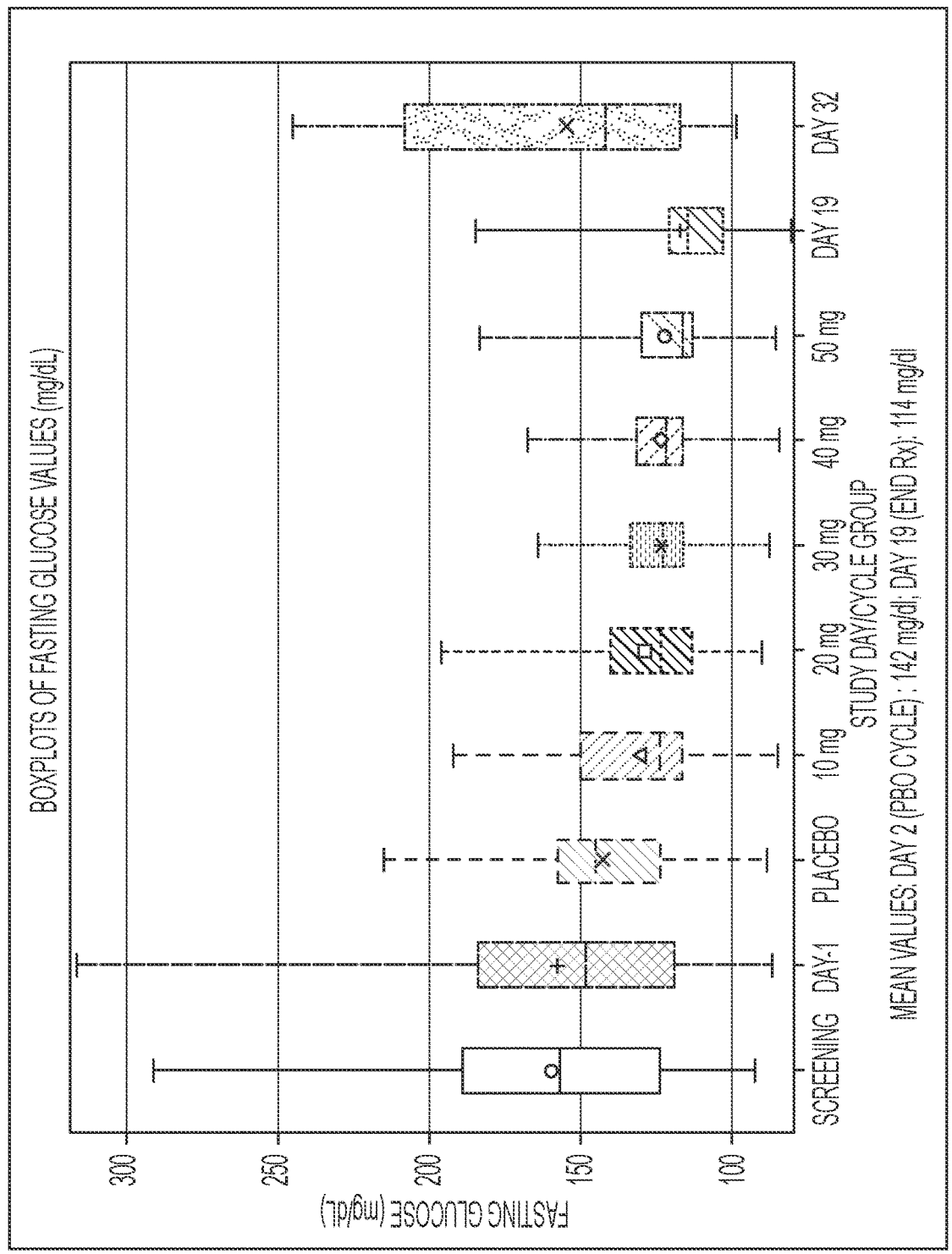
FIG. 7 shows fasting blood glucose levels in patients treated with escalating doses of Compound I in a clinical study (Example 3). The symbols in the boxplot indicate the mean values. The boxes show the interquartile range (25%-75%) and the whiskers show the low to high range.
Figure 8:
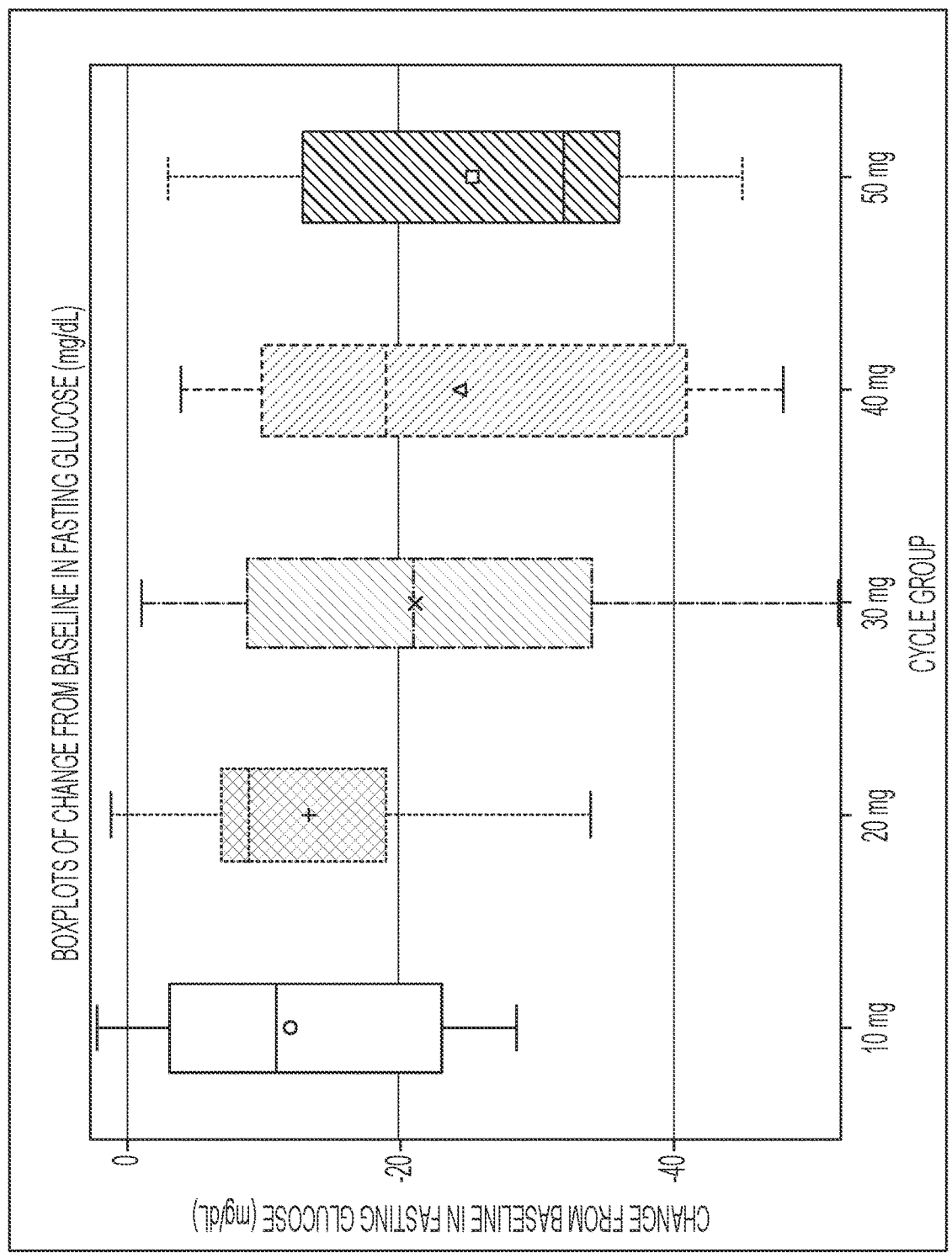
FIG. 8 shows change (decrease) from time-matched placebo (day 2) in fasting blood glucose levels in patients treated with escalating doses of Compound I in a clinical study (Example 3). The symbols in the boxplot indicate the mean values. The boxes show the interquartile range (25%-75%) and the whiskers show the low to high range.
Figure 9:
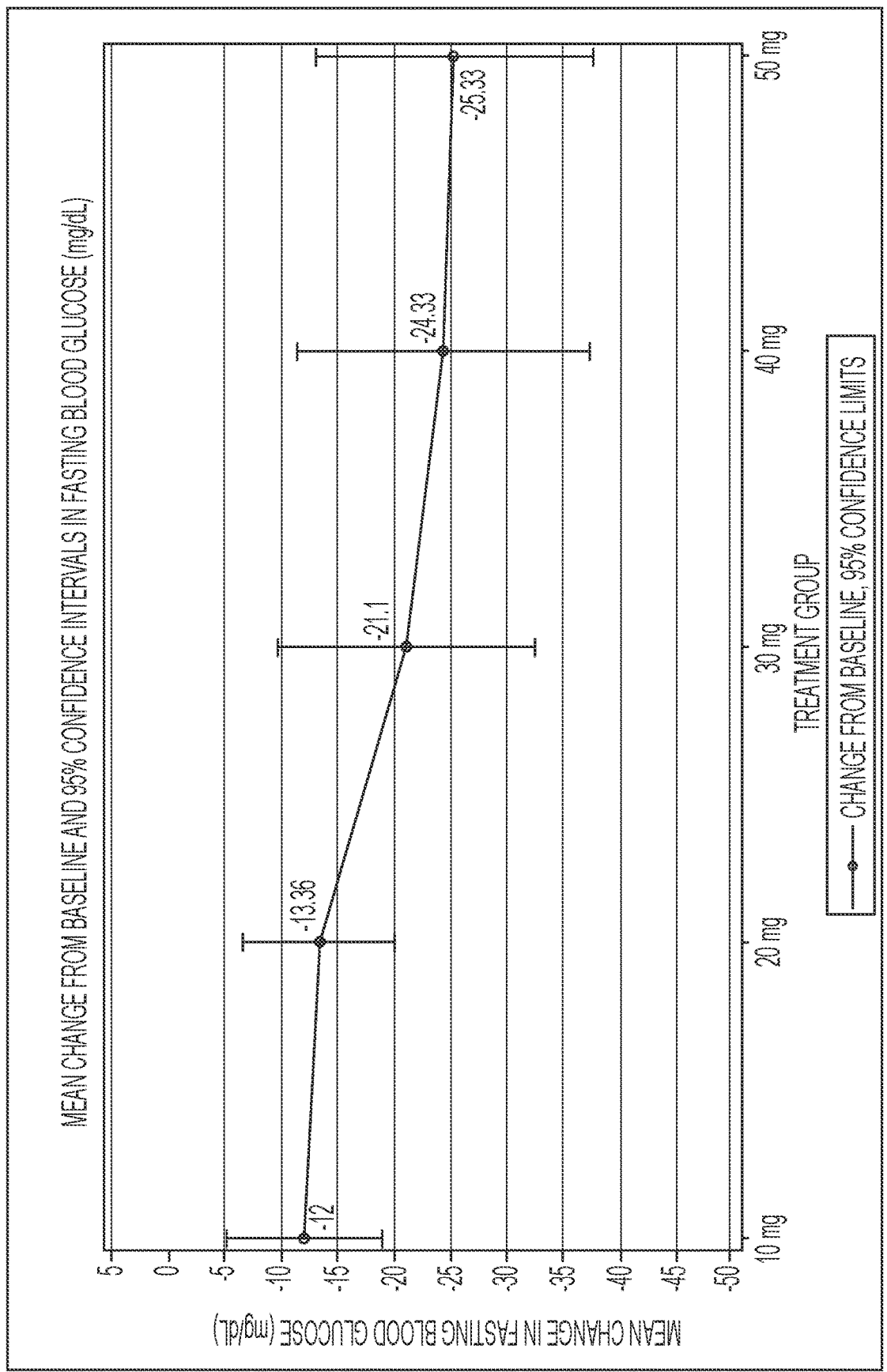
FIG. 9 shows mean reduction from time-matched placebo (day 2) in fasting blood glucose levels in patients treated with escalating doses of Compound I in a clinical study (Example 3). The bars in the plot show the 95% confidence limits around the means.

Mean fasting glucose level on day 2 (placebo cycle) was 142 mg/dl. Mean fasting glucose level on day 19 (end of treatment) was 114 mg/dl. Thus, a 20% reduction in the mean fasting glucose level was observed between the placebo cycle and the end of treatment, after escalation from a single oral daily dose of 10 mg, to 20 mg, to 30 mg, to 40 mg, to 50 mg of Compound I. Reductions in mean fasting glucose levels between placebo and different dosages varied between about −12 mg/dL and about −25 mg/dL, depending on the dose used, as shown in FIG. 7, which shows the mean fasting glucose values by dose from screening to day 32 (end of treatment is day 19). FIG. 8 displays the change in fasting glucose levels for each dose level relative to the baseline as a boxplot. FIG. 9 displays the change in mean fasting glucose level for each dose level relative to the baseline.

Table 2 below summarizes the reduction in the mean and median fasting serum insulin values relative to time-matched placebo (day 2). The mean reduction of insulin levels ranged from about −0.40 µIU/dL to about −2.70 µIU/dL depending on the dose for dosages between 20 mg and 50 mg.

TABLE 2

Change in fasting serum insulin from baseline levels by dose (doses increase from left to right, from 10 mg, to 20 mg, to 30 mg, to 40 mg to 50 mg).

| Change Serum Insulin | | | | | | |
|---|---|---|---|---|---|---|
| | Mean | 0.20 | −0.40 | −2.61 | −2.49 | −2.70 |
| | SD | 5.04 | 6.26 | 3.11 | 5.65 | 4.20 |
| | 95% CI | −3.19, 3.59 | −4.60, 3.80 | −4.84, −0.38 | −6.84, 1.86 | −5.93, 0.53 |
| | Median | −0.50 | 0.10 | −2.00 | −1.90 | −0.70 |
| | 25th, 75th PCTL | −4.10, 4.00 | −4.50, 2.00 | −3.70, −0.70 | −7.00, 1.10 | −7.00, 0.10 |
| | % CV | 2521.21 | −1564.13 | −119.32 | −227.19 | −155.71 |
| | Min, Max | −6.7, 9.4 | −8.3, 14.7 | −9.6, 0.7 | −11.4, 6.1 | −9.2, 2.6 |
| | n | 11 | 11 | 10 | 9 | 9 |

Figure 10:
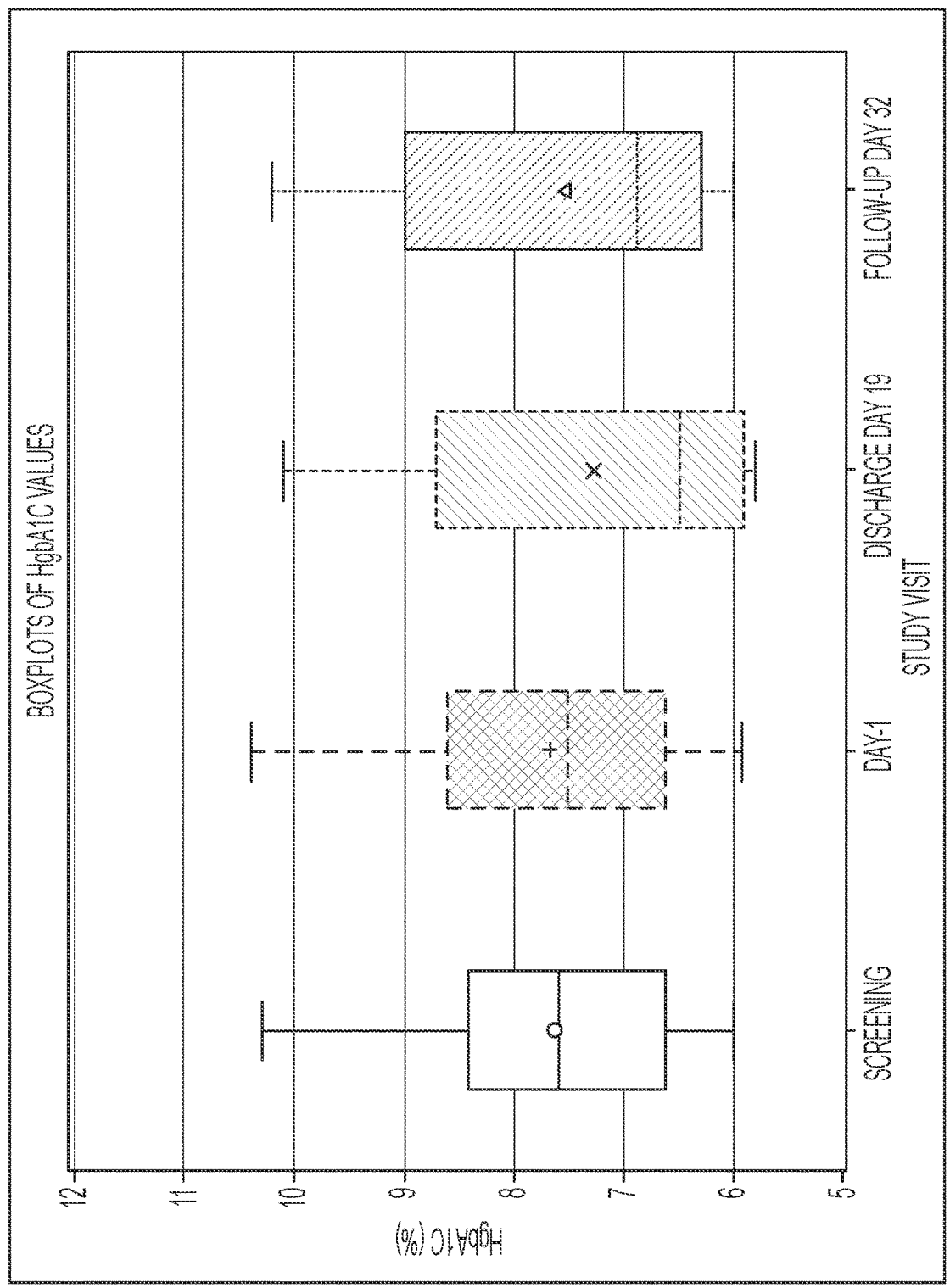
FIG. 10 shows hemoglobin A1C (HbA1C) levels in patients treated with escalating doses of Compound I in a clinical study (Example 3). The symbols in the boxplot indicate the mean values. The boxes show the interquartile range (25%-75%) and the whiskers show the low to high range.
Figure 11:
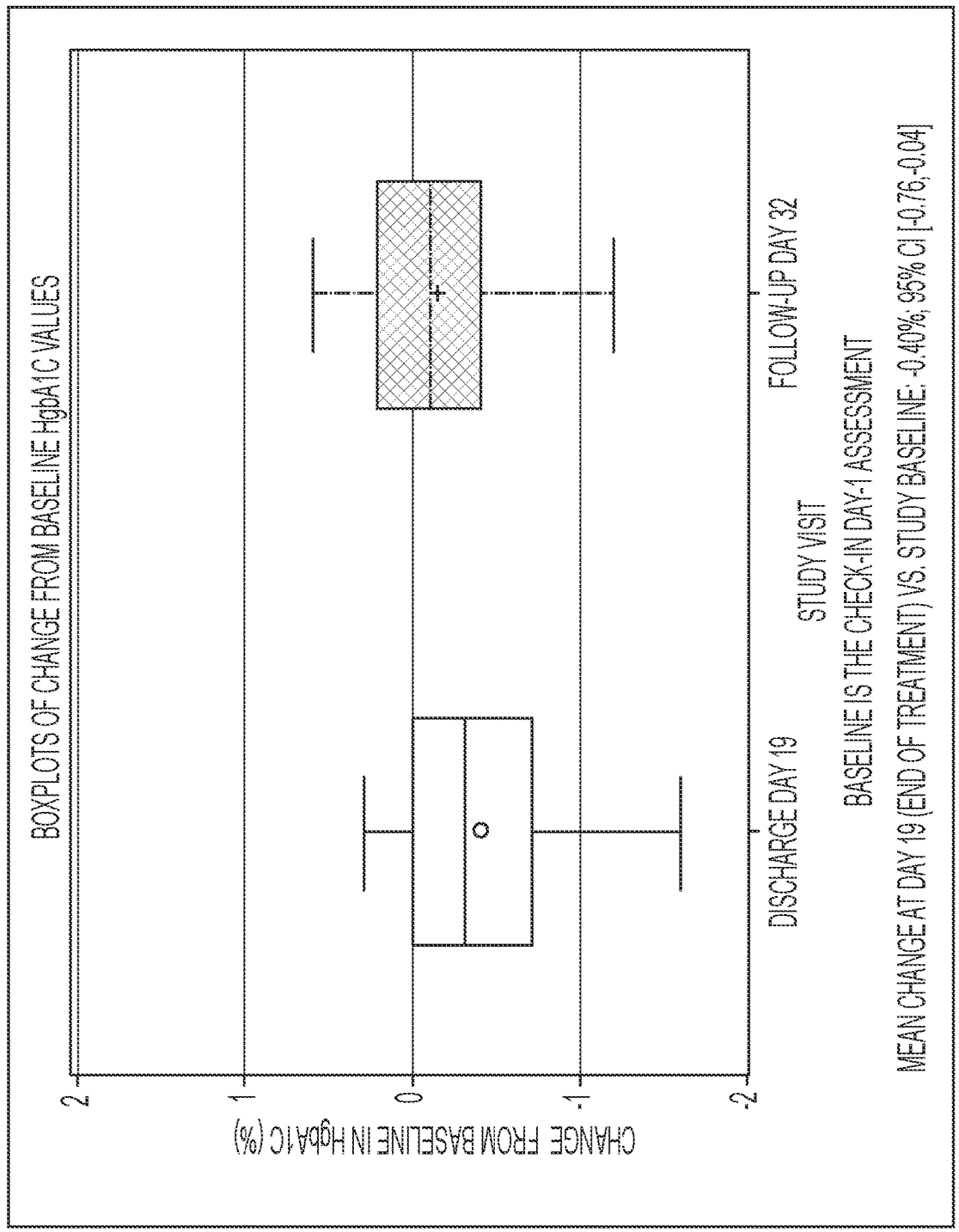
FIG. 11 shows changes from baseline (day-1) in HbA1C levels in patients treated with escalating doses of Compound I in a clinical study (Example 3). The symbols in the boxplot indicate the mean values. The boxes show the interquartile range (25%-75%) and the whiskers show the low to high range.

FIG. 10 shows the mean values for Hemoglobin A1C levels (HbA1AC) measured at screening, on day-1, on discharge day (day 19) and on follow-up day 32. FIG. 11 shows the changes in HbA1C levels relative to baseline on discharge day 19 and on follow-up day 32. At day 19 the mean reduction from baseline was 0.40%.

Figure 12:
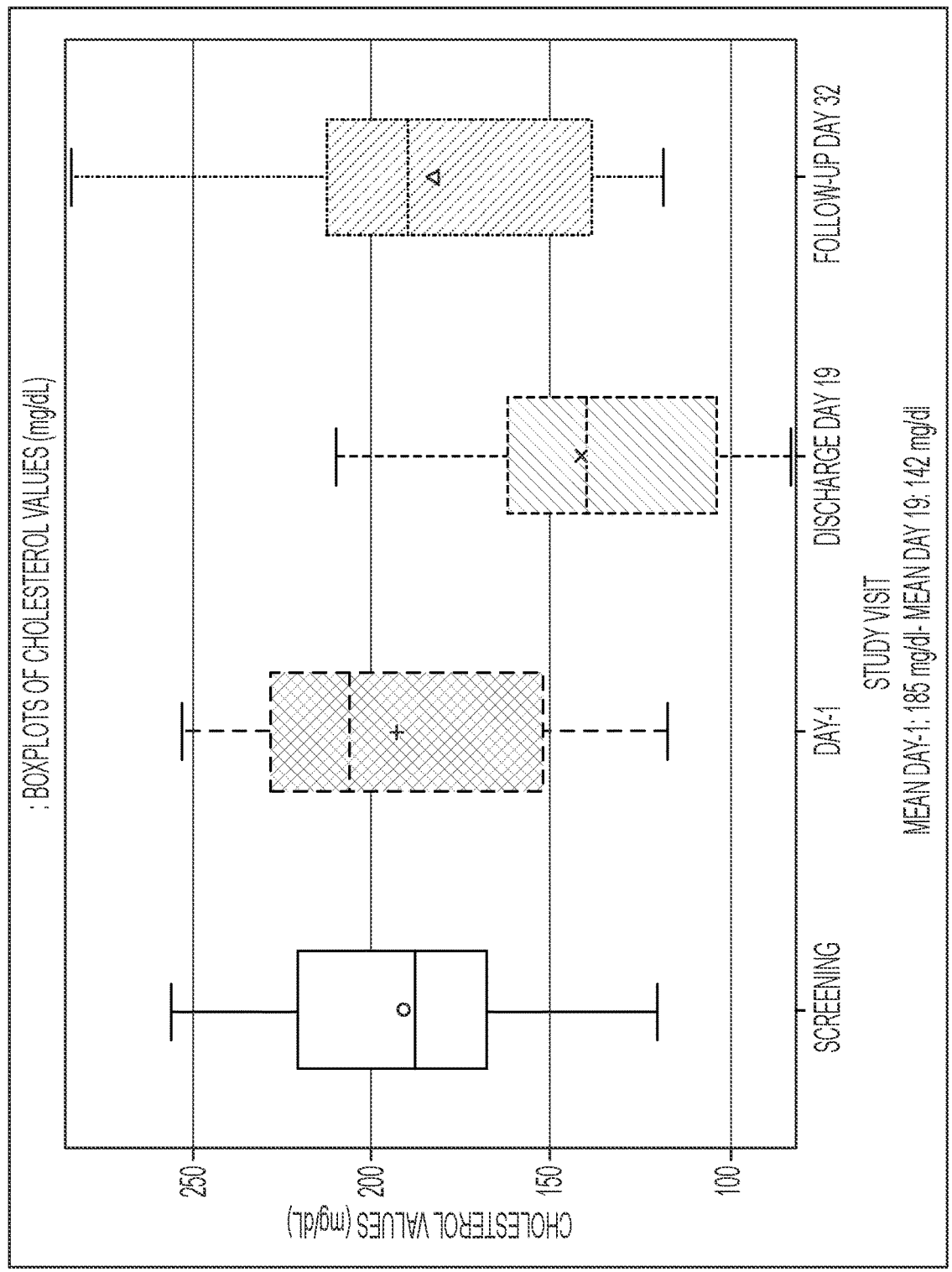
FIG. 12 shows serum cholesterol levels in patients treated with escalating doses of Compound I in a clinical study (Example 3). The symbols in the boxplot indicate the mean values. The boxes show the interquartile range (25%-75%) and the whiskers show the low to high range.
Figure 13:
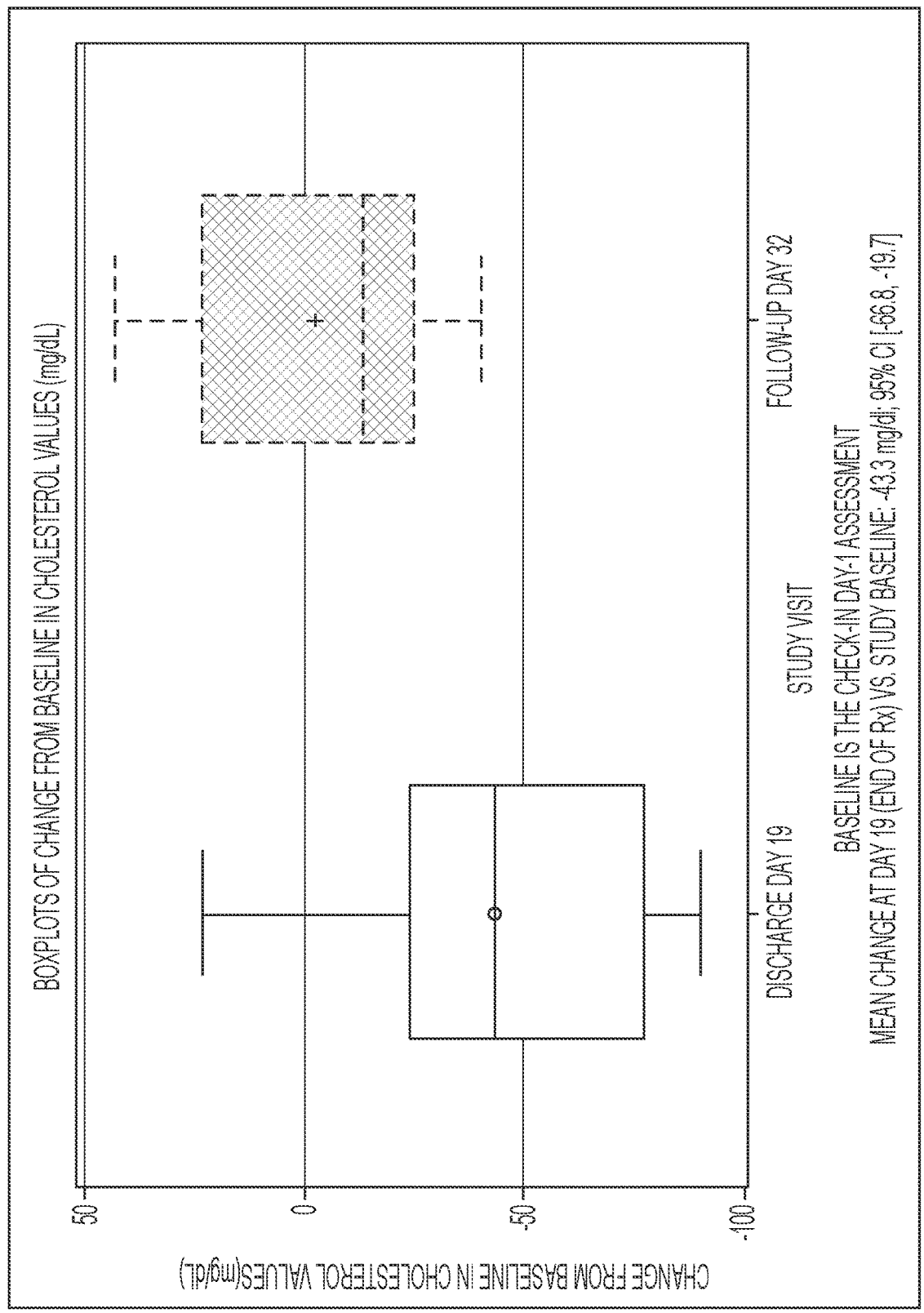
FIG. 13 shows changes from baseline (day-1) in serum cholesterol levels in patients treated with escalating doses of Compound I in a clinical study (Example 3). The symbols in the boxplot indicate the mean values. The boxes show the interquartile range (25%-75%) and the whiskers show the low to high range.

FIG. 12 shows mean serum cholesterol levels on screening visit, day-1, discharge day 19 and follow-up day 32. The mean cholesterol level on day-1 (baseline) was 185 mg/dL. The mean cholesterol level on day 19 was 142 mg/dL. Thus, a 23% reduction in the mean cholesterol level was observed between the baseline and the end of treatment, after escalation from a single oral daily dose of 10 mg, to 20 mg, to 30 mg, to 40 mg, to 50 mg of Compound I over 15 days. FIG. 13 shows the change in the levels of cholesterol between discharge day 19 and follow up day 32. The change between the mean serum cholesterol value on day 19 (end of treatment) and the value on day 32 was +43.3 mg/dL (CI [−66.8, −19.7]).

Figure 14:
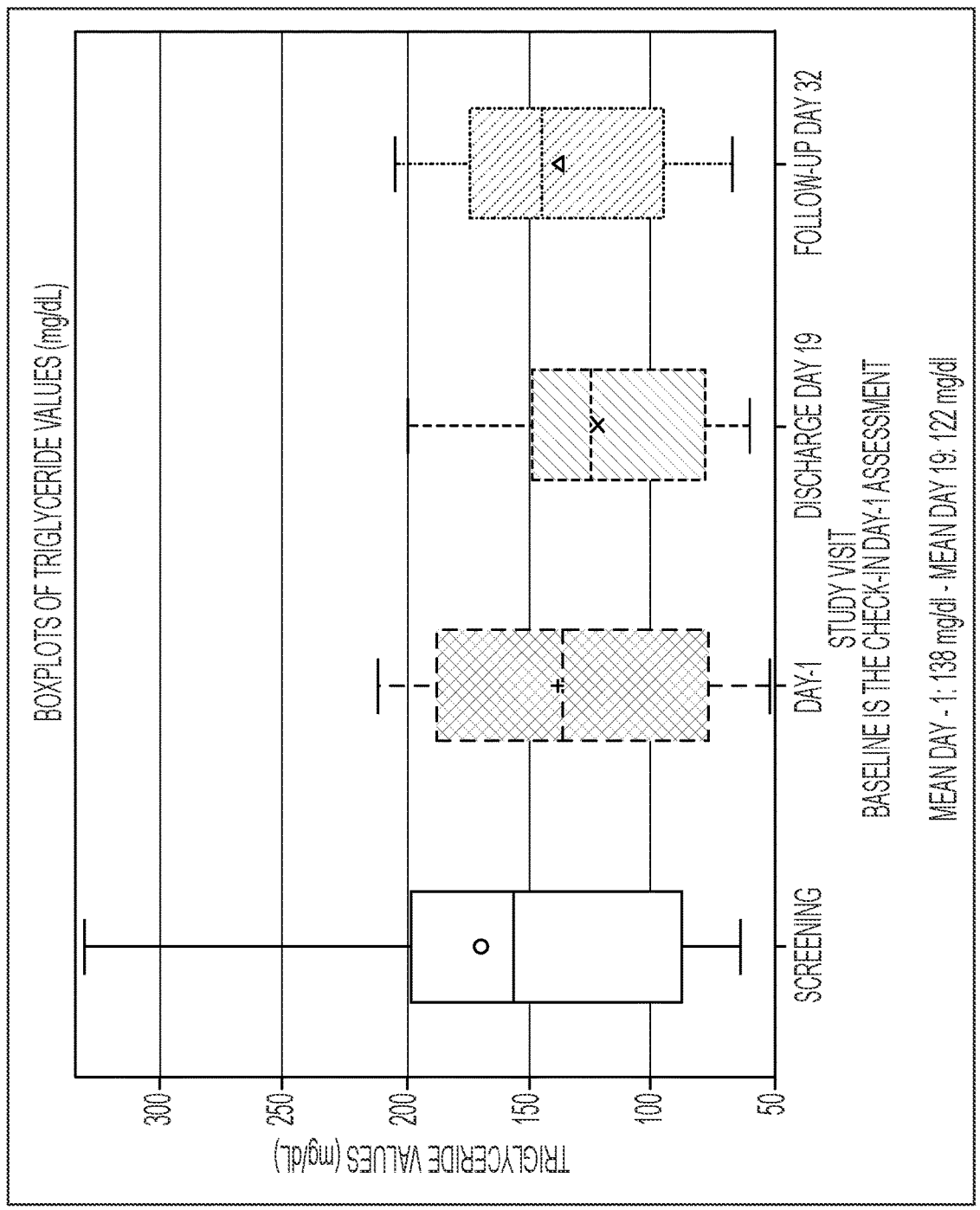
FIG. 14 shows serum triglyceride levels in patients treated with escalating doses of Compound I in a clinical study (Example 3). The symbols in the boxplot indicate the mean values. The boxes show the interquartile range (25%-75%) and the whiskers show the low to high range.

FIG. 14 shows mean values for serum triglyceride (TG) levels on screening, on day-1, discharge day 19 and follow-up day 32. On day-1 the mean serum TG level was 138 mg/dl. On day 19 the mean serum TG level was 122 mg/dl. Thus a reduction of about 12% in the levels of serum TGs was observed between day-1 (baseline) and day 19, after escalation from a single oral daily dose of 10 mg, to 20 mg, to 30 mg, to 40 mg, to 50 mg of Compound I over 15 days.

Figure 15:
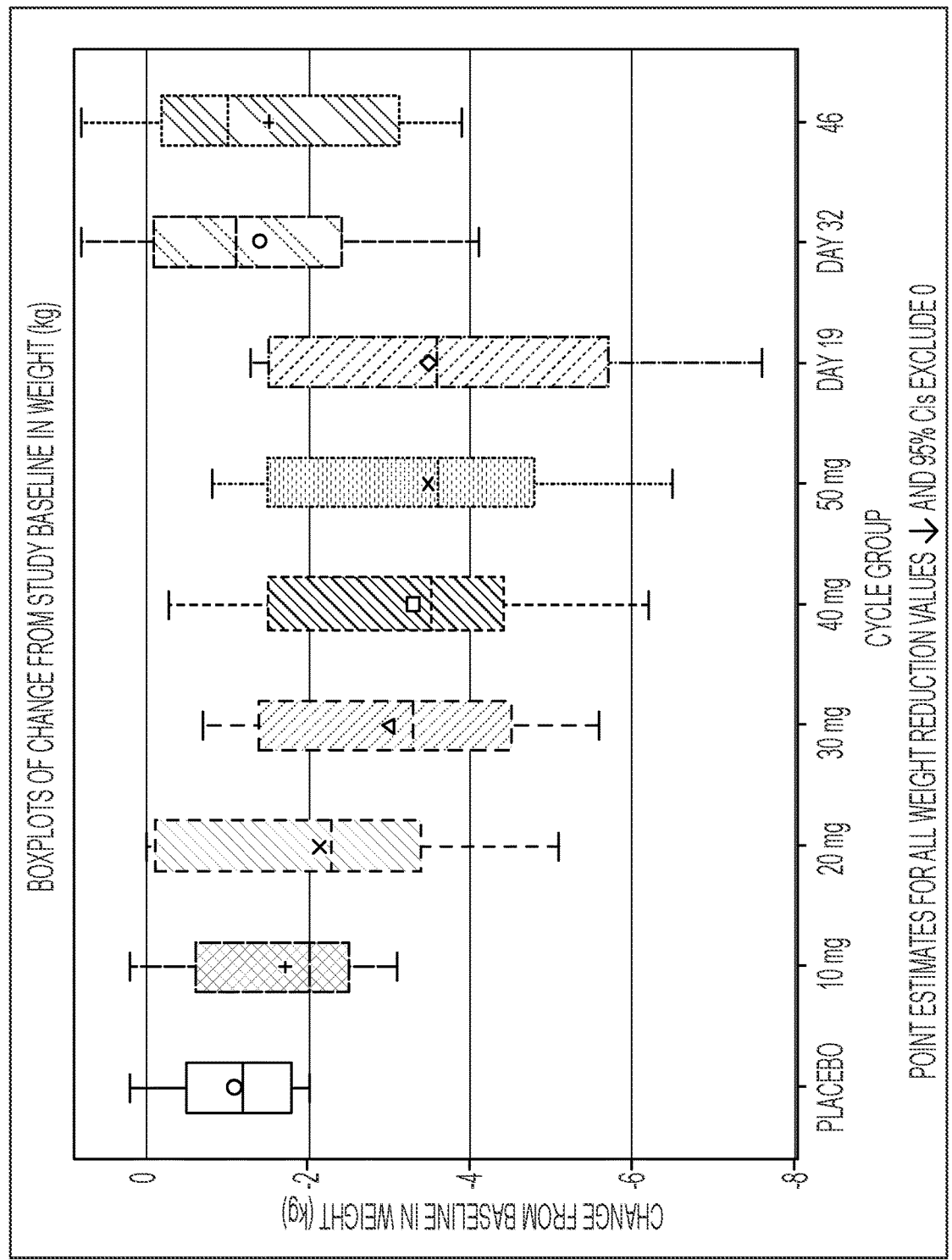
FIG. 15 shows reductions from baseline (day-1) in body weight in patients treated with escalating doses of Compound I in a clinical study (Example 3). The symbols in the boxplot indicate the mean values. The boxes show the interquartile range (25%-75%) and the whiskers show the low to high range.

FIG. 15 shows changes in mean body weight for each dosage relative to the baseline (day-1). As shown, mean body weights decreased for all dosages and were cumulative over the period of dose escalation, returning to normal after day 32.

Conclusions

Compound I was well tolerated in this open label multiple dose escalation trial in patients with Type 2 diabetes and hypertension. Substantial declines in mean fasting serum glucose levels relative to baseline were observed across the study, with decline magnitudes increasing progressively as times/doses increased.

Mean fasting serum glucose levels appeared to return to the level of pre-study baseline by day 32, 13 days after dosing/in clinic confinement had completed.

Mean HbA1C demonstrated declines between pre-initiation of dosing (day-1) and end of dosing period (day 19), with reversion towards pre-treatment levels at day 32.

Serum cholesterol and triglyceride levels followed the same pattern, with more substantial proportional declines by end of treatment day 19 for cholesterol.

Body weight progressively declined over the course of the in-clinic study, with a mean reduction of about 3.5 kg by the end of treatment day 19.

Of the 11 patients participating in this trial, 7 were taking a statin (e.g., atorvastatin, pravastatin, simvastatin).

Of the 11 patients participating in this trial, all of them were on a blood glucose reduction medication. Nine of those were only on oral blood glucose reduction medications (i.e. not insulin) including metformin, glipizide and combinations thereof.

Of the 11 patients participating in this trial, all of them were on an anti-hypertensive drug of the ARB or ACE class (e.g., zestoretic, lisinopril, enalapril, losartan). One patient was on a combination of 3 anti-hypertensives (including lisinopril, metropolol, a beta-blocker and spironolactone, a diuretic). One patient was on a combination of 2 anti-hypertensives, including losartan and metropolo, a beta-blocker.

Example 4: A Phase 2a Study to Compare Safety, Tolerability, Pharmacokinetics, and Pharmacodynamics of 2 Dose Regimens of Compound I in Patients with Stable Type 2 Diabetes and Hypertension The primary objectives of this clinical study (ClinicalTrials.gov Identifier: NCT03091920) were to compare the safety, tolerability, PK profile, and PD effects of 2 treatment regimens of Compound I tablet (40 mg per day, as 20 mg BID or as 40 mg QD) administered orally for 2 weeks to patients with stable type 2 diabetes mellitus and hypertension. Patients in this trial were on stable medications for glucose control (blood glucose lowering medication, antihyperglycemics) and hypertension (antihypertensives). Secondary measurements included assessment of fasting glucose levels, fasting insulin levels, hemoglobin A1C (HbA1C) levels, serum cholesterol levels, ApoB levels, HOMA-IR, ADMA concentrations, serum triglyceride levels, BMI, liver transaminases and body weight, among others.

Figure 30:
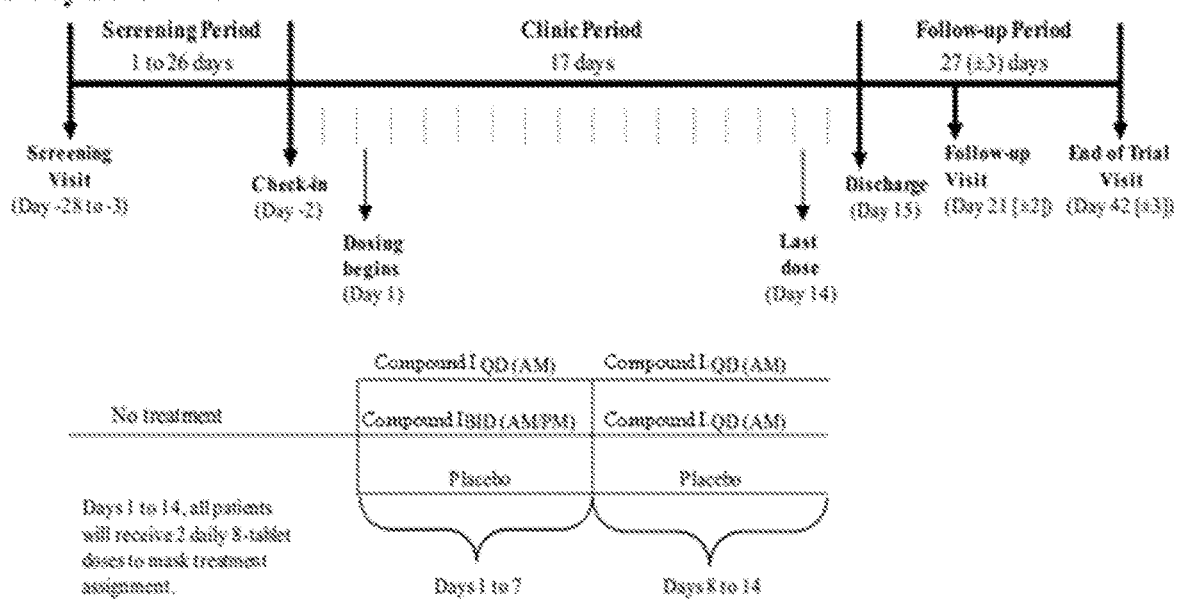
FIG. 30 shows a study schematic diagram of a Phase 2a study to compare safety, tolerability, pharmacokinetics, and pharmacodynamics of 2 dose regimens of Compound I in patients with stable type 2 diabetes and hypertension.

Study Type:
  Interventional
Study Design:
  Allocation: Randomized; Intervention Model: Parallel Assignment; Masking: Triple (Participant, Care Provider, Investigator); Masking Description: Double-Blind; Primary Purpose: Treatment
  This is a randomized, double-blind, placebo-controlled study consisting of 3 distinct periods (see FIG. 30).
  13 male patients and 13 female patientes with stable type 2 diabetes and hypertension were enrolled. Patients were randomized in a 5:5:3 ratio (QD:BID:Placebo) to receive 1 of 2 Compound I treatment regimens or placebo (all regimens were masked) as outlined in the table above.

| Treatment Arm | Dose time | Days 1 to 7 | Days 8 to 14 |
|---|---|---|---|
| QD/QD | AM | 40 mg Compound I | 40 mg Compound I |
|  | PM | Placebo | Placebo |
| BID/QD | AM | 20 mg Compound I | 40 mg Compound I |
|  | PM | 20 mg Compound I | Placebo |
| PBO/PBO | AM | Placebo | Placebo |
|  | PM | Placebo | Placebo |

Study Periods
  The patients were enrolled separately. Each patient progressed through 3 study periods.
  Screening Period: The Screening Period began with the signature of the informed consent form (ICF) at the Screening Visit (which can occur from Day-28 to Day-3) and lasted 1 to 26 days. At the Screening Visit, patients underwent preliminary screening procedures to determine their eligibility for the study. The end of the Screening Period coincided with the beginning of the Clinic Period at Check-in.
  Clinic Period: The Clinic Period began at Check-in on Day-2 (2 days before dosing) and ended at the time of Discharge on Day 15. During the 17-day Clinic Period, patients were confined to the Study Center and received a standard diet for diabetics. Patients who met eligibility criteria based on Screening Visit assessments were admitted to the Study Center on Day-2 for baseline procedures. On the morning of Day 1 (there is no Day 0), eligible patients were randomized in a 5:5:3 ratio to 1 of 3 masked treatment regimens: QD/QD, BID/QD, or PBO/PBO. On Days 1 to 14, patients received a morning (AM) dose and an evening (PM) dose.
  Safety, PK, and PD assessments, including blood collections, were performed at specified times throughout the Clinic Period (see Criteria for Evaluation and Schedule of Events). On Day 15, after assessments were completed, patients were discharged from the Study Center at the Investigator's discretion.
  Follow-up Period: The Follow-up Period began immediately after Discharge from the Study Center on Day 15 and lasted for 27 (±3) days. On Day 21 (±2 days), 7 (±2) days after the last dose of study drug, patients returned to the Study Center for the Follow-up Visit. On Day 42 (±3 days), 28 (±3) days after the last dose of study drug, patients returned to the Study Center for the End of Trial Visit.

Study Drug
  Compound I was administered as multiples of a 5 mg oral tablet dosage form. Placebo was administered as multiples of a 5 mg tablet. Compound I was formulated as a spray dried dispersion formulation as described in WO2017095697.

Dosage Regimens and Mode of Administration
  On Days 1 to 14, all patients received 2 daily 8-tablet doses (AM and PM), 12 hours (±30 minutes) apart. Matching placebo tablets were administered with Compound I Tablets when required to mask treatment assignments. The table outlines study drug dosage by week and time for each regimen/treatment arm.

| Regimen/ Treatment arm | Dose time | Dosage Days 1 to 7 | Dosage Days 8 to 14 |
|---|---|---|---|
| QD/QD | AM | 8 × Compound ITablet | 8 × Compound ITablet |
|  | PM | 8 × placebo tablet | 8 × placebo tablet |
| BID/QD | AM | 4 × Compound ITablet 4 × placebo tablet | 8 × Compound ITablet |
|  | PM | 4 × Compound ITablet 4 × placebo tablet | 8 × placebo tablet |
| PBO/PBO | AM | 8 × placebo tablet | 8 × placebo tablet |
|  | PM | 8 × placebo tablet | 8 × placebo tablet |

Study Drug Administration
  All patients received 2 orally administered doses per day: an AM dose and a PM dose. Except for Day 13, patients received the AM dose at approximately the same time (±15 minutes) every day in the morning (8 to LOAM) following an overnight fast of ≥8 hours. (Note: For each patient, the first dose on Day 1 was administered between 8 and LOAM; thereafter, AM doses on Days 2 to 12 and on Day 14 must be administered within 15 minutes of the time of dosing on Day 1.) On Day 13, if EndoPAT was planned, the first dose was to be administered in the morning between 7 and 10:30 AM, after the EndoPAT assessment. Breakfast was to begin within 30 minutes after dosing. Each patient received their PM dose 12 hours (±30 minutes) after their AM dose and at least 30 minutes after completing a normal dinner. Patients took multiple tablets together as needed to complete the total dose. Permitted concomitant medications may have been taken at the same time as study drug.

Study Population
  The study enrolled 13 female patients and 13 male patients with:
    Type 2 diabetes with a hemoglobin A1c (HbA1c) level of ≤10.5% and a fasting (≥8 hours) serum glucose level of ≤240 mg/dL on a regimen of ≥1 medication for glycemic control with no change in medication for ≥12 weeks before Check-in and on a stable regimen (ie, same drug and same dose) for ≥28 days before Check-in Hypertension with systolic BP of 120 to 160 mm Hg and diastolic BP of 70 to 100 mm Hg while on a stable regimen of ≥1 medication, which includes an angiotensin-converting enzyme inhibitor (ACEi) or angiotensin receptor blocking agent (ARB), for ≥28 days before Check-in.

Eligibility Criteria

Inclusion Criteria:

Patients had to meet all of the following criteria to be eligible for enrollment in this study:

Patient is an ambulatory male or female aged 30 to 75 years at the Screening Visit.

Female patient is not pregnant or breastfeeding at the time of the Screening Visit and Check-in. Negative serum pregnancy tests must be documented at the Screening Visit and at Check-in before dosing.

Female patients must be postmenopausal (no menses for 12 consecutive months), surgically sterile (ie, bilateral oophorectomy, hysterectomy, or tubal ligation), or, if of childbearing potential, agree to use 1 of the following methods of birth control from the date they sign the ICF until after the End of Trial Visit:

a. Combination of 2 highly effective birth control methods (e.g., condom with spermicide plus intrauterine device, condom with spermicide plus a diaphragm or cervical cap, hormonal contraceptive [including progesterone implant] combined with a barrier method)

b. Maintenance of a monogamous relationship with a male partner who has been surgically sterilized by vasectomy (vasectomy procedure must have been conducted ≥60 days before the Screening Visit or confirmed via sperm analysis) plus a hormone or barrier method Patient's body mass index (BMI) score is >20 and <40 kg/m2 at the Screening Visit.

Patient's health is stable with no clinically significant findings on a physical examination, 12-lead ECG, alcohol breathalyzer, and clinical laboratory tests (serum chemistry, hematology, coagulation, urine drug screen, and urinalysis) that would prevent participation in the trial. (Note: The Investigator will determine if a particular finding is clinically significant. In making this determination, the Investigator will consider whether the particular finding could prevent the patient from performing any of the protocol-specified assessments, could represent a condition that would exclude the patient from the study, could represent a safety concern if the patient participates in the study, or could confound the study-specified assessments.)

Patient has type 2 (ie, adult onset) diabetes mellitus diagnosed by a physician or nurse practitioner ≥6 months before the Screening Visit and meets all of the following:

a. Has been on a regimen of ≥1 medication for glycemic control, which may include long-acting insulin, with no change in medication for ≥12 weeks before Check-in and on a stable regimen (ie, same drug and same dose) for ≥28 days before Check-in with no indication that the regimen will need to be changed for the duration of the study. Modification of short-acting insulin throughout the Screening Period will not affect eligibility. During the Clinic Period, per Investigator discretion, doses of supplemental short-acting insulin was varied as needed to achieve adequate glycemic control.

b. Has HbA1c level 10.5% and fasting (≥8 hours) serum glucose level 240 mg/dL at the Screening Visit and at Check-in. Glucose value from serum chemistry panel; at Investigator discretion, if fasting serum glucose is >240 mg/dL, the test was repeated for determination of eligibility.

c. Has, in the clinical judgement of the Investigator, sufficient diabetes stability to participate in the trial.

Patient has hypertension diagnosed by a physician or nurse practitioner ≥6 months before the Screening Visit and meets all of the following:

a. Has been on a stable regimen of ≥1 medication to control hypertension for ≥28 days before Check-in with no indication that the regimen will need to be changed for the duration of the study. The medication(s) must include an angiotensin-converting enzyme inhibitor (ACEi) or angiotensin receptor blocking agent (ARB) and may include diuretics and/or calcium channel blockers. Other antihypertensive agents were acceptable per the Investigator's discretion. (See Exclusion Criteria for prohibited medications.)

b. Has supine systolic blood pressure (BP) of 120 to 160 mm Hg and supine diastolic BP of 70 to 100 mm Hg at the Screening Visit. Eligibility will be based on the average of 3 measurements.

c. Has, in the clinical judgement of the Investigator, sufficient hypertension stability to participate in the trial.

Patient has a negative hepatitis panel (hepatitis B surface antigen [HBsAg] and antihepatitis C virus [HCV]) and human immunodeficiency virus (HIV) antibody at the Screening Visit.

Other inclusion criteria per protocol.

Exclusion Criteria:

Patients who met any of the following criteria were eligible to participate in the study:

Patient has a clinically significant active or unstable medical condition that, in the opinion of the Investigator, would preclude trial participation, including active or unstable metabolic; hepatic; renal; hematological; pulmonary; cardiovascular; gastrointestinal; musculoskeletal; dermatological; urogenital; eye, ear, nose, and throat; psychiatric; or neurological conditions.

Patient is on medication(s) that when co-administered with a soluble guanylate cyclase (sGC) stimulator, could increase the risk of hypotension. These include (but may not be limited to) nitrates, nitroglycerin, direct vasodilators (including hydralazine or systemic minoxidil), phosphodiesterase (PDE) 5 inhibitors (including sildenafil, tadalafil, and vardenafil), alpha adrenergic blockers, riociguat, and sodium-glucose co-transporter 2 (SGLT2) inhibitors. Patients should not take these medications from 6 days before Check-in to the End of Trial Visit.

Patient has evidence of severe or active end-organ damage attributable to diabetes (e.g., active diabetic nephropathy, retinopathy, or neuropathy) at the Screening Visit or Check-in.

Patient has evidence of active end-organ morbidity associated with uncontrolled hypertension (e.g, progressive kidney insufficiency, myocardial infarction, or stroke) at the Screening Visit or Check-in. Patient has had an in-patient hospitalization for a cardiovascular, renal, or metabolic cause in the 6 months before the Screening Visit.

Patient has orthostatic decrease in systolic BP of >20 mm Hg or orthostatic decrease in diastolic BP of >15 mm Hg.

Patient has severe renal insufficiency (eg, current or past need for dialysis) has undergone renal transplantation, or has planned renal transplantation.

Patient has a history of malignancy, diagnosed or known to be active or actively treated within the past 5 years, other than resected lesions of low malignant potential, such as basal cell skin cancers.

Patient has bleeding diathesis or history of clinically significant bleeding episodes (e.g., gastrointestinal bleed) in the 12 months before the Screening Visit.

Patient has a 12-lead ECG demonstrating severe bradycardia (heart rate <40 beats per minute) or QTcF is ≥450 msec for male patients or is ≥470 msec for female patients at the Screening Visit. (Note: If on initial ECG, QTcF exceeds the limit, the ECG will be repeated 2 more times, and the average of the 3 QTcF values will be used to determine the patient's eligibility).

Patient has alanine aminotransferase (ALT) or aspartate aminotransferase (AST) level >2 times the upper limit of normal as defined by the laboratory or creatinine level >1.5 times the normal as defined by the laboratory at the Screening Visit.

Patient has a history of clinically significant hypersensitivity or allergies to any of the inactive ingredients contained in the active or placebo drug products.

Patient has a history of active alcoholism or drug addiction during the year before the Screening Visit, or has a positive drug screen at the Screening Visit or at Check-in.

Patient has previously received Compound I in a study or has received an investigational drug during the 30 days or 5 half-lives of that investigational drug (whichever is longer) before the Screening Visit or is planning to receive another investigational drug at any time during the study.

Patient is an active smoker or has used any nicotine-containing products (cigarettes, e-cigarettes, vape pens, cigars, chewing tobacco, gum, patches) during the 6 months before Check-in. Use of nicotine is excluded during the study until after the End of Trial Visit. All positive nicotine tests will result in screen failure.

Patient has consumed grapefruit or grapefruit juice during the 72 hours before Check-in, taken vitamins or herbal supplements during the 7 days before Check-in, or taken any supplements for the treatment of erectile dysfunction during the 14 days before Check-in. Grapefruit, grapefruit juice, vitamins, herbal supplements, or any supplements for the treatment of erectile dysfunction are excluded during the study until after the End of Trial Visit.

Patient has consumed any alcohol-containing foods or beverages during the 7 days before Check-in. Use of alcohol-containing foods or beverages is prohibited from 7 days before Check-in through Discharge. In the clinic, patient may consume up to 2 cups of coffee or tea per day but not within 1 hour of study drug administration or within 3 hours before EndoPAT assessment.

Patient has donated blood products (including plasma and platelet donation) during the 6 weeks before Check-in.

Patient has received blood products during the 2 months before Check-in.

Patient has undergone a surgical procedure during the 30 days before Check-in, other than minor dermatologic procedures.

Patient has an acute or chronic condition that, in the Investigator's opinion, would limit the patient's ability to complete or participate in this clinical study.

Other Exclusion Criteria Per Protocol

Top-Line Metabolic Assessment Results

Metabolic parameters that were measured or calculated were body weight, BMI, plasma fasting glucose, plasma fasting insulin, HbA1C, serum ApoB, serum cholesterol, serum triglycerides, plasma ADMA concentrations and HOMA-IR. The serum levels of alanine transaminase (ALT), aspartate transaminase (AST) and GGT were also measured to assess liver function. These were obtained using standard methods and kits like those regularly used at a standard diagnostic laboratory except when otherwise indicated. Weight was determined using standard doctor's office scales.

No meaningful changes when adjusted to placebo in weight or BMI were observed over the 14 days of treatment.

For this particular clinical trial, "difference" (abbreviated Diff in figures), unless otherwise indicated, and as used below, is placebo adjusted, i.e., it corresponds to the change in value for a certain parameter, on a certain treatment day and for a certain cohort (dosage regimen) compared to its own baseline and relative to change of the same parameter in the placebo group with respect to the placebo group baseline. I.e., Diff=[(parameter value on certain day for certain cohort)−(baseline parameter value for said cohort)]−[(parameter value for said day in placebo group)−(baseline parameter value for placebo group)]. "Change" (or "changes") correspond to difference between the value on a certain treatment day and a certain cohort and its corresponding baseline value.

Figure 18:
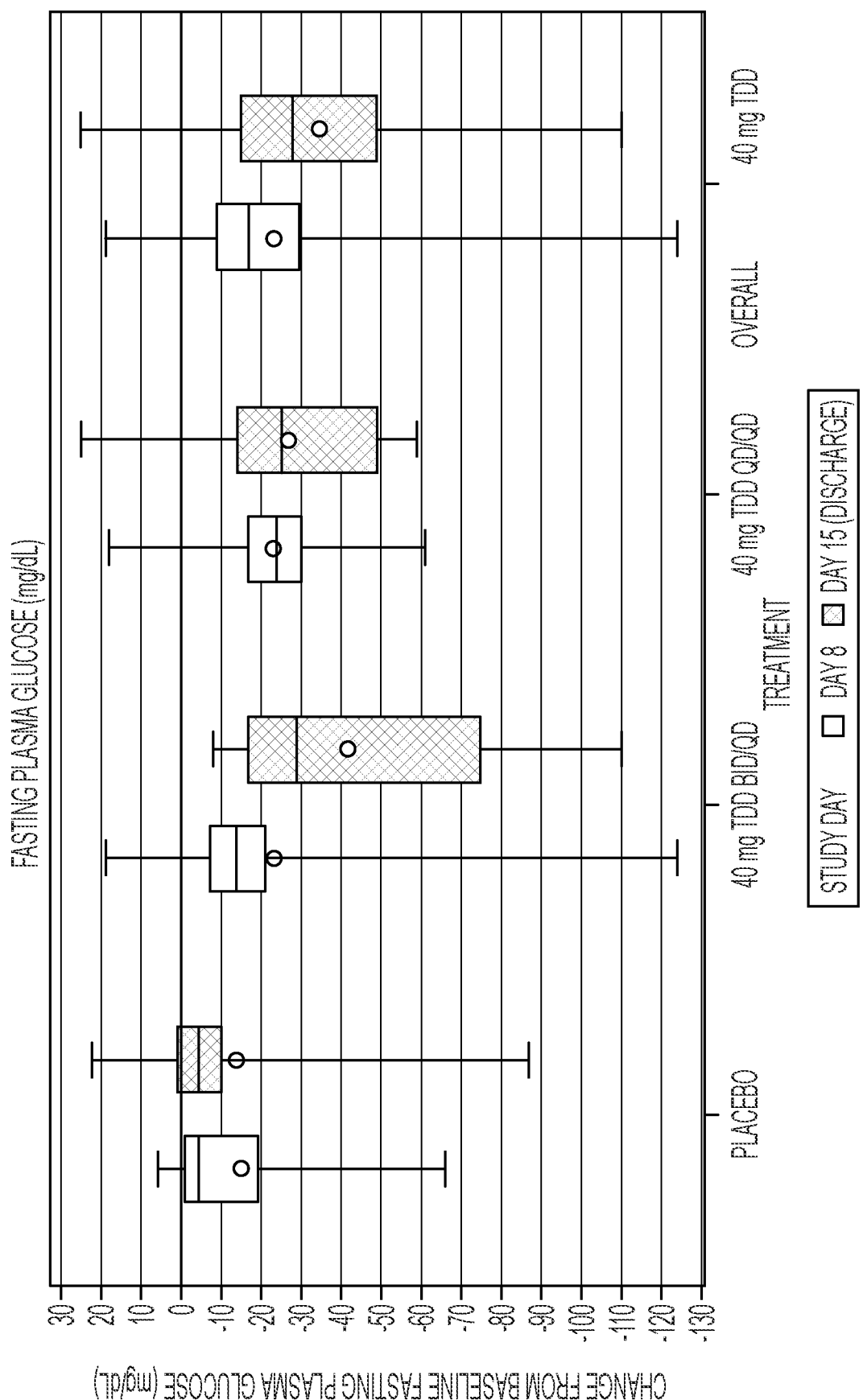
FIG. 18 shows changes from baseline in plasma fasting glucose levels upon treatment with 2 dosage regimens of Compound I or placebo in a clinical study (Example 4). The symbols in the boxplot indicate the mean values. The boxes show the interquartile range (25%-75%) and the whiskers show the low to high range.

FIG. 18 shows changes in fasting plasma glucose levels from baseline on day 8 and day 15, after 7 or 14 days of treatment, respectively for the placebo group, the BID/QD group (20 mg BID days 1-7; 40 mg QD days 8 to 14), the QD/QD group (40 mg QD days 1 to 14) and the combination of the BID/QD and QD/QD groups.

Table 3 summarizes mean values of plasma fasting glucose for the above groups at baseline (mean and median) on the top two rows, as well as the changes on the least square values (LS) from time-matched placebo (day 2) on day 15, after 14 days of treatment and the difference versus placebo as defined above (Diff) on day 15, after 14 days of treatment (all units are mg/dL), on the bottom four rows. The Least Squares mean difference and their associated 95% CI (confidence intervals) are from an ANCOVA model with treatment as fixed effect and baseline as covariate.

TABLE 3

| | | plasma fasting glucose levels | | | |
|---|---|---|---|---|---|
| | | Placebo | BID/QD | QD/QD | Combined group |
| Baseline | Mean (SD) | 142.8 (32.2) | 161.6 (50.4) | 147.3 (35.5) | 154.8 (43.4) |
| | Median | 143.0 | 147.5 | 150.0 | 150.0 |
| | LS Mean reduction from baseline (SE) | −19.7 (8.1) | −35.3 (6.3) | −29.6 (6.6) | −32.5 (4.5) |
| | LS mean reduction from baseline 95% CI | −36.6, −2.8 | −48.5, −22.2 | −43.4, −15.9 | −41.9, −23.0 |
| | LS Mean Diff (SE) | | −15.6 (10.4) | −10.0 (10.4) | −12.8 (9.3) |
| | LS Mean Diff 95% CI | | −37.2, 5.9 | −31.6, 11.7 | −32.2, 6.6 |

Plasma fasting glucose levels on day 15, after 14 days of treatment were reduced by about 16 mg/dL (10%) when compared to placebo for patients administered the BID/QD dosage regimen (20 mg BID days 1-7; then 40 mg QD days 8 to 14. Plasma fasting glucose levels on day 15, after 14 days of treatment were reduced by about 10 mg/dL (7%) when compared to placebo for patients administered the QD/QD dosage regimen (40 mg QD days 1 to 14. For a group combining both dosage regimens, plasma fasting glucose levels on day 15, after 14 days of treatment were reduced by about 13 mg/dL (8%) when compared to placebo.

These metabolic improvements in glucose levels returned to or near baseline values by follow-up, day 42, 28 days after completion of treatment with Compound I.

Figure 19:
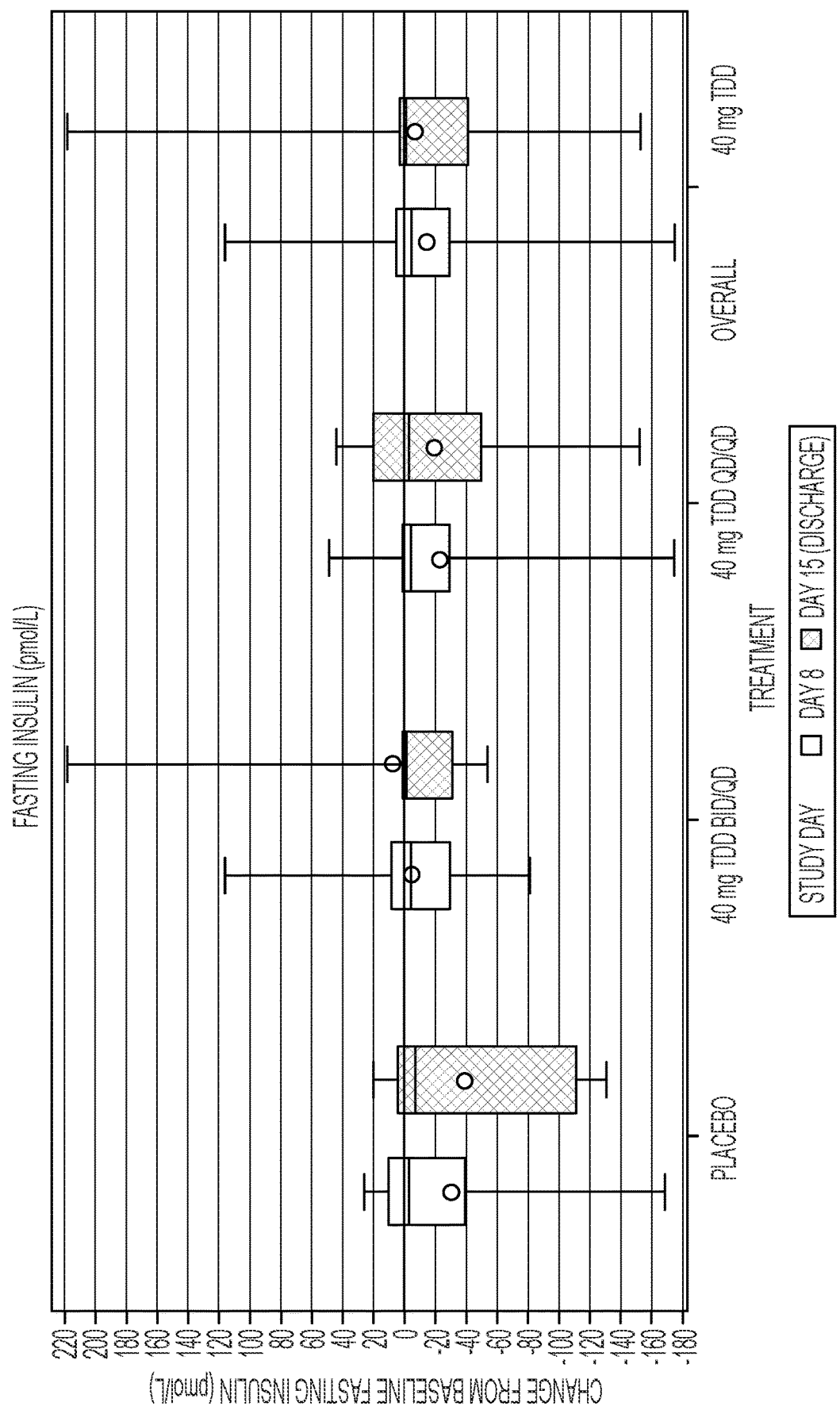
FIG. 19 shows changes from baseline in serum fasting insulin levels upon treatment with 2 dosage regimens of Compound I or placebo in a clinical study (Example 4). The symbols in the boxplot indicate the mean values. The boxes show the interquartile range (25%-75%) and the whiskers show the low to high range.

Improvements in fasting plasma insulin level were observed in the subgroup of patients who were not on insulin therapy (see below). For patients who were on insulin therapy, the insulin levels would be influenced by the amount of the exogenous insulin that was administered to the patient. Therefore, it would not be meaningful to evaluate plasma insulin levels for these patients. As a result, no meaningful improvements in fasting plasma insulin levels over placebo were observed when insulin levels for all of 26 patients, including those who were on insulin therapy, were analyzed (FIG. 19).

Figure 20:
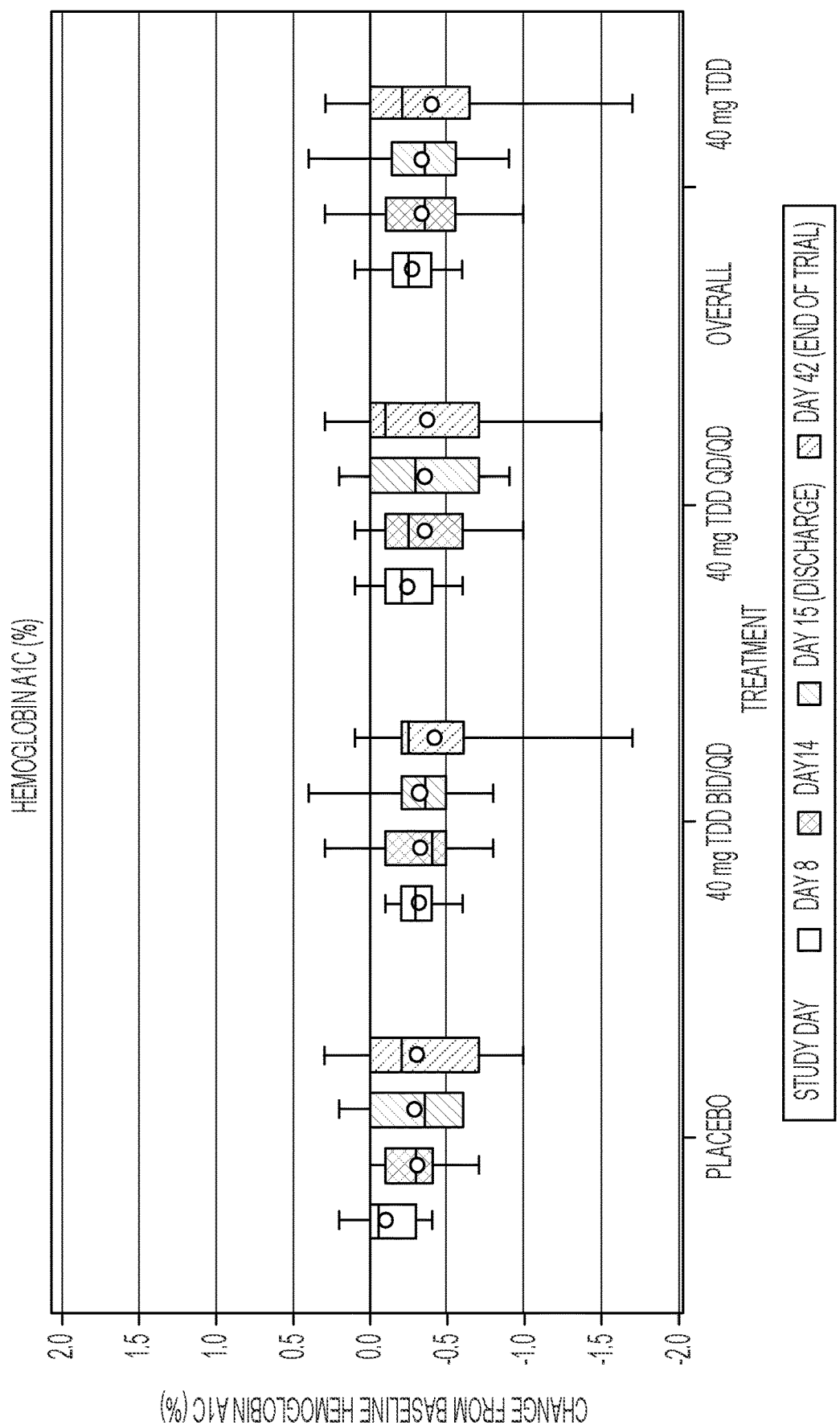
FIG. 20 shows changes from baseline in levels of HbA1C upon treatment with 2 dosage regimens of Compound I or placebo in a clinical study (Example 4). The symbols in the boxplot indicate the mean values. The boxes show the interquartile range (25%-75%) and the whiskers show the low to high range.

No meaningful improvements in HbA1C levels over placebo were observed in this trial (FIG. 20). Trial duration was most likely too short to allow for observation of changes in this parameter.

Figure 21:
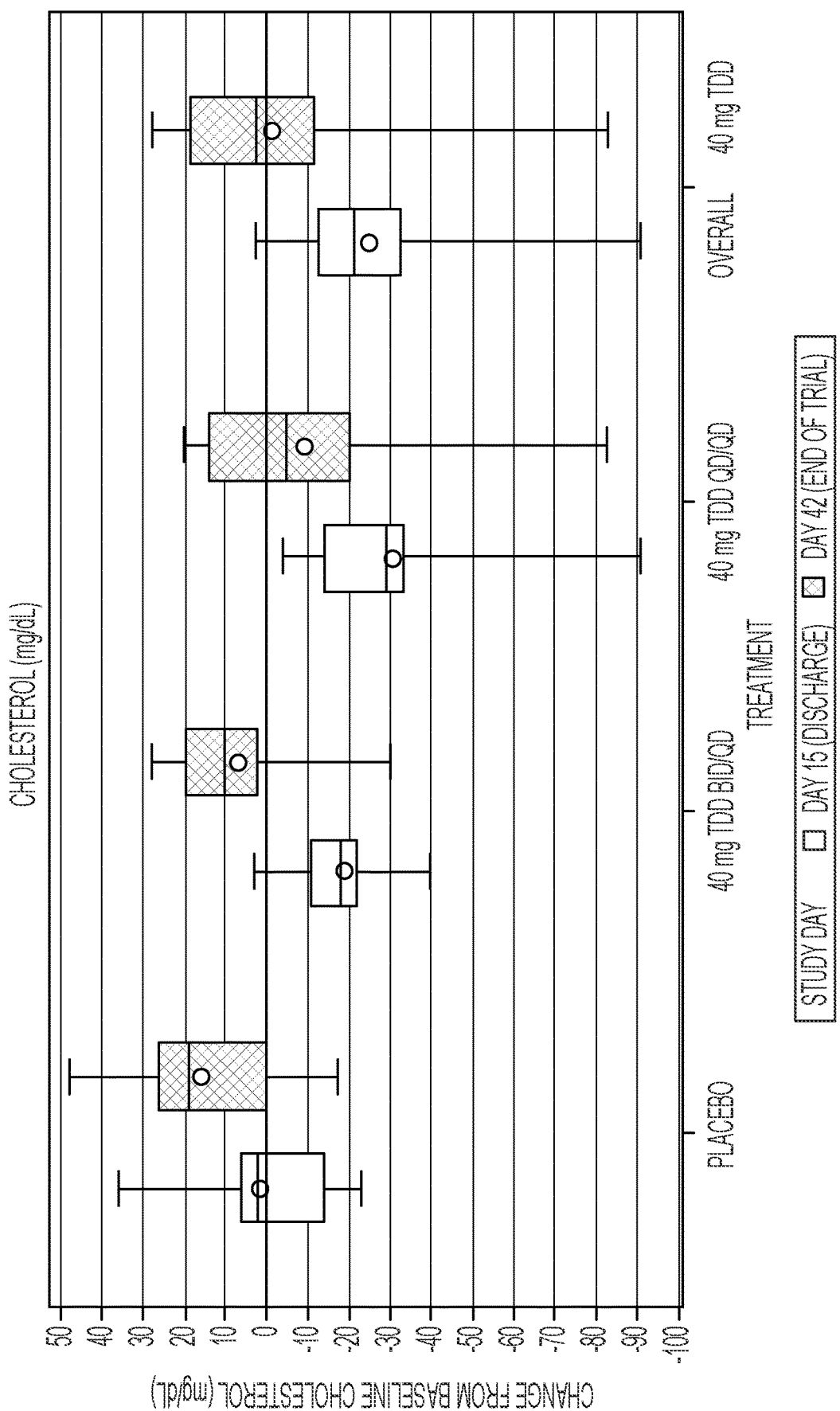
FIG. 21 shows changes from baseline in serum cholesterol levels upon treatment with 2 dosage regimens of Compound I or placebo in a clinical study (Example 4). The symbols in the boxplot indicate the mean values. The boxes show the interquartile range (25%-75%) and the whiskers show the low to high range.

FIG. 21 shows changes in serum cholesterol levels from baseline on day 15 (discharge, after 14 days of treatment) and day 42 (follow-up), for the placebo group, the BID/QD group (20 mg BID days 1-7; 40 mg QD days 8 to 14), the QD/QD group (40 mg QD days 1 to 14) and the combination of the BID/QD and QD/QD groups.

Table 4 summarizes mean values of serum cholesterol for the above groups at baseline (mean and median) on the top two rows, as well as the changes in least square values (LS) from baseline on day 15, after 14 days of treatment and the difference versus placebo as defined above (Diff) on day 15 (after 14 days treatment, all units are mg/dL) on the four bottom rows.

Serum cholesterol levels on day 15, after 14 days of treatment were reduced by about 20 mg/dL (13%) when compared to placebo for patients administered the BID/QD dosage regimen (20 mg BID days 1-7; then 40 mg QD days 8 to 14). Serum cholesterol levels on day 15, after 14 days of treatment were reduced by about 30 mg/dL (18%) when compared to placebo for patients administered the QD/QD dosage regimen (40 mg QD days 1 to 14). For a group combining both dosage regimens, serum cholesterol levels on day 15, after 14 days of treatment, were reduced by about 25 mg/dL (16%) when compared to placebo. Improvements in cholesterol levels had returned to baseline or close to baseline by day 42 (follow up). These reductions in cholesterol levels are attributable to reductions in LDL, while HDL cholesterol remained unchanged (See FIGS. 22 and 23).

Figure 22:
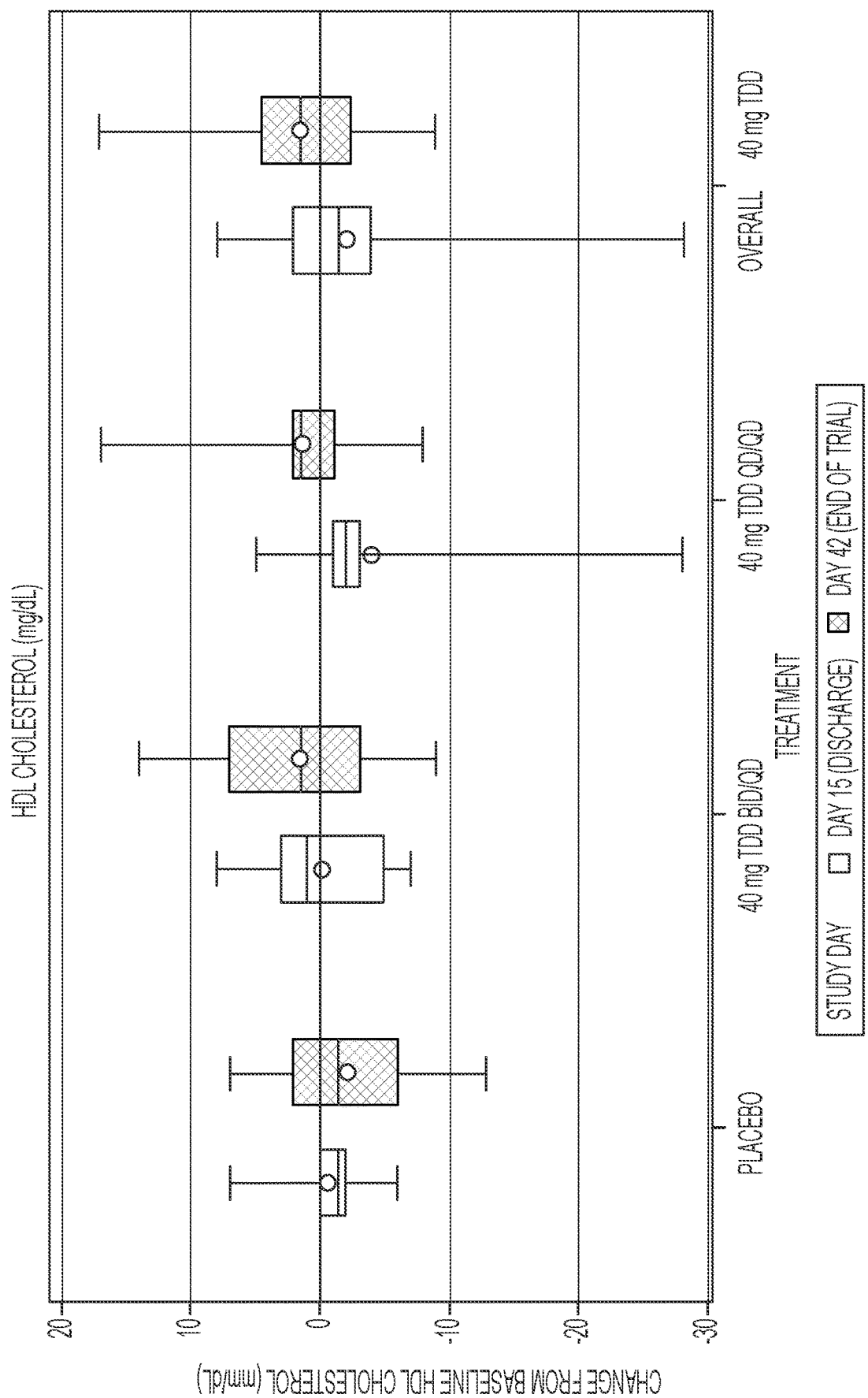
FIG. 22 shows changes from baseline in values of serum HDL cholesterol upon treatment with 2 dosage regimens of Compound I or placebo in a clinical study (Example 4). The symbols in the boxplot indicate the mean values. The boxes show the interquartile range (25%-75%) and the whiskers show the low to high range.
Figure 23:
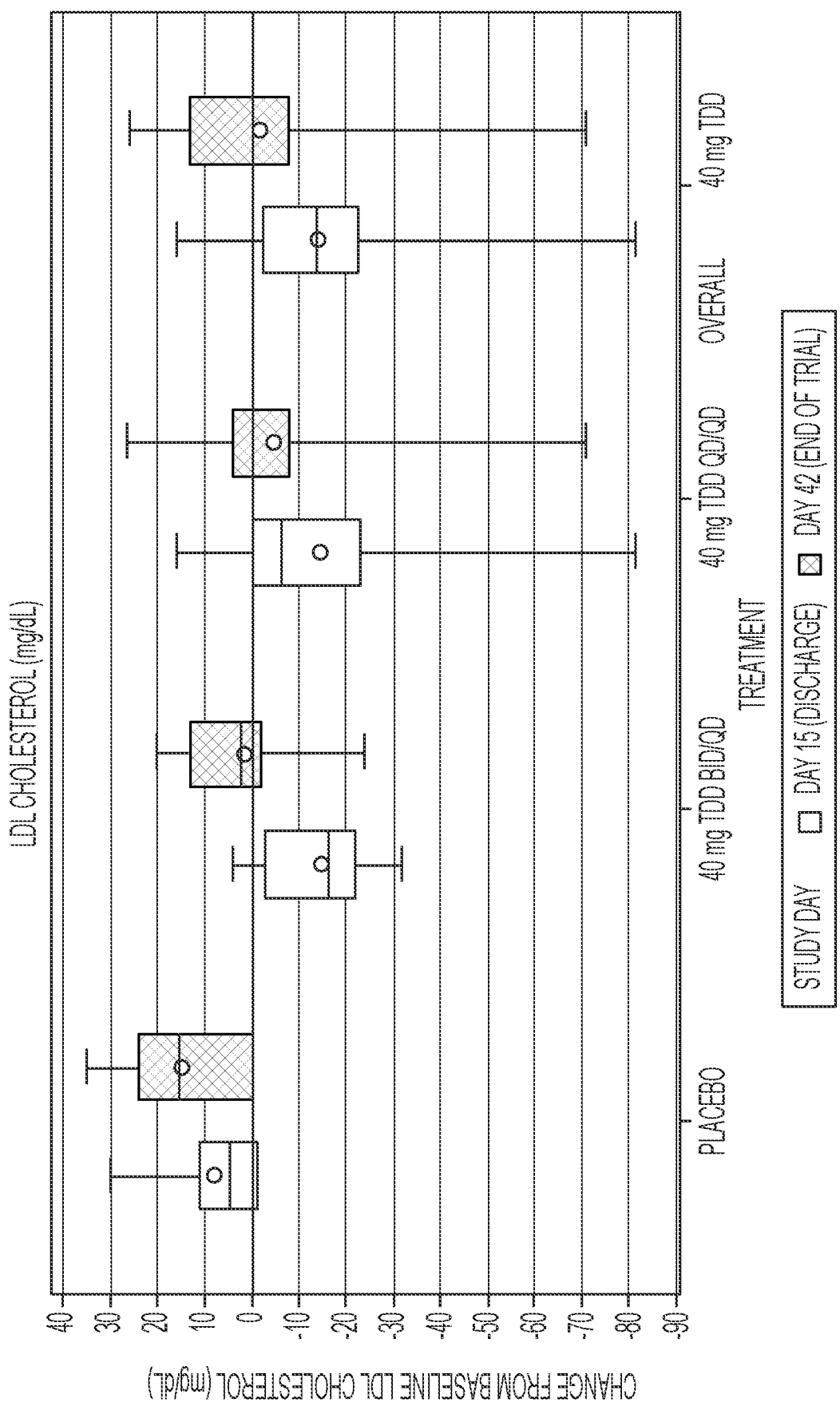
FIG. 23 shows changes from baseline in serum LDL cholesterol levels upon treatment with 2 dosage regimens of Compound I or placebo in a clinical study (Example 4). The symbols in the boxplot indicate the mean values. The boxes show the interquartile range (25%-75%) and the whiskers show the low to high range.

FIGS. 22 and 23 show changes in HDL and LDL serum cholesterol levels from baseline on day 15 (discharge, after 14 days of treatment) and day 42 (follow-up), for the placebo group, the BID/QD group (20 mg BID days 1-7; 40 mg QD days 8 to 14), the QD/QD group (40 mg QD days 1 to 14) and the combination of the BID/QD and QD/QD groups.

Table 5A summarizes mean least square (LS) change values of serum LDL cholesterol for the above groups as changes from baseline on day 15, after 14 days of treatment, and the difference versus placebo as defined above (Diff) on day 15 (after 14 days of treatment, all units are mg/dL).

TABLE 4

Changes in serum cholesterol levels.

| | | Placebo | BID/QD | QD/QD | Combined group |
|---|---|---|---|---|---|
| Baseline | Mean (SD) | 152.5 (49.0) | 150.7 (26.7) | 164.4 (34.1) | 157.6 (30.6) |
| | Median | 132.5 | 150.0 | 160.5 | 156.5 |
| | LS Mean reduction from baseline (SE) | 0.8 (7.8) | −20.2 (6.1) | −29.3 (6.1) | −24.7 (4.3) |
| | LS mean reduction from baseline 95% CI | −15.5, 17.0 | −32.8, −7.5 | −42.0, −16.6 | −33.6, −15.8 |
| | LS Mean Diff (SE) | | −20.9 (9.9) | −30.1 (10.0) | −25.5 (9.0) |
| | LS Mean Diff 95% CI | | −41.5, −0.4 | −50.8, −9.3 | −44.1, −6.9 |

TABLE 5A

Reductions in LDL cholesterol (all are least square values).

|  | Placebo | BID/QD | QD/QD | Combined group |
|---|---|---|---|---|
| Mean reduction from baseline (SE) | 6.2 (7.3) | −14.0 (5.6) | −13.7 (5.6) | −13.9 (4.0) |
| mean reduction from baseline 95% CI | −8.9, 21.2 | −25.6, −2.3 | −25.3, −2.1 | −22.1, −5.6 |
| Mean Diff (SE) |  | −20.2 (9.2) | −19.9 (9.2) | −20.2 (8.3) |
| Mean Diff 95% CI |  | −39.3, −1.1 | −38.9, −0.9 | −37.2, −2.8 |

Serum LDL cholesterol levels on day 15, after 14 days of treatment were reduced by about 20 mg/dL (13% of total cholesterol) when compared to placebo for patients administered the BID/QD dosage regimen (20 mg BID days 1-7; then 40 mg QD days 8 to 14). Serum LDL cholesterol levels on day 15, after 14 days of treatment were reduced by about 20 mg/dL (13% of total cholesterol) when compared to placebo for patients administered the QD/QD dosage regimen (40 mg QD days 1 to 14). For a group combining both dosage regimens, serum LDL cholesterol levels on day 15, after 14 days of treatment were reduced by about 20 mg/dL (13%) when compared to placebo. Improvements in serum LDL cholesterol levels had returned to baseline or close to baseline by day 42 (follow up). Levels of HDL remained closed to baseline throughout the trial (FIG. 22).

Figure 25:
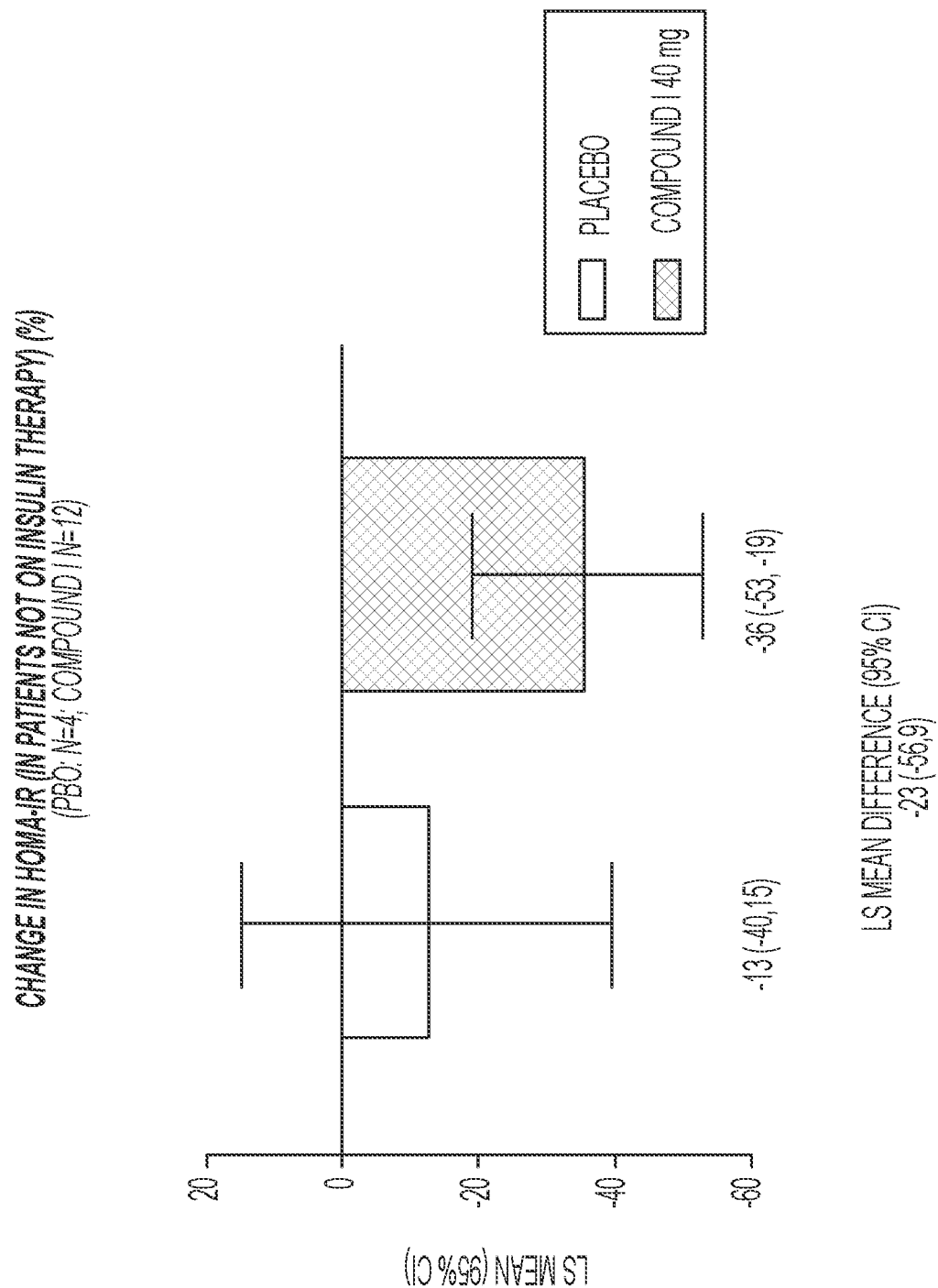
FIG. 25 shows the effect of Compound I on improvement of insulin resistance demonstrated by changes in HOMA-IR values upon treatment with 40 mg (data for BID/QD and QD/QD dosage regimens combined) of Compound I or placebo in patients who were not on insulin therapy (Example 4).
Figure 26:
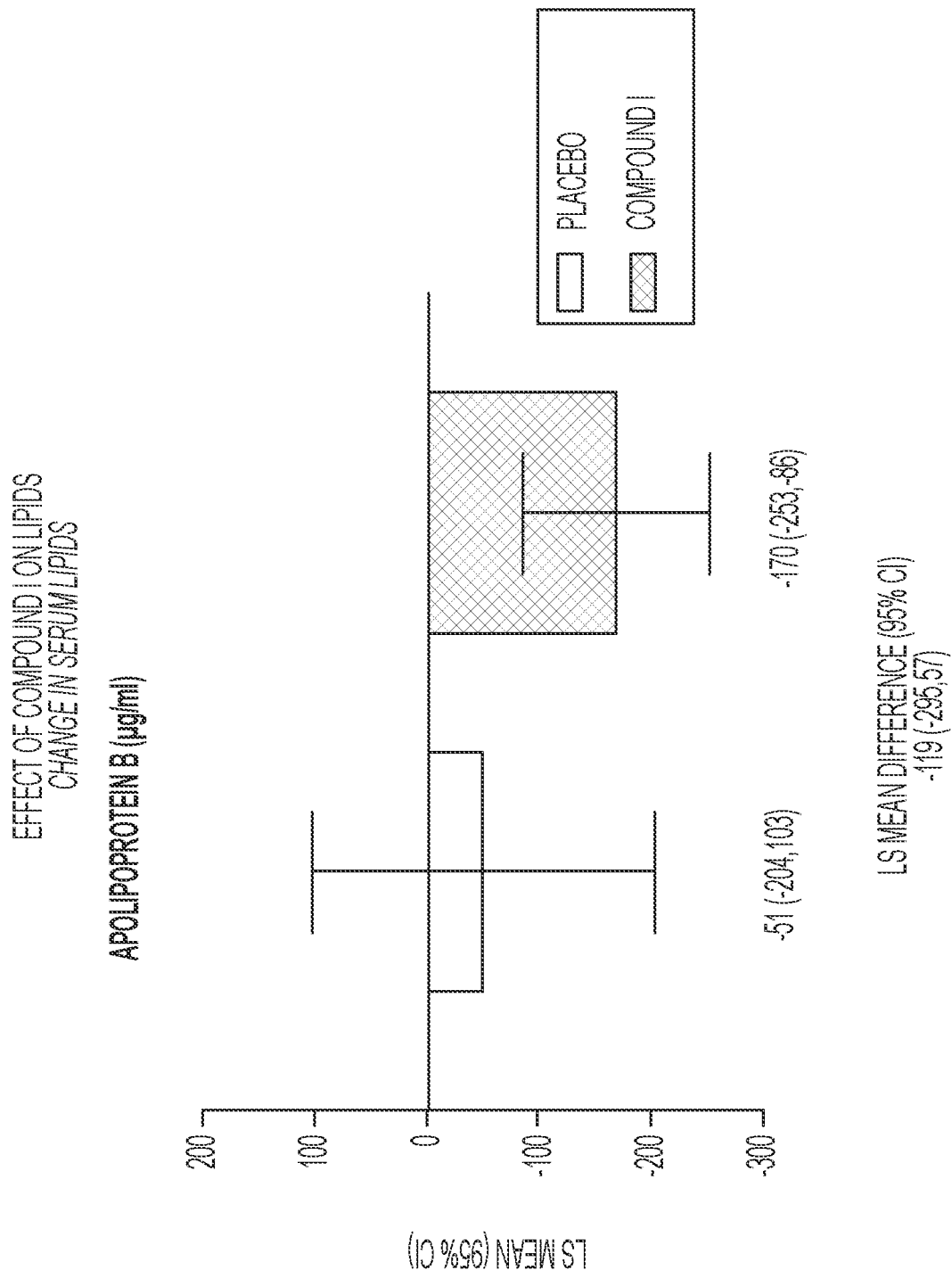
FIG. 26 shows changes from baseline in serum apolipoprotein B levels in patients treated with 40 mg (data for BID/QD and QD/QD dosage regimens combined) of Compound I or placebo in a clinical study (Example 4).

Table 5B summarizes mean least squares (LS) change values of serum Apolipoprotein B (ApoB) for the above groups as changes from baseline on day 15, after 14 days of treatment and the difference versus placebo as defined above (Diff) on day 15 (after 14 days of treatment, all units are µg/mL). FIG. 25 shows changes in serum ApoB levels from baseline for the placebo group and the overall treatment groups (i.e., the combination of the BID/QD and QD/QD groups).

TABLE 5B

Reductions in serum Apo B values

|  |  | Placebo | Compound I 40 mg Total Daily Dose | | |
|---|---|---|---|---|---|
|  | Parameter (Units)/ Metabolic function Apolipoprotein B (ug/ml) | (N = 6) | BID/QD (N = 10) | QD/QD (N = 10) | Overall (N = 20) |
| Baseline | Mean (SD) | 1147.3 (346.4) | 1022.6 (322.3) | 1001.7 (233.4) | 1012.2 (274.1) |
|  | Median | 1030.5 | 920.5 | 985.5 | 935.0 |
| Change | LS Mean (SE) | −50.5 (74.0) | −219.4 (56.5) | −119.6 (56.7) | −169.5 (40.1) |
|  | 95% LS Mean CI | −204.1, 103.0 | −336.6, −102.3 | −237.2, −2.1 | −252.7, −86.4 |
|  | LS Mean Diff (SE) |  | −168.9 (93.5) | −69.1 (94.0) | 119.0 (84.8) |
|  | 95% LS Mean Diff CI |  | −362.8, 25.0 | −264.0, 125.8 | −294.9, 56.9 |

Figure 24:
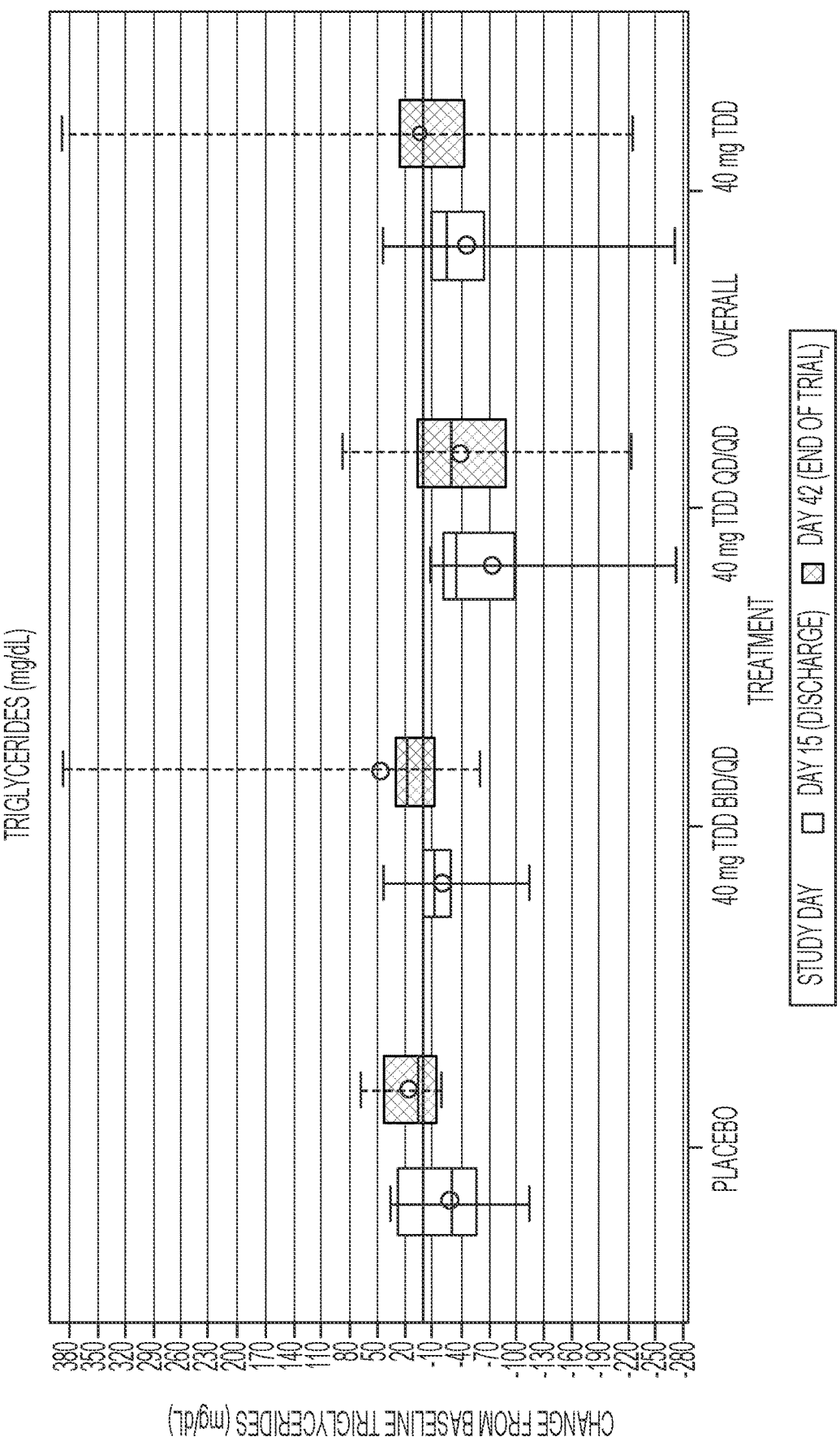
FIG. 24 shows changes from baseline in serum triglyceride (TG) levels upon treatment with 2 dosage regimens of Compound I or placebo in a clinical study (Example 4). The symbols in the boxplot indicate the mean values. The boxes show the interquartile range (25%-75%) and the whiskers show the low to high range.

FIG. 24 shows changes in serum triglyceride (TG) levels from baseline on day 15 (discharge, after 14 days of treatment) and day 42 (follow-up), for the placebo group, the BID/QD group (20 mg BID days 1-7; 40 mg QD days 8 to 14), the QD/QD group (40 mg QD days 1 to 14) and the combination of the BID/QD and QD/QD groups.

Table 6 summarizes mean values of serum triglycerides for the above groups at baseline (mean and median) on the top two rows, as well as the change in least square values from baseline on day 15, after 14 days of treatment and the difference versus placebo as defined above (Diff) on day 15 (after 14 days of treatment, all units are mg/dL), on the last four rows.

TABLE 6

Reductions in triglycerides.

|  |  |  |  |  |  |
|---|---|---|---|---|---|
| Baseline | Mean (SD) | 149.8 (64.2) | 111.2 (48.8) | 199.1 (125.4) | 155.2 (103.0) |
|  | Median | 148.5 | 106.0 | 149.0 | 126.5 |

TABLE 6-continued

Reductions in triglycerides.

|  |  | Placebo | BID/QD | QD/QD | Combined group |
|---|---|---|---|---|---|
| Δ at Day 15 | LS Mean reduction from baseline (SE) | −32.0 (12.2) | −46.4 (9.9) | −46.0 (9.9) | −46.2 (6.7) |
|  | LS mean reduction from baseline 95% CI | −57.3, −6.8 | −66.9, −25.9 | −66.6, −25.4 | −60.0, −32.3 |
|  | LS Mean Diff (SE) |  | −14.3 (15.6) | −14.0 (15.8) | −14.2 (13.9) |
|  | LS Mean Diff 95% CI |  | −46.8, 18.1 | −46.7, 18.8 | −43.0, 14.7 |

Serum TG levels on day 15, after 14 days of treatment were reduced by about 14 mg/dL (13%) when compared to placebo for patients administered the BID/QD dosage regimen (20 mg BID days 1-7; then 40 mg QD days 8 to 14). Serum TG levels on day 15, after 14 days of treatment were reduced by about 14 mg/dL (13%) when compared to placebo for patients administered the QD/QD dosage regimen (40 mg QD days 1 to 14). For a group combining both dosage regimens, serum TG levels on day 15, after 14 days of treatment were reduced by about 14 mg/dL (13%) when compared to placebo. Improvements in serum triglyceride levels had returned to baseline or close to baseline by day 42 (follow up).

Figure 27:
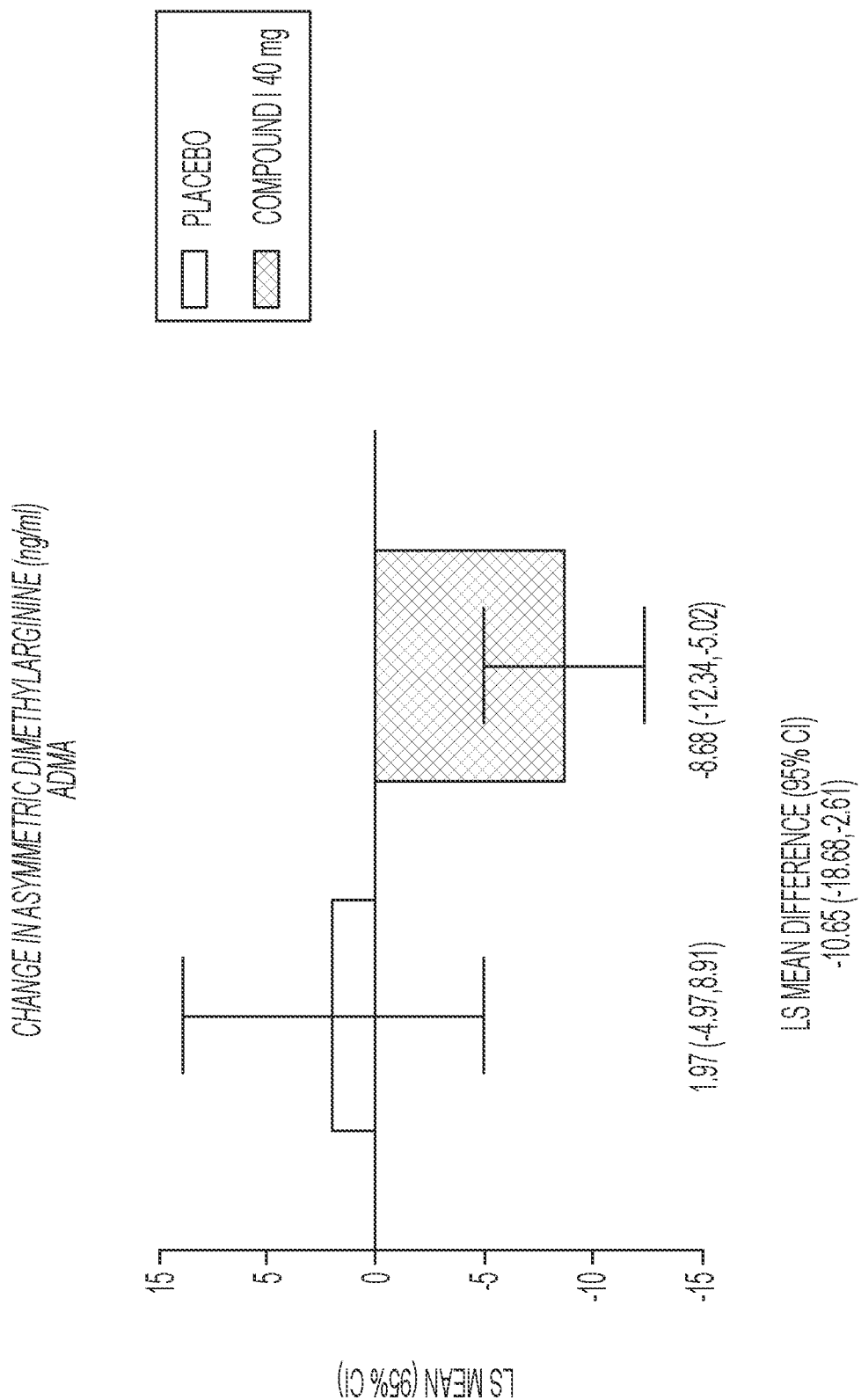
FIG. 27 shows changes from baseline in asymmetric dimethylarginine (ADMA) concentrations upon treatment with 40 mg (data for BID/QD and QD/QD dosage regimens combined) of Compound I or placebo in a clinical study (Example 4).

ADMA (Asymmetric dimethylarginine) is a plasma biomarker associated with impaired endothelial function and cardiovascular risk. It is consistently elevated in conditions adversely affecting microvascular function and associated with cardiovascular event risk. The ADMA plasma concentration declined from baseline and compared to placebo over the course of the 14 day study. The combined Compound I group demonstrated decreases of 8.7 ng/ml from a baseline of 105 ng/ml, while the placebo group increased by 2.0 ng/ml from a baseline of 115 ng/ml. The mean reduction adjusted to placebo was of about 11 ng/mL (see FIG. 27).

Figure 28B:
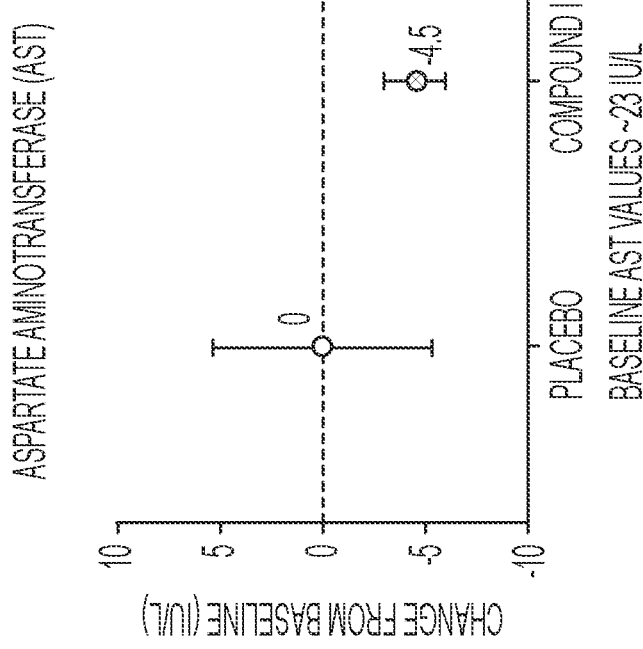
FIGS. 28A and 28B show changes from baseline in serum levels of alanine transaminase (ALT) (FIG. 28A) and aspartate transaminase (AST) (FIG. 28B) upon treatment with 40 mg (data for BID/QD and QD/QD dosage regimens combined) of Compound I or placebo in a clinical study (Example 4).
Figure 28A:
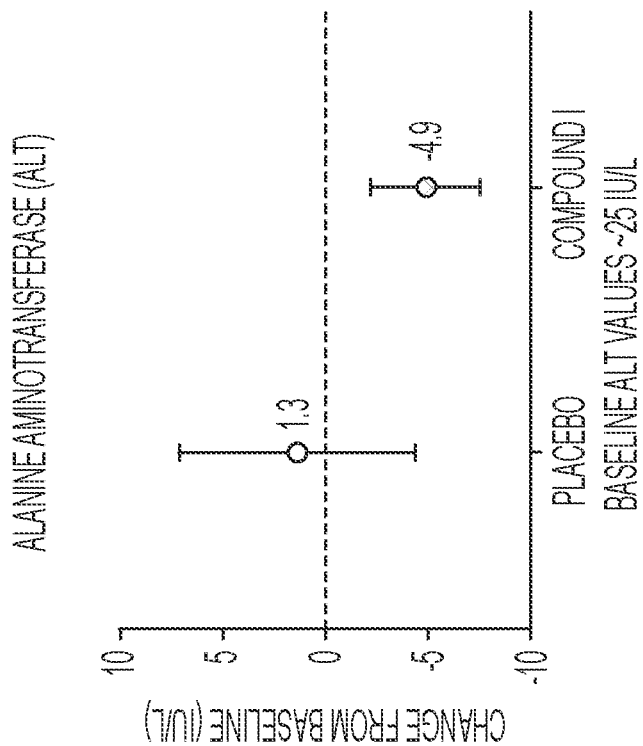

Serum levels of liver enzymes, such as alanine transaminase (ALT), asparatate transaminase (AST), and gamma-glutamyltransferase (GGT), can be used as biomarkers for liver function. As shown in FIGS. 28A and 28B, the mean serum levels of ALT and AST decreased from baseline in patients treated with Compound I; while the mean serum levels of ALT and AST for patients in placebo group showed slight increase or no change from baseline. Specifically, the mean serum level for ALT decreased 4.9 IU/L from baseline for patients treated with Compound I; while patients in placebo group had a slight increase of 1.3 IU/L. Similarly, the mean serum level for AST decreased 4.5 IU/L from baseline for patients treated with Compound I; while patients in placebo group showed no change. Similarly, the mean serum level for GGT decreased 2.4 U/L from baseline for patients treated with Compound I; while patients in placebo group had a slight increase of 0.5 U/L.

HOMA-IR stands for Homeostatic model assessment (HOMA) of insulin resistance (IR) and is a method for assessing β-cell function and insulin resistance from basal (fasting) glucose and insulin or C-peptide concentrations. The normal HOMA-IR value for healthy human ranges from 0.5 to 1.4. Less than 1.0 means the person is insulin-sensitive which is optimal. A value above 1.9 is indicative of early insulin resistance.

In patients not taking concomitant insulin (i.e., 16 patients treated only with oral antihyperglycemic agents and not insulin of which 12 were on Compound I and 4 on PBO), the reduction in HOMA-IR was a 36% from baseline in patients on the study drug, and a reduction of 23% was calculated when adjusted to placebo (see FIG. 25). This is suggestive of improved insulin sensitivity in treated patients after 14 days.

In this group of patients not on insulin, a reduction in fasting plasma insulin was also observed (−13 pmol/L) adjusted to placebo.

Conclusions

Compound I reduced plasma fasting glucose levels over 14 days of dosing, by about 30 mg/dL (about 20%) from baseline, and about 13 mg/dL (8%) greater than placebo.

Post-hoc subgroup analyses by concomitant blood glucose lowering medication use were also performed. Results were similar for both regimens after 14 days of treatment and were therefore combined. Of the 26 patients enrolled in the trial, 16 patients were using oral antihyperglycemic agents without insulin. Relative to placebo, in the subgroup of patients who were using only oral antihyperglycemic agents without insulin, a mean decrease of plasma blood glucose of −19 mg/L was measured. These results support a positive effect of the sGC stimulator treatment on glucose reduction independent of and also additive to the effect of other oral blood glucose reduction medications.

Reductions from baseline in both total and LDL cholesterol were observed in Compound I treated patients, while no changes were evident in PBO-treated patients. Compound I reduced serum cholesterol by about 26 mg/dL (about 15%) over 14 days, an effect not observed in the placebo group. Reductions where attributable to LDL, with no changes in the levels of HDL.

Post-hoc subgroup analyses by concomitant antihyperlipidemic medication use were also performed. Results were similar for both regimens after 14 days of treatment and were therefore combined. Of the 26 patients enrolled in the trial, 18 patients were using statins (15 treated with Compound I and 3 with placebo). Both total and LDL cholesterol decreased in treated vs. placebo patients in the subgroup of 18 patients on concomitant statin therapy [−17 mg/dL and −16 mg/dL, respectively]. These results support a positive effect of Compound I treatment on total and LDL cholesterol reduction independent of and additive to the effect of statin medications.

Post-hoc analysis of apolipoprotein B (ApoB) was consistent with the greater declines in Compound I vs. PBO-treated patients observed for other lipids (−119 μg/ml). Mean Apo-B levels declined by approximately 17% in treated patients, a decline that was greater than that observed in placebo treated patients.

Substantial reductions from baseline values (of 36 mg/dL, or about 30%) and from placebo (of about 13 mg/dL (about 10%) over placebo in serum triglycerides were also observed over 14 days.

Patients treated with Compound I showed reduction of about 11 ng/mL over placebo in plasma ADMA concentrations after 14 days of treatment.

Patients treated with Compound I also showed significant reductions in serum levels of liver enzymes ALT (−4.9 IU/L, 20% reduction) and AST (−4.5 IU/L, 20% reduction) over 14 days as compared to baseline. Patients in the placebo group showed slight increase (1.3 IU/L) in serum ALT level and no change in serum AST level.

Post-hoc subgroup analyses of patients who were not taking concomitant insulin showed that HOMA-IR for patients treated with Compound I over 14 days declined by 36% from baseline and 23% when adjusted to placebo, indicating improved insulin sensitivity in treated patients after 14 days.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

The invention claimed is:

1. A method of treating a human patient with metabolic syndrome comprising administering to said patient a single oral daily dose of between 10 mg and 50 mg of Compound I:

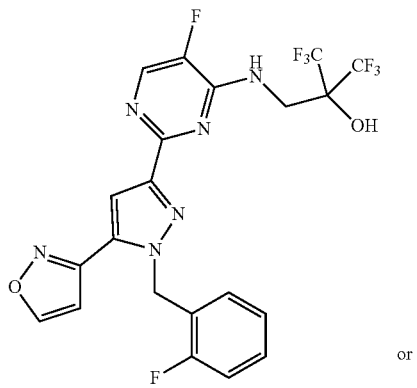 [SMILES: OC(CNc1nc(-c2cc(-c3ccon3)n(Cc3ccccc3F)n2)ncc1F)(C(F)(F)F)C(F)(F)F]

or an oral dose of 20 mg of Compound I twice a day.

2. A method of reducing the level of a metabolic marker selected from the group consisting of fasting blood glucose, fasting blood insulin, HbA1C, blood cholesterol, apolipoprotein B (ApoB), blood triglyceride, and body weight in a human patient in need thereof comprising administering to said patient a single oral daily dose of between 10 mg and 50 mg of Compound I:

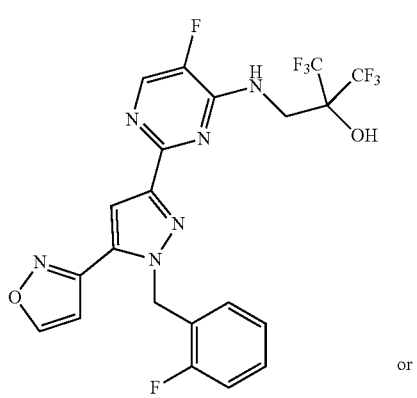 [SMILES: OC(CNc1nc(-c2cc(-c3ccon3)n(Cc3ccccc3F)n2)ncc1F)(C(F)(F)F)C(F)(F)F]

or an oral dose of 20 mg of Compound I twice a day.

3. A method of (i) increasing insulin sensitivity or (ii) improving endothelial function and reducing cardiovascular risk in a human patient in need thereof comprising administering to said patient a single oral daily dose of between 10 mg and 50 mg of Compound I:

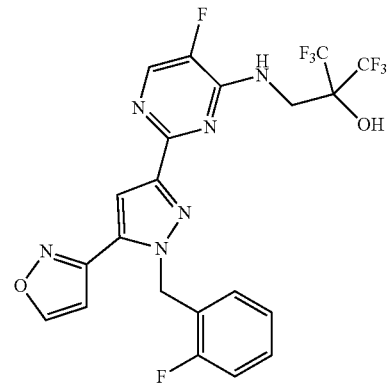

or an oral dose of 20 mg of Compound I twice a day.

4. The method of claim 1, wherein the method comprises administering to said patient a single oral daily dose of between 10 mg and 50 mg of Compound I.

5. The method of claim 1, wherein the method comprises administering to said patient a single oral daily dose of 10 mg of Compound I.

6. The method of claim 1, wherein the method comprises administering to said patient a single oral daily dose of 20 mg of Compound I.

7. The method of claim 1, wherein the method comprises administering to said patient a single oral daily dose of 30 mg of Compound I.

8. The method of claim 1, wherein the method comprises administering to said patient a single oral daily dose of 40 mg of Compound I.

9. The method of claim 1, wherein the method comprises administering to said patient a single oral daily dose of 50 mg of Compound I.

10. The method of claim 1, wherein the method comprises administering to said patient an oral dose of 20 mg of Compound I twice a day.

11. The method of claim 10, wherein the method comprises administering to said patient a first oral dose of 20 mg and a second oral dose of 20 mg, wherein the first dose and the second dose are separated by 5 hours to 15 hours.

12. The method of claim 1, wherein the method further comprises administering to said patient one or more anti-hypertensive medications.

13. The method of claim 12, wherein the one or more anti-hypertensive medications are independently selected from an angiotensin-converting enzyme (ACE) inhibitor and an angiotensin II receptor blocker (ARB).

14. The method of claim 12, wherein the method further comprises administering to said patient one or more blood glucose lowering medications.

15. The method of claim 1, wherein the method further comprises administering to said patient one or more anti-hypertensive medications selected from the group consisting of lisinopril, combination of lisinopril and hydrochlorothiazide, enalapril, losartan, metoprolol, and spironolactone and one or more blood glucose lowering medications selected from the group consisting of insulin, metformin, and glipizide.

16. The method of claim 1, wherein the method further comprises administering to said patient one or more antihypertensive medications selected from the group consisting of lisinopril, combination of lisinopril and hydrochlorothiazide, enalapril, losartan, benazepril, amlodipine, hydrochlorothiazide, ramipril, losartan potassium-hydrochlorothiazide valsartan, captopril, atenolol, metoprolol, and spironolactone and one or more blood glucose lowering medications selected from the group consisting of insulin, metformin, linagliptin, and glipizide.

17. The method of claim 1, the method further comprises administering to said patient one or more anti-hypertensive medications selected from the group consisting of lisinopril, combination of lisinopril and hydrochlorothiazide, enalapril, losartan, benazepril, amlodipine, hydrochlorothiazide, ramipril, losartan potassium-hydrochlorothiazide, valsartan, captopril, atenolol, metoprolol, and spironolactone and one or more blood glucose lowering medications selected from the group consisting of metformin, linagliptin, and glipizide.

18. The method of claim 14, wherein the method further comprises administering to said patient one or more anti-hyperlipidemic medications.

19. The method of claim 18, wherein the one or more anti-hyperlipidemic medications are independently selected from the group consisting of atorvastin, pravastatin, simvastatin, rosuvastatin, lovastatin and nicotinic acid.

20. The method of claim 1, wherein the oral dose of Compound I is administered as multiples of a 5 mg oral tablet dosage form.

21. The method of claim 1, wherein the method further improves liver function in a human patient in need thereof.

\* \* \* \* \*

UNITED STATES PATENT AND TRADEMARK OFFICE
CERTIFICATE OF CORRECTION

| | | |
|---|---|---|
| PATENT NO. | : 11,389,449 B2 | Page 1 of 1 |
| APPLICATION NO. | : 16/645955 | |
| DATED | : July 19, 2022 | |
| INVENTOR(S) | : Hanrahan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 82 days.

Signed and Sealed this
Eighteenth Day of February, 2025

Coke Morgan Stewart
*Acting Director of the United States Patent and Trademark Office*